US008834698B2

(12) United States Patent
Lau et al.

(10) Patent No.: US 8,834,698 B2
(45) Date of Patent: Sep. 16, 2014

(54) DEVICES AND METHODS FOR OPTOELECTRONIC MANIPULATION OF SMALL PARTICLES

(75) Inventors: Aldrich Lau, Palo Alto, CA (US); Joon Yang, Redwood City, CA (US); Huan Phan, Belmont, CA (US); Steven Sherwood, Los Altos, CA (US); Hans Fuernkranz, Saratoga, CA (US)

(73) Assignee: Life Technologies Corporation, Carlsbad, CA (US)

( * ) Notice: Subject to any disclaimer, the term of this patent is extended or adjusted under 35 U.S.C. 154(b) by 432 days.

(21) Appl. No.: 12/702,137

(22) Filed: Feb. 8, 2010

(65) Prior Publication Data

US 2010/0206731 A1    Aug. 19, 2010

Related U.S. Application Data

(63) Continuation of application No. 11/552,853, filed on Oct. 25, 2006, now abandoned.

(60) Provisional application No. 60/731,123, filed on Oct. 27, 2005.

(51) Int. Cl.
| | |
|---|---|
| *B03C 11/00* | (2006.01) |
| *C07K 1/26* | (2006.01) |
| *B03C 5/02* | (2006.01) |
| *B03C 5/00* | (2006.01) |
| *G01N 27/30* | (2006.01) |

(52) U.S. Cl.
CPC .............. *B03C 5/026* (2013.01); *G01N 27/305* (2013.01); *C07K 1/26* (2013.01); *B03C 5/028* (2013.01); *B03C 5/005* (2013.01)
USPC .......................... 204/547; 204/643; 435/288.7

(58) Field of Classification Search
USPC ................ 204/450–470, 546–550, 600–621, 204/641–645; 435/283.1, 288.7, 285.2; 250/368, 301.1, 203.7, 206.3, 578.1, 250/234, 471.1; 422/68.1, 502
See application file for complete search history.

(56) References Cited

U.S. PATENT DOCUMENTS 4,545,677 A    10/1985   Chupp
4,661,913 A     4/1987   Wu
(Continued)

FOREIGN PATENT DOCUMENTS

WO     WO 2005/100541 A2     10/2005

OTHER PUBLICATIONS

"Brochure for BO FACSCantoTM Flow Cytometer,BD Biosciences", www.bdbiosciences.com, (Apr. 2004),10 pages.

(Continued)

*Primary Examiner* — Luan Van
*Assistant Examiner* — Gurpreet Kaur

(57) ABSTRACT

A method for sorting cells in a biological sample comprising a first type of cells and a second type of cells may comprise introducing the biological sample into a chamber comprising a first surface and a second surface, wherein the first surface is associated with a transparent electrode and the second surface is associated with a photoconductive portion of an electrode. The method may further comprise moving incident light and the photoconductive portion relative to one another so as to illuminate regions of the photoconductive portion and modulate an electric field in the chamber in proximity to the illuminated regions. The method may further comprise separating the first type of cells from the second type of cells in the chamber via dielectrophoretic movement of the first type of cells and the second type of cells caused by the modulated electric field, wherein a dielectrophoretic characteristic of at least one of the first type of cells and the second type of cells has been modified.

22 Claims, 32 Drawing Sheets

(56) References Cited

U.S. PATENT DOCUMENTS

| | | | |
|---|---|---|---|
| 4,756,427 | A | 7/1988 | Gohde |
| 4,859,582 | A | 8/1989 | Stryer et al. |
| 5,007,732 | A | 4/1991 | Ohki et al. |
| 5,888,370 | A | 3/1999 | Becker et al. |
| 5,993,692 | A | 11/1999 | Tarumi |
| 6,287,832 | B1 | 9/2001 | Becker et al. |
| 6,641,708 | B1 | 11/2003 | Becker et al. |
| 6,749,736 | B1 | 6/2004 | Fuhr et al. |
| 6,790,330 | B2 | 9/2004 | Gascoyne et al. |
| 7,141,863 | B1 | 11/2006 | Compaan et al. |
| 2001/0021534 | A1 | 9/2001 | Wohlstadter et al. |
| 2001/0031309 | A1 | 10/2001 | Lee et al. |
| 2002/0160470 | A1 | 10/2002 | Zhang |
| 2003/0159999 | A1 | 8/2003 | Oakey et al. |
| 2003/0193984 | A1* | 10/2003 | Ozkan et al. ............... 372/93 |
| 2003/0235924 | A1 | 12/2003 | Adams et al. |
| 2004/0137604 | A1 | 7/2004 | Goodman et al. |
| 2005/0121604 | A1* | 6/2005 | Mueth et al. ............... 250/251 |
| 2005/0158704 | A1* | 7/2005 | Tyvoll et al. ............... 435/4 |
| 2005/0164372 | A1 | 7/2005 | Kibar |
| 2005/0175981 | A1 | 8/2005 | Voldman et al. |
| 2005/0207940 | A1 | 9/2005 | Butler et al. |
| 2006/0091015 | A1 | 5/2006 | Lau |
| 2009/0170186 | A1* | 7/2009 | Wu et al. ............... 435/286.1 |

OTHER PUBLICATIONS

"Engineers create optolelectronic tweezers to round up cells, microparticles", http://www.biologynews.neUarchives/2005/07/20, (Sep. 19, 2005),4 pages.

"Insulator-based dielectrophoretic particle separator and concentrator—iDEP, Selective Particle Concentrator and Sorter for Biomedical and Homeland Security Applications", *Sandia National Laboratories, Fact Sheet*, SANDI#2005-5329,(Aug. 2005,),2 pages.

"Introduction to Antibodies—Flow Cytometry", http://www.chemicon.com/resource/ANT101/a2E.asp, copyright 1998-2005 CHEMICON International,Inc.,6 pages.

"Sandia's dielectrophoresis device may revolutionize sample preparation", *Sandia National Laboratories*, (Aug. 23, 2005),2 pages.

"The Fluorescence-Activated Cell Sorter", http://users.rcn.com/jkimball.ma.ultraneUBiologyPages/F/FACS.html, (Sep. 20, 2005),3 pages.

U.S. Appl. No. 11/552,853, "Office Action mailed Aug. 7, 2009", 21 Pgs.

Arai., et al., "Tying a molecular knot with optical tweezers", *Nature*: vol. 399, (Jun. 3, 1999),pp. 446-448.

Arnold, "Positioning and Levitation Media for the Separation of Biological Cells", *IEEE Transactions on Industry App.*: vol. 37(5), (2001),pp. 1468-1475.

Arnold, et al., "Dielectric measurements on electro-manipulation media", *Biochem. Biophys.Acta.*: vol. 1157, (1993),32-44.

Ashkin, et al., "Optical trapping and manipulation of single cells using infrared laser beams", *Nature*; vol. 330, (Dec. 1987),pp. 769-771.

Carter, et al., "Endocrine-Related Cancer", vol. 11, (2004),pp. 659-687.

Chapman, "Instrumentation for flow cytometry", *Journal of Immunological Methods*: vol. 243, (2000),pp. 3-12.

Chiou, et al., "Cell addressing and trapping using novel optoelectronic tweezers", *IEEE int Conference on Micro Electro Mechanical Systems*, (Jan. 2004),21-24.

Chiou, et al., "Light actuation of liquid by optoelectrowetting", *Sensors and Actuators A 104,,* (2003),pp. 222-228.

Chiou, et al., "Massively parallel manipulation of single cells and microparticles using optical images", *Nature*, vol. 436, (Jul. 2005),pp. 370-372.

Das, et al., "Dielectrophoretic Segregation of Different Human Cell Types on Microscope Slides", *Anal. Chem.*;vol. 77(9), (May 1, 2005),pp. 2708-2719.

Forster, et al., "Use of moving optical gradient fields for analysis of apoptotic cellular responses in a chronic myeloid leukemia cell model", *Analytical Biochemistry*, vol. 327, (2004),pp. 14-22.

Green, et al., "Separation of submicrometer particles using a combination of dielectrophoretic and electrohydrodynamic forces", *Journal of Physics D: Applied Physics*, vol. 31, (1998),L25-L30.

Hagendorn, et al., "Traveling-wave dielectrophoresis of microparticles", *Electrophoresis,*; vol. 12, (1992),pp. 49-54.

Horsman, et al., "Separation of Sperm and Epithelial Cells in a Microfabricated Device: Potential Application to Forensic Analysis of Sexual Assault Evidence", *Anal. Chem.* vol. 77(3), (Feb. 1, 2005),pp. 742-749.

MacDonald, et al., "Microfluidic sorting in an optical lattice", *Nature*, vol. 426, (2003),pp. 421-424.

Ohta, et al., "Manipulation of live red and white blood cells via optoeletronic tweezers", 4 pages.

Pethig, et al., "Development of biofactory-on-a-chip technology using excimer laser micromachiningQ", *Journal of Micromechanics and Microengineering*, vol. 8, (1998),pp. 57-63.

Pohl, et al., *J. Appl. Phys.*, vol. 29, (1958),pp. 1182-1188.

Pohl, H. "Dielectrophoresis, The Behavior of Neutral Matter in Non-uniform Electric Fields", *Cambridge University Press, Chapter 15*, (1978),350-440.

Sakamoto, et al., *Nippon Sanka FUjinka Gakkai Sasshi*, vol. 42(3), (1990),pp. 415-421.

Soo Hoo, et al., "A Novel Method for Detection of Virus-Infected Cells Through Moving Optical Gradient Fields Using Adenovirus as a Model System", *Cytometry Part A 58A*, (2004),pp. 140-146.

Srinivasan, et al., "An integrated digital mocrofluidic lab-on-a-chip for clinical diagnostics on human physiological fluids", *The Royal Society of Chemistry*; vol.4 (May 26, 2004),pp. 310-315.

Stephens, et al., "The dielectrophoresis enrichment of CD34+ cells from peripheral blood stem cell harvests", *Bone Marrow Transplant*; vol. 18(4), (Oct. 1996),777-782.

Straiton, et al., *Gynecol Oncol.*, vol. 17(2), (1984),pp. 185-188.

Talary, et al., "Electromanipulation and separation of cells using traveling electric fields", *J. Phys. D: Appl. Phys.*, vol. 29, (1996),pp. 2198-2203.

Wang, et al., "Cell Separation by Dielectrophoretic Field-flow-fractionation", *Anal. Chem.*, vol. 72(4), (Feb. 15, 2000),pp. 832-839.

Wang, et al., "Microfluidic sorting of mammalian cells by optical force switching", *Nature Biotechnology*, vol. 23(1), (Jan. 2005),pp. 83-87.

\* cited by examiner

DEVICES AND METHODS FOR OPTOELECTRONIC MANIPULATION OF SMALL PARTICLES

RELATED APPLICATIONS

This application is a continuation of U.S. application Ser. No. 11/552,853, filed Oct. 25, 2006, which claims priority to U.S. Provisional Application No. 60/731,123, filed Oct. 27, 2005, the entire contents of which are incorporated by reference herein.

TECHNICAL FIELD

This invention relates to devices and methods for manipulating small particles, such as, for example, micro-particles and/or nano-particles. In particular, this invention relates to devices and methods for manipulating small particles, such as cells, including stem cells, and nucleic acids in solution.

BACKGROUND

Cellular analysis and research often requires the manipulation of small particles, including cells, cell aggregates, cell organelles, stem cells, nucleic acids, bacteria, protozoans, viruses, and/or other micro- and/or nano-particles. Typically, the small particles to be manipulated have a dimension (e.g., diameter) ranging from approximately 0.1 micrometer to approximately several hundred micrometers, for example from approximately 1 micrometer to approximately 100 micrometers, or, for example, from approximately 5 micrometers to approximately 10 micrometers. By way of example only, mammalian cells have a diameter ranging from about 5 micrometers to about 100 micrometers and a lymphocyte may be about 10 micrometers in diameter. In some cases, groups of particles (e.g., cells, stem cells, etc.) may be separated from other particles. The dimension of a group of particles may be as large as about 100 micrometers.

Various devices and methods have been used to manipulate small particles so as to identify, discriminate, sort, characterize, quantitate, observe, move, collect, and/or otherwise manipulate the small particles, such as, for example, live stem cells. For example, microfluidic devices that rely on pressure-driven flow to separate cells, for example sperm cells from epithelial cells, have been utilized. This technique is a passive technique and relatively cost effective for cell sorting, however, the operation protocol is craft sensitive and must be determined on an application by application basis In other words, because microfluidic devices rely on pressure-induced flow to separate cells by virtue of their size and flow rate, appropriate operational conditions must be determined on a trial-and-error basis, since nontarget and target cells may be of substantially the same size. Moreover, due to the relatively narrow microfluidic channels and cross-junctions present in such microfluidic devices, care must be taken to avoid rupturing cells while forcing them through the small passageways.

Flow cytometers, including fluorescence activated sorters, for example, are relatively complex optics-based instruments that serially analyze and isolate fluorescently-labeled cells from a flowing stream of fluid. One such device of this class has been used to manipulate *Escherichia coli* cells. This sorting device comprises a narrow capillary T-shaped junction connected to three reservoirs at each end for receiving aqueous sample, collection, and waste, respectively. The device relies on electro-osmotic flow (EOF) for cell transport and a preset fluorescence threshold to trigger the switching of EOF direction at the T-shaped junction, thereby resulting in cell sorting. A modified version of the device, a microfluidic cell sorting device, has been utilized to sort stably transfected HeLa cells. This modified version relies on pressure-driven flow and a focused laser spot at the junction to deflect and reroute cells by optical force gradient (optophoresis) to a collection reservoir.

The reliance on lasers and other optics contributes to relatively high fabrication costs of some flow cytometers. Further, when using such devices, it may be necessary to simultaneously optimize the optical, fluidic, electronic, and computer systems, and efficiency may be reduced.

Aside from being relatively complex systems and having relatively high fabrication costs, disadvantages of fluorescence activated sorting techniques may include, among others, limited run time due to ion depletion of the sample solution as a result of electro-osmosis and clogging of small orifices and other passageways. Regarding the latter, the size of the orifices at the T-shaped junction are typically relatively small, for example about 3 to about 10 microns. Thus, depending on the types of particles (e.g., cells) being manipulated, some particles may be too large to pass through the junction. Moreover, passive adsorption of proteins and/or other material may occur on the surfaces at the junction, causing a build up of such materials on the surface and potentially result in clogging of the device. Further, if polydimethylsiloxane (PMDS) is used to fabricate a flow cytometer, performing a surface modification on PMDS in order to reduce nonspecific adsorption of biomolecules poses challenges.

Another potential drawback may include the use of dyes to label for recognition various cells of interest. In the case of stem cells, for example, using dyes and other labeling techniques potentially could harm and/or otherwise stress the cells. Similarly, in cases where relatively high intensity lasers are used, such lasers could harm and/or cause stress to the cells. Proliferating potentially stressed cells and possibly implanting the proliferated cells back into a patient could possibly pose potential health and/or other risks. Moreover, the sorting throughput of flow cytometers may be limited in that such devices typically operate on a cell-by-cell manipulation basis. Although, the manipulation of each cell occurs relatively rapidly, due to the cell-by-cell manipulation scheme, the amount of time it may take to manipulate all of the cells in a sample may be relatively large.

Other techniques for manipulating small particles include the use of a dielectrophoretic force. Dielectrophoresis (DEP) refers to the motion imparted on uncharged objects as a result of polarization induced by a spatially nonuniform electric field. An analytical expression of the dielectrophoretic force, $\vec{F}_{DEP}$, acting on a particle (T. B. Jones, Electromechanics of Particles, Cambridge University Press, 1995) is set forth below:

$$\vec{F}_{DEP} = 2\pi r^3 \varepsilon_m \alpha_r \vec{\nabla}(\vec{E}_{RMS}^2),$$

$$\alpha_r \equiv \operatorname{Re}\left(\frac{\varepsilon_p^* - \varepsilon_m^*}{\varepsilon_p^* + 2\varepsilon_m^*}\right)$$

In the above equation, r is the radius of the particle, the factor in parentheses in the first line of the equation is the RMS value of the electric field, and $\alpha_r$ is the real part of the Clausius-Mosotti factor which relates the complex permittivity of the object $\varepsilon_p$ and the complex permittivity of the medium $\varepsilon_m$. The star (*) denotes that the complex permittivity is a complex quantity. The Clausius-Mosotti factor may have any value between 1 and −½, depending on the applied AC frequency and the complex permittivity of the object and medium. If it is less than zero, the dielectric force is negative and the particle moves toward a lower electric field. If the Clausius-Mosotti factor is greater than zero, the dielectric force is positive and the particle moves toward a stronger electric field. In other words, if the object (e.g., particle, cell, etc.) is more polarizable than its surroundings, it may be pulled toward relatively strong field regions ("positive DEP") and if it is less polarizable, it may be pulled toward relatively weak field regions ("negative DEP").

If the particles are charged, then under DC current or low frequency AC current, electrophoresis (EP) occurs, instead of DEP. EP refers to the lateral motion imparted on charged objects in a nonuniform or uniform electric field.

DEP has been used to manipulate particles, such as cells, for example, via a traveling wave generated by a series of patterned electrodes lining up and charged with phase-shifted AC signals. The electrodes can be patterned in an independently controlled array to provide the traveling wave. For examples of such a technique, reference is made to Pethig et al., "Development of biofactory-on-a-chip technology using excimer laser micromachining," *Journal of Micromechanics and Microengineering*, vol. 8, pp. 57-63, 1998, and Green et al., "Separation of submicrometer particles using a combination of dielectrophoretic and electrohydrodynamic forces," *Journal of Physics D: Applied Physics*, vol. 31, L25-L30, 1998. In one technique, disclosed by Das et al., "Dielectrophoretic Segregation of Different Cell Types on Microscope Slides," *Anal. Chem.* May 1, 2005, vol. 77, pp. 2708-2719, incorporated by reference herein, a glass slide is patterned with an electrode array in which the electric field frequency decreases in one direction along the length of the slide, which in turn results in a variation of generated DEP forces along the length of the slide. For other examples of the use of DEP particle manipulation via a traveling wave, reference is made to Hagendorn, et. al., "Traveling-wave dielectrophoresis of microparticles," Electrophoresis, vol. 12, pp. 49-54, 1992 and Talary et al., "Electromanipulation and separation of cells using traveling electric fields," J. Phys. D: Appl. Phys., vol. 29, pp. 2198-2203 (1996), the entire contents of both of which are incorporated by reference herein.

The use of DEP for separating differing cell types in a device wherein electrode arrays are used to create the nonuniform electric field also has been disclosed, for example, in U.S. Pat. No. 6,790,330 B2, which issued on Sep. 14, 2004, U.S. Pat. No. 6,641,708 B1, which issued on Nov. 4, 2003, and U.S. Pat. No. 6,287,832 B1, which issued on Sep. 11, 2001, the entire disclosure of each of which is incorporated by reference herein. These patents disclose various devices and methods relying on DEP induced by electrodes for cell separation.

Another technique for manipulating cells includes the use of optophoresis to manipulate cells in a surrounding medium, such as, for example, an aqueous suspension. Devices and methods utilizing optophoresis rely on a radiation pressure force generated by laser-induced optical gradient fields to capture and manipulate micrometer-scale particles in the aqueous suspension. Devices and methods relying on optophoresis and high intensity lasers to directly trap a single particle have been dubbed "optical tweezers." For exemplary applications utilizing the principles of optical tweezers, reference is made to Ashkin et al., "Optical trapping and manipulation of single cells using infrared laser beams," Nature, vol. 330, December 1987, pages 769-771; and Arai et al, "Tying a molecular knot with optical tweezers," Nature, vol. 399, June 1999, pages 446-448, each of which is incorporated by reference herein.

Aside from the optical tweezers optophoretic technique, another technique employing optophroetic principles uses a fast-scan optophoresis device for recognizing, identifying, and quantifying one type of cells from among others. Such a technique is discussed, for example, in U.S. Application Publication No. 2002/0160470 A1, published Oct. 31, 2002; U.S. Application Publication No. 2005/0164372 A1, published Jul. 28, 2005; Hoo et al., "A Novel Method for Detection of Virus-Infected Cells Through Moving Optical Gradient Fields Using Adenovirus as a Model System," Cytometry Part A, 58A, February 2004, pages 140-146; and Forster et al., "Use of moving optical gradient fields for analysis of apoptotic cellular responses in a chronic myeloid leukemia cell model," Analytical Biochemistry, 327, 2004, pages 14-22, the entire disclosure of each of which is incorporated by reference herein.

In an embodiment, the fast-scan optophoresis device includes a CCD (charge couple device) camera and a coherent Nd-YAG 1064 nm laser beam, operating at 18.3 kW/cm$^2$ at a focused point, scanning across the surface of a thin-layer cell in which a suspension of various types of particles (e.g., cells) are contained. Under a given set of conditions, all of the particles in the suspension are swept across the thin-layer cell by the laser beam until the laser beam's scanning speed reaches a threshold. Above that threshold, one type of particles escapes and is left behind the sweeping laser beam due to various forces, including drag forces, acting on that particle type. Software is used to measure the optophoretic distance that each particle travels and accumulated statistics may be used for identification and quantitation. This device has been used to analyze chronic myeloid leukemia cells and HeLa human ovarian carcinoma cells. Due to the use of high power lasers and focusing optics, manufacturing costs associated with such optophoretic scanning devices may be relatively high. Moreover, the use of high intensity lasers may potentially harm and/or otherwise stress the cells. In the case of stem cells, for example, that may be proliferated after being sorted and collected and then implanted into a patient, there may be a risk associated with such cell stressing.

Another more recently developed particle manipulation technique includes so-called "optoelectronic tweezers," which have been used to attract or expel a plurality of small particles by application of an optically activated DEP force. In contrast to optical tweezers, optoelectronic tweezers can use a low power incoherent light source, for example, on the order of 1 µW/cm$^2$, instead of the high intensity laser used by optical tweezers. By way of example, optoelectronic tweezers may utilize a light source that has a power approximately ten orders of magnitude less than that of the high intensity lasers typically employed in optical tweezers. In the optoelectronic tweezers technique, by projecting the low power incoherent light source onto a photoconductive surface, a liquid suspension containing various particles, e.g., cells, sandwiched between a patternless photoconductive surface and another patternless surface may be subject to a nonuniform electric field resulting from the illumination of the photoconductive layer. In turn, a dielectrophoretic force is created and acts on the particles. Particles may then be attracted by or repelled from the illuminated area depending upon, among other things, the particles' dielectric properties.

One device that employs the above-described principles includes a manipulation chamber comprising a top indium tin oxide transparent glass electrode, a bottom substrate coated with photoconductive material to complete the circuitry, and an aqueous layer containing particles of interest sandwiched between the surfaces. A focused incoherent light spot creates a nonuniform electric field by which the particles (e.g., live cells) in the aqueous sandwiched layer are manipulated based on their respective dielectric constants and sizes.

For further explanation of the operation principles of optoelectronic tweezers, including various devices and techniques employing those principles, reference is made to Pei Yu Chiou et al., "Massively parallel manipulation of single cells and microparticles using optical images," *Nature*, vol. 436:21, July 2005, pages 370-372; PCT publication number WO 2005/100541, entitled "Optoelectronic Tweezers for Microparticle and Cell Manipulation," which claims priority to U.S. Provisional Application No. 60/561,587, filed on Apr. 12, 2004; U.S. application Ser. No. 10/979,645, entitled "Surface Modification For Non-Specific Adsorption Of Biological Material," filed Nov. 1, 2004, in the name of Aldrich Lau; and U.S. Provisional Application No. 60/692,528, entitled "Optoelectronic separation of biomolecules: Separation of dye-labeled DNA, RNA, proteins, lipids, terpenes, and polysaccharides," filed Jun. 30, 2005, in the name of Aldrich Lau, the entire contents of each of which are incorporated by reference herein.

Conventional optoelectronic tweezers are typically employed by providing a manipulation chamber on a microscope stage and targeting predetermined cells of interest. Once the cells of interest are in view, the light source can be mapped onto the manipulation chamber and the predetermined cells can be captured. Thus, the existing devices use previsualization in order to capture known targets of interest.

Based on current techniques for manipulating small particles, including sorting, identifying, characterizing, quantifying, moving and/or otherwise manipulating small particles, it may be desirable to provide a technique for manipulating small particles that is relatively inexpensive to make and/or use and/or is disposable. It may be desirable to provide a manipulation device that is relatively easy to fabricate. For example, it may be desirable to provide a technique that may not require patterned electrodes, microchannels, capillary junctions, capillary orifices, relatively expensive lasers or optics, high power lasers, and/or other elements that are relatively expensive and/or intricate to fabricate. It also may be desirable to provide a device that relies on DEP to manipulate particles and achieves greater flexibility and control over modulation of the electric field than conventional device that utilize patterned electrodes. Moreover, it may be desirable to provide a particle manipulation technique that reduces potential clogging that can occur in device having relatively small junctions and/or orifices through which particles must pass.

Further, it may be desirable to provide a technique that achieves high sorting throughput, purity, and/or the recovery of undamaged (e.g., uncontaminated and/or unstressed) cells. It may further be desirable to provide a technique that achieves the recovery of live, unstressed mammalian cells. For example, it may be desirable to provide a technique that sorts stem cells from other cells, such as mouse feeder cells, and recovers the stem cells uncontaminated and/or unstressed. It also may be desirable to provide a particle manipulation technique that does not require the cells to be chemically labeled and/or exposed to high intensity laser radiation. Although it may be desirable to provide a manipulation technique that does not require chemical (e.g., including dyes and other fluorescence labeling), it also may be desirable to provide a manipulation technique that can work in conjunction with conventional detection methods, including the use of fluorescence signal detection, for example.

It may be desirable to provide a technique that permits visualization of the manipulation (e.g., sorting) of cells via a microscope, a camera, or other visualization tool.

It also may be desirable to provide a technique which selectively sorts cells based on various cell properties, such as, for example dielectric constant and size, and which may be automated. Moreover, it may be desirable to provide a technique that permits surface modification of the device, for example, to alter nonspecific and/or specific adsorption, and/or surface modification of the particles being manipulated. Regarding the former, surface modification of the device may be beneficial to reduce or enhance nonspecific adsorption of, for example, proteins, lipids, cells, and/or other biomolecules. Regarding the latter, it may be desirable to provide a technique that permits reversible surface modification of the particles so as to alter the particles' size, dielectric constant, polarity, and/or other properties.

It may also be desirable to improve upon existing devices that utilize optoelectronic tweezers principles in order to manipulate cells. For example, it may be desirable to provide a device that improves adhesion of the photoconductive and/or electrode layer to the glass substrate, improves robustness, and/or enables operation at a relatively low AC frequency or via direct current. It also may be desirable to reduce nonspecific adsorption of biomolecules. It also may be desirable to provide a device that enables surface modification of the substrates so as to, among other things, reduce nonspecific adsorption and permit the use of surface active agents (e.g., ligands, etc.) to differentiate particles.

Further, it may be desirable to utilize the principles associated with optoelectronic tweezers and/or other optoelectronic manipulation techniques and chambers in conjunction with existing manipulation techniques. In other words, it may be desirable to provide an optoelectronic manipulation chamber as an accessory to a microscope or portable medical device. It may also be desirable to provide a device that utilizes the principles of optoelectronic tweezers in combination with conventional manipulation techniques, such as for example, laser pressure catapulting, laser microdissection, laser microinjection, electroporation, microcapillaries, microdissector, microinjection, micromanipulators, piezoelectric microdissection, drug interaction/cell response, ion channel conductivity measurement (patch clamp), and/or other types of manipulation techniques. To achieve such a combination, it may be desirable to provide an optoelectronic manipulation chamber that permits insertion of an instrument or other external element into the liquid sample cavity containing the particles to be manipulated.

A further desirable aspect may include particle manipulation techniques that may be automated.

SUMMARY

Devices and methods according to exemplary aspects of the present invention may satisfy one or more of the above-mentioned desirable features. Other features and advantages will become apparent from the detailed description which follows.

According to an exemplary aspect, the invention may include the use of low-power optoelectronic tweezer principles in lieu of the high power laser of a fast-scan optophoresis technique. In other words, a scanning low power incoherent light source may be used to optically create a DEP force which acts to entrain some small particles in the scanning light source path or allow other particles to escape from the scanning light source path so as to sort particles.

According to an exemplary aspect of the invention, as embodied and broadly described herein, the invention may include a method for sorting cells in a biological sample comprising a first type of cells and a second type of cells comprising introducing the biological sample into a chamber comprising a first surface and a second surface, wherein the first surface is associated with a transparent electrode and the second surface is associated with a photoconductive portion of an electrode. The method may further comprise moving incident light and the photoconductive portion relative to one another so as to illuminate regions of the photoconductive portion and modulate an electric field in the chamber in proximity to the illuminated regions. The method may further comprise separating the first type of cells from the second type of cells in the chamber via dielectrophoretic movement of the first type of cells and the second type of cells caused by the modulated electric field, wherein a dielectrophoretic characteristic of at least one of the first type of cells and the second type of cells has been modified.

According to yet another exemplary aspect, the invention may include a method for sorting cells in a biological sample comprising a first type of cells and a second type of cells, comprising introducing the biological sample into a chamber having a surface with a photoconductive portion and receiving information that indicates dielectrophoretic movement characteristics of the first type of cells and the second type of cells. The method may further comprise selectively illuminating the surface via incident light based on the information so as to modulate an electric field within the chamber and separate the first type of cells and the second type of cells from each other.

In yet another exemplary aspect, the invention may include a device for manipulating cells in a biological sample, the device comprising a chamber comprising a transparent electrode and a photoconductive portion, wherein the chamber is configured to receive the biological sample, and a light source configured to illuminate the photoconductive portion so as to modulate an electric field within the chamber, the electric field being configured to move the cells via dielectrophoresis. The transparent electrode may comprise a PEGylated transparent electrode.

Yet another exemplary aspect of the invention includes a device for separating cells in a biological sample containing a first type of cells and a second type of cells comprising a chamber comprising a means for generating an electric field in the chamber, the chamber containing the biological sample. The device may further comprise means for illuminating regions of the chamber by imparting relative motion between incident light and the chamber and means for modulating the electric field in the chamber at locations corresponding to the illuminated regions so as to separate the first type of cells and second type of cells from each other by dielectrophoretic movement of the cells.

In the following description, certain aspects and embodiments will become evident. It should be understood that the invention, in its broadest sense, could be practiced without having one or more features of these aspects and embodiments. It should be understood that these aspects and embodiments are merely exemplary and explanatory and are not restrictive of the invention.

BRIEF DESCRIPTION OF DRAWINGS

The drawings of this application illustrate exemplary embodiments of the invention and, together with the description, serve to explain certain principles. In the drawings.

DETAILED DESCRIPTION

Figure 1:
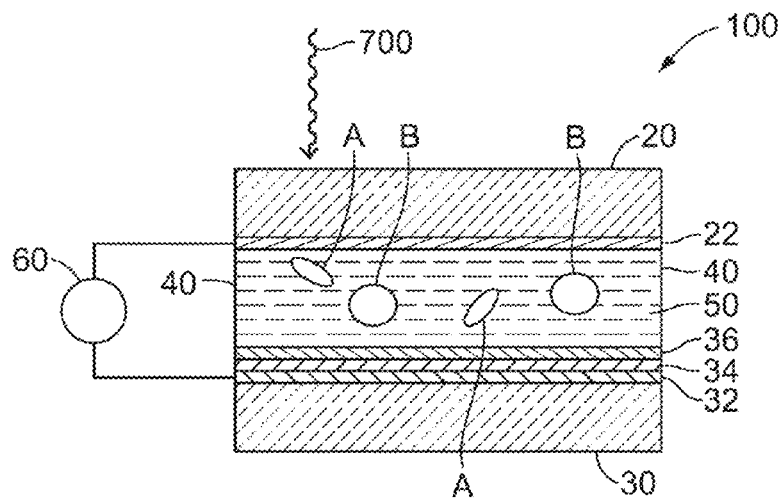
FIG. 1 is a side view of an exemplary embodiment of an optoelectronic manipulation chamber.

FIG. 1 schematically illustrates an exemplary embodiment of a manipulation chamber which relies on optically activated DEP particle manipulation for use in optoelectronic scanning and other manipulation techniques, in accordance with various exemplary aspects of the present invention. The optically activated DEP manipulation chamber also is referred to herein as an optoelectronic manipulation chamber. The chamber 100 may include two substrates, 20 and 30, disposed in a spaced relationship so as to be configured to contain therebetween a sample for analysis. By way of example the substrates 20 and 30 may be spaced from each other by a distance ranging from about 10 microns to about 200 microns. The edges of the substrates may be provided with a seal 40, such as, for example, a gasket (e.g., a rubber gasket such as a silicon rubber gasket, or a fluorinated elastomer (Viton®) gasket), an adhesive (e.g., a pressure sensitive adhesive (PSA)), and/or other sealing mechanisms, so as to contain the sample liquid in the chamber.

The chamber also may be provided with various ports and/or valves (not shown in FIG. 1), for example, input and output ports and/or valves, to allow for introduction of sample or other materials, including manipulation tools, for example, to the chamber, flushing of sample and/or particles from the chamber, and/or collection of particles from the chamber. By way of example, the input and output ports of the chamber may form an interface with instrumentation separate from the chamber via O-rings in a clamping fixture or via resealable elastomeric material, such as, for example, a septum. The septum may permit a needle to pass therethrough for sample addition and/or removal. Instrumentation which may interface with the chamber may include, but is not limited to, valves, such as, for example, pinch or solenoid valves, and/or pumps, such as, for example, a peristaltic pump or a syringe pump for microfluidic control (e.g., sample introduction and collection).

The sample layer 50 may comprise, for example, a liquid suspension containing a plurality of small particles of differing types (for example, differing cell types) labeled A and B in the exemplary embodiment of FIG. 1. It should be understood that the liquid suspension may contain any number of differing types of particles and the use of two particle types A and B herein is for ease of reference and explanation. According to exemplary aspects, the small particles may be suspended in an aqueous medium, such as, for example, a phosphate buffer, a phosphate-buffered saline (PBS), which may contain about 1% bovine serum albumin (BSA), for example, a saline solution having a pH ranging from about 6.5 to about 8.5 and a conductivity ranging from less than about 10 mS/m to several hundred mS/m, a potassium chloride solution, or other suitable mediums, such as mediums that are biologically compatible with cells and iso-osmotic. By way of example, the medium may also comprise a HEPES (N-2-Hydroyxyethylpiperazine-N'-2-ethanesulfonic acid) buffer, sugars, such as sucrose or dextrose, for osmotic stability, and/or solutes for modifying the medium permittivity, such as, for example, ∈-amioncaproic acid.

According to exemplary aspects, the first and second substrates 20 and 30 may be made of a transparent, insulating material, such as, for example, glass, silica, plastic, ceramic, or other suitable transparent and insulating material. Further, in an exemplary aspect, the surfaces of the substrates 20 and 30 facing the chamber interior may be modifiable and/or provided with an adhesive promoter so as to enhance adhesion of the electrode layers thereon. Depending on where the light source is positioned for illuminating the photoconductive material 34, one or both of the substrates 20 or 30 need not be transparent. For example, in the embodiment shown in FIG. 1, wherein the light source is positioned so as to transmit light through the first substrate 20, the second substrate 30 need not be made of a transparent material, and vice versa if the light source is positioned so as to transmit light through the second substrate 30. Those having ordinary skill in the art would recognize a variety of configurations and materials for the first and second substrates, and other elements of the manipulation chamber in accordance with aspects of the invention.

The first substrate 20 may comprise a transparent electrode 22 facing the cavity 50. The second substrate 30 also may comprise an electrode 32, such as, for example a metal electrode. In various alternative embodiments, the substrate 30 adjacent the electrode 32 may be nontransparent and constructed of any material that can withstand the processing conditions for deposition of a photoconductive material. The electrode 22 and the electrode 32 may be electrically coupled to a power supply 60, which may be AC or DC.

In various exemplary embodiments, the transparent electrode 22 may be, for example, gold, indium tin oxide (ITO), or other suitable transparent electrode material. The term "transparent" in this context means that at least some light can pass through the layer. For example, due to a nonuniform deposition of the electrode layer on the substrate, at least some regions may have no electrode deposited thereon or a very thin layer, and light may pass through those regions. In an exemplary aspect, the transparent electrode layer may be such that from approximately 20% to approximately 95% of the incident light may pass through the electrode layer. In an exemplary embodiment, which is described below in more detail, the electrode 22 may be a transparent gold electrode with a PEGylated surface. The term PEGylated refers to a surface that has been processed so as to covalently attach PEG (poly(ethylene glycol)) and/or its derivatives thereto.

The electrode 32 may be a transparent or nontransparent electrode. By way of example, the electrode 32 may be made of indium tin oxide, gold, aluminum, copper, nickel, chromium, a metal alloy, or any other suitable conductive material.

The power supply 60 may be AC or DC. According to various exemplary aspects, an AC current may having a relatively high frequency ranging from approximately 1 kHz to 10 MHz may be used. Alternatively, the AC current may have a relatively low frequency ranging from less than approximately 10 Hz to less than approximately 1 kHz.

A photoconductive material 34 may be provided in a layer over the electrode 32 so as to close the circuit. In an exemplary aspect, the photoconductive material 34 may be separated from the sample layer 50 by a transparent material layer 36, such as, for example, a polymer dielectric, insulating Spin-on-Glass (SOG), a semiconductive SOG, a semiconductive transparent film, a silicon nitride film, a silicon dioxide with a PEGylated surface or other surface-PEGylated layer, a silicon dioxide with surface-grafted poly(acrylamides), any material that exhibits reduced nonspecific adsorption of biomolecules, for example, Teflon-AF® (DuPont), Cytop (Asahi Glass), or fluorinated/perfluorinated polymers, and/or any material capable of being surface-modified so as to reduce nonspecific adsorption of biomolecules. In an exemplary embodiment, which is explained in more detail below, the second substrate 30 may be provided with a PEGylated silicon dioxide photoconductive layer over the metal electrode layer.

A variety of materials may be used for the various elements of the manipulation chamber, and the various layers may be treated (e.g. via surface modification) so as to alter performance of the chamber. By way of example, in various exemplary embodiments, one or more surfaces of the chamber may be subject to a surface modification to either enhance nonspecific adsorption of cells (e.g., using poly-l-lysine may be used to modify the surface) or enhance selective adsorption of particular particle (e.g., cell) types (e.g., using antibodies, lectins, ligands, smart polymers). Further, differing areas on a surface may be subject to differing modifications such that different cell types can bind to the different areas. The materials discussed above are exemplary only and other feasible embodiments of the manipulation chamber can be found in U.S. patent application Ser. No. 10/979,645, incorporated by reference herein. Moreover, in the Example which follows below, an exemplary embodiment of an optoelectronic manipulation chamber, including how to make such a manipulation chamber and various data of interest relating to the chamber, is described in further detail.

Moreover, although in various embodiments described herein, the manipulation chamber is disclosed as comprising approximately planar substrates sandwiching a spacer (e.g., a seal such as PSA), sample liquid, and material layers, it should be understood that various other configurations may be envisioned and are considered within the scope of the invention. In general, any device configuration may be utilized such that a light source illuminating a photoconductive surface generates a nonuniform electric field and a corresponding DEP force on the particle solution within the manipulation device.

In accordance with various exemplary aspects, a scanning light beam 700 may be used to illuminate a portion of the photoconductive material 34 and thereby close the circuit between the transparent electrode 22 and the electrode 32. Transmitting the light onto the photoconductive surface 34 converts the illuminated region of that surface to a virtual electrode, thus generating (e.g., modulating) a nonuniform electric field and corresponding DEP force that acts upon the particles A and B in the sample layer 50. A nonuniform electric field is modulated as a result of the difference in areas of the electrode 22 and the virtual electrode created by the illuminated region of the photoconductive surface 34. Due to the differing dielectric properties and size of each particle type A and B, the differing particle types A and B experience differing forces, including DEP forces, so as to allow manipulation of the particles as is explained further below.

Figure 2A:
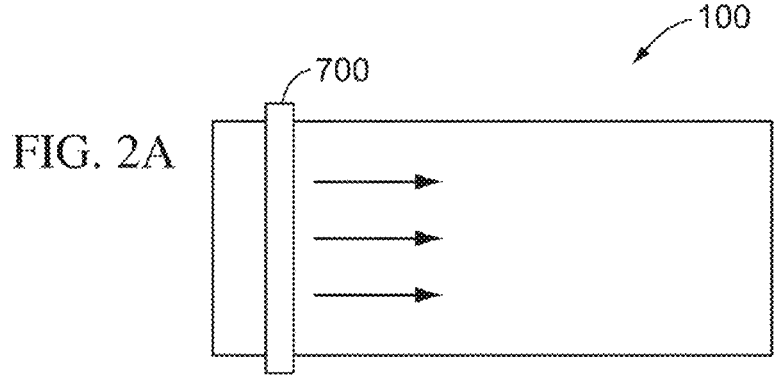
FIG. 2A is a top perspective schematic view of the optoelectronic manipulation chamber of FIG. 1.
Figure 2B:
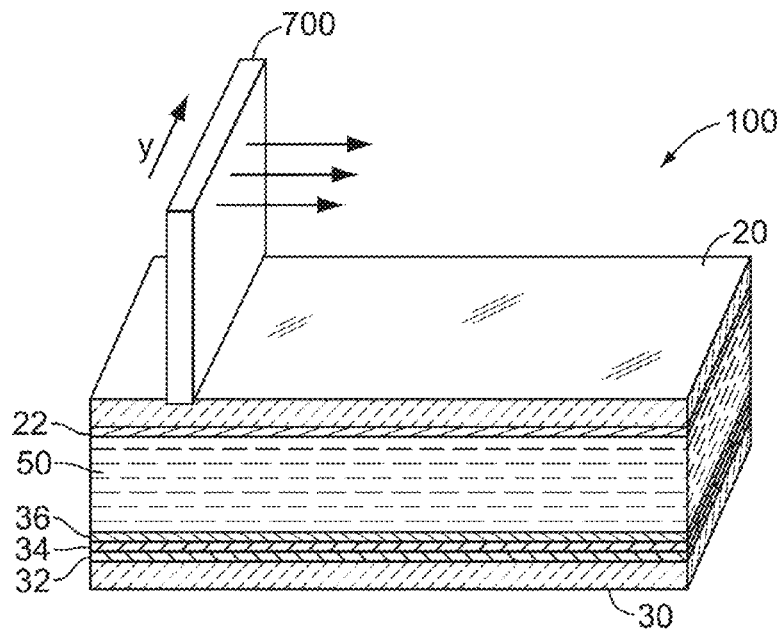
FIG. 2B is a side perspective view of the optoelectronic manipulation chamber of FIG. 1.

FIGS. 2A and 2B schematically illustrate a perspective view and a top view of the optoelectronic scanning assembly according to various aspects of the invention. Referring to FIG. 2A, the manipulation chamber 100, such as, for example, any of the manipulation chamber embodiments in accordance with aspects of the invention, including the manipulation chamber embodiments described with reference to FIG. 1, may be illuminated by a two-dimensional light beam 700. The light beam 700 may extend in a transverse direction to the direction of scanning (shown by the arrows in FIGS. 2A and 2B) of the light beam across the manipulation chamber 100. As discussed above, the light beam may be from an incoherent light source. As the light beam scans across the manipulation chamber 100, a DEP force is created due to illumination of the photoconductive surface and closing of the electrode circuit. That DEP force either attracts or repels the particles (e.g., cells) that are suspended in the liquid layer (e.g., aqueous medium) of the manipulation chamber 100.

Thus, optoelectronic manipulation chambers may use patternless surfaces to generate an electric field gradient. In lieu of patterned electrodes, the patternless surfaces may utilize deposited electrode layers and a photoconductor that completes the circuit via illumination from a light source, thereby creating "virtual", photoactivated electrodes.

A variety of light sources may be used to illuminate manipulation chambers according to aspects of the invention, including but not limited to, lasers, incoherent light sources, light emitting diodes (LEDs). According to various exemplary embodiments, the light source may be an incoherent light source. In various exemplary embodiments, the incident light may range from visible to UV range and may enable visualization through inherent fluorescence characteristics of some particles (e.g., cells). The operating at a power of the incident light may range from about 0.01 $\mu W/cm^2$ to about several hundred $W/cm^2$, for example.

By way of example, other suitable light sources that may be used to illuminate the chamber for various embodiments disclosed herein and in accordance with exemplary aspects of the invention include, but are not limited to, LEDs, phosphor coated LEDs, organic LEDs (OLED), phosphorescent OLEDs (PHOLED), inorganic-organic LEDs, LEDs using quantum dot technology, and LED arrays. Alternatively, suitable light sources may include, but are not limited to, white light sources, halogen lamps (e.g., xenon or mercury arc lamps), lasers, solid state lasers, laser diodes, micro-wire lasers, diode solid state lasers (DSSL), vertical-cavity surface-emitting lasers (VCSEL), thin-film electroluminescent devices (TFELD), filament lamps, arc lamps, gas lamps, and fluorescent tubes. Also by way of example, suitable mechanisms for causing the light source to scan include, but are not limited to, galvanometers and digital light projectors (DLP).

Moreover, by way of example, the footprint of the incident light, such as light beam 700, illuminating the photoconductive surface of an optoelectronic manipulation chamber may be achieved by overlapping several beams of light, for example, rectangular beams or other shaped beams, generated from multiple sources. As an alternative, a single, projecting light source may provide a light projection having, for example, the configuration illustrated in FIGS. 2A and 2B. Those skilled in the art would understand a variety of ways in which to generate incident light footprints of a variety of configurations (patterns), as well as various ways incident light could scan the chamber. Regarding the latter, by way of example only, relative movement may be imparted between the incident light and the chamber, by moving either the chamber, the incident light, or both. As a further example, various independent light sources could be turned on and off to create a scanning of the incident light relative to the chamber.

Figure 28A:
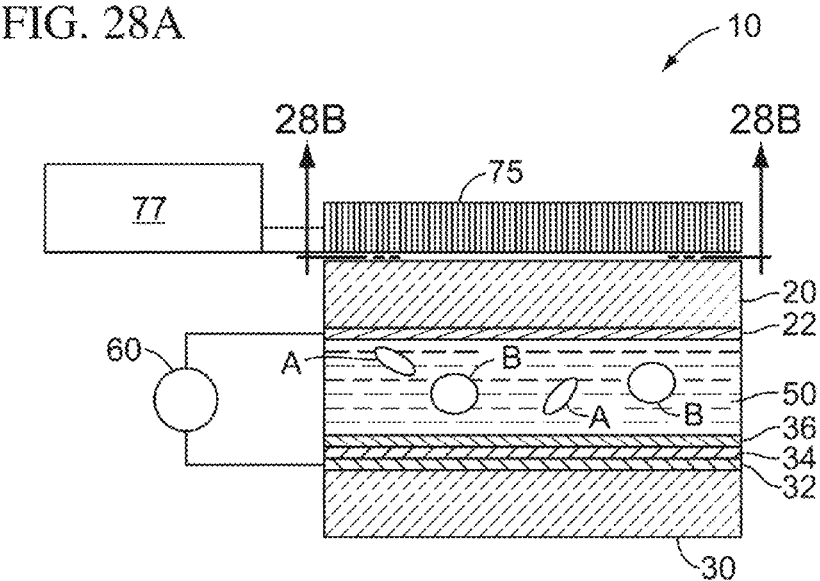
FIG. 28A is a side view of yet another exemplary embodiment of an optoelectronic manipulation chamber.
Figure 28B:
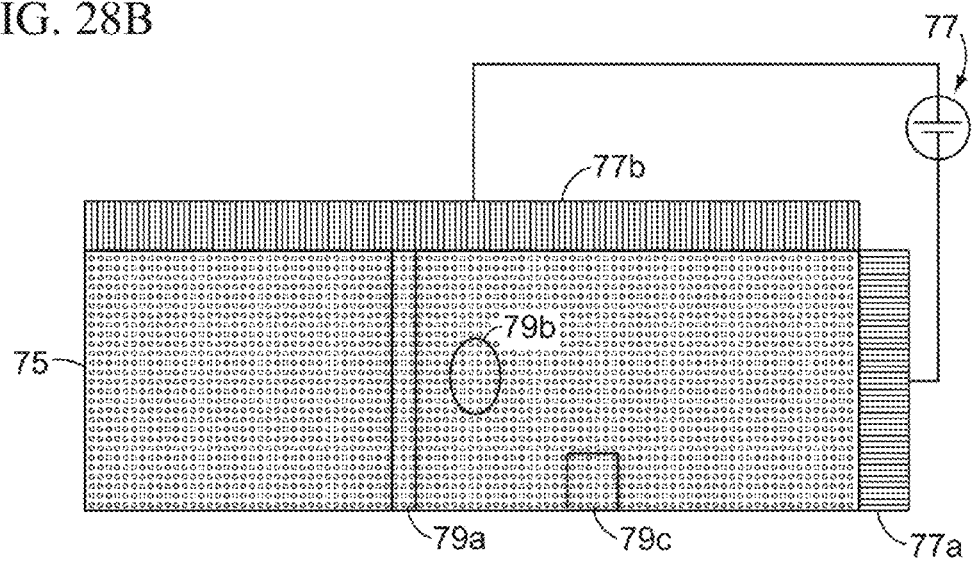
FIG. 28B is a perspective view taken along line 28B-28B of FIG. 28A.

As mentioned above, in various exemplary embodiments, electroluminescence may be used to generate the light for illuminating the photoconductive surface instead of a light source external to the chamber. FIGS. 28A and 28B depict an exemplary embodiment of an optoelectronic chamber wherein an array of electroluminescent material 75 is used as a light source. FIG. 28B shows a plan view of the electroluminescent material from the perspective 28B-28B in FIG. 28A. Those with ordinary skill in the art would understand a variety of arrangements of the electroluminescent light source relative to the chamber in order to illuminate the photoconductive surface and the arrangement shown in FIGS. 28A and 28B should be understood as exemplary and not limiting. The array may be provided in a configuration that permits generation of spatially discrete illumination patterns on the photoconductive surface, thereby permitting the modulation of spatially discrete electric fields within the chamber. According to various exemplary aspects, the electroluminescent layer may be in the form of an array of small LEDs, quantum dots, and/or other arrangements suitable for generating electroluminescent light. By way of example, suitable electroluminescent materials that may be used include, but are not limited to, FLATLITE® and GLOWIRE. The electroluminescent material may be applied via adhesive or other suitable securement mechanisms.

Electronic circuitry 77 may be provided so as to provide an electric current to activate the electroluminescent material in a way that modulates spatially discrete electric fields for DEP movement of particles. As illustrated in FIGS. 28A and 28B, the electronic circuitry may comprise electrical contacts 77a, 77b configured to supply an electric current from a current source to the array 75 of electroluminescent material. Examples of various illumination patterns 79a, 79b, 79c are illustrated in FIG. 28B, however it should be understood that virtually any illumination pattern may be achieved by selectively applying current to the arrayed electroluminescent material. Those having skill in the art would understand how to configure electronic circuitry to apply current to the electroluminescent material so as to achieve the desired illumination patterns on the photoconductive surface. In exemplary aspects, either the same power source used for biasing the electrodes of the manipulation chamber could be used as the power source for the electroluminescent material or a different power source could be used. Modulation of electric fields may be controlled both spatially and temporally as desired by controlling the timing and locations of illumination via the electroluminescent material. By way of example, a scanning of light relative to the photoconductive surface may occur by consecutively activating adjacent rows of the electroluminescent materials.

Using electroluminescence as the mechanism by which to illuminate the photoconductive surface permits the light source to be an integral part of the manipulation chamber (e.g., the electroluminescent array may be applied in a layer adhered to a surface of the chamber) and can achieve scanning and movement of the light relative to the chamber without the need for moving parts (e.g., parts to move either the chamber and/or the light source). Moreover, because light is generated by electric current through the electroluminescent material, flexibility in spatial distribution and/or movement of the photoactivated electric field may be achieved through relatively simple, inexpensive electronic circuitry and signal generation. Electroluminescence also requires relatively low power to generate light, thereby reducing the power consumption of the chamber. Additionally, the wavelength of light may be modulated based on the electroluminescent materials used. It is envisioned that more than one electroluminescent may be used in a manipulation chamber in order to provide greater control over the electric field modulation, for example, at differing locations within the chamber.

In another exemplary embodiment for performing optoelectronic scanning, light patterns may be generated using a programmable scanning mirror, such as, for example, a piezoelectric or galvanometric scanning mirror. Such an approach may be relatively simple in operation and provide opto-mechanical interfacing with conventional upright microscopes. Moreover, as explained further below, the approach may permit isolation of the scanning beam from the epi-fluorescence imaging pathway of a microscope such that scanning and simultaneous collection of multi-color fluorescence cell images may occur. Although optoelectronic scanning may permit markerless particle identification, sorting, and/or collection, the ability to combine optoelectronic scanning with multicolor fluorescence, DEP-signature, and/or cell morphology techniques utilizing integrated instrumentation also may be desirable.

Figure 36:
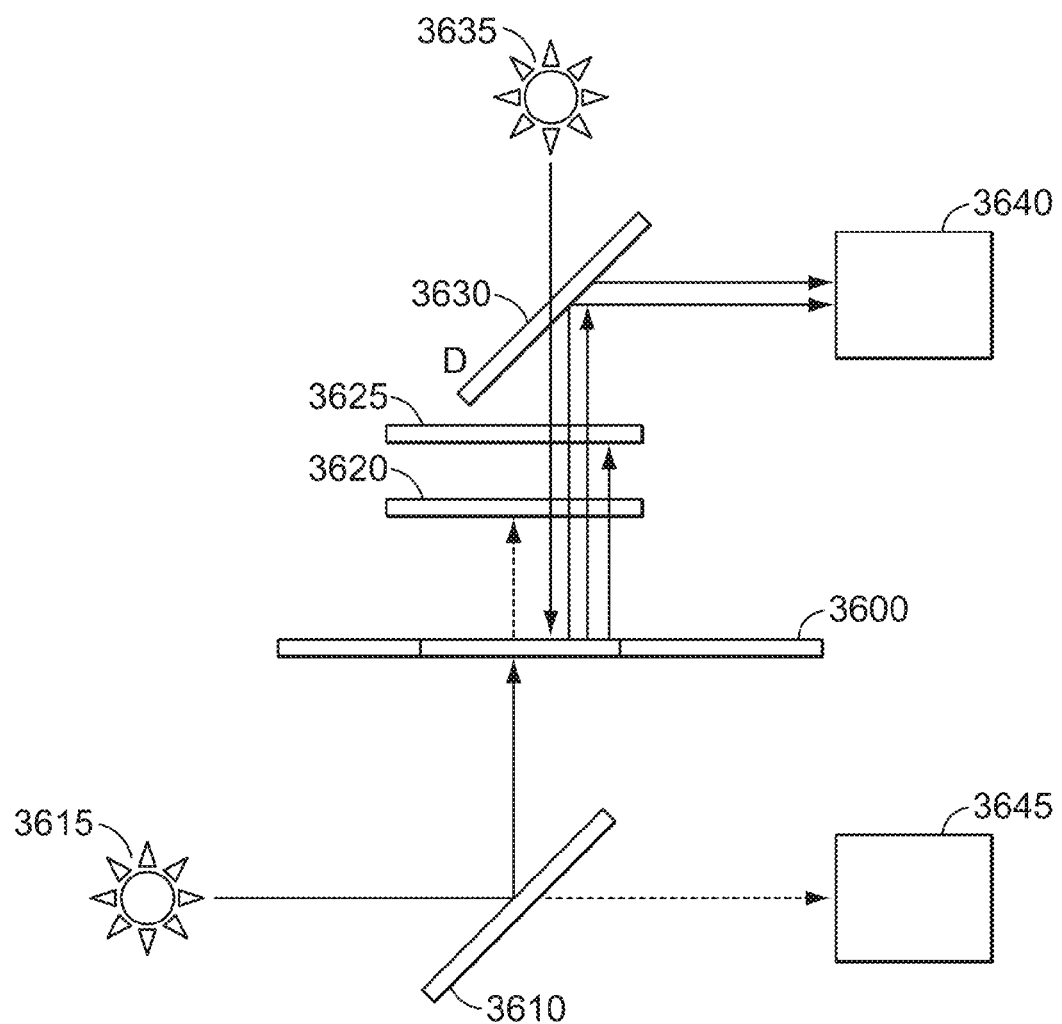
FIG. 36 is an exemplary embodiment of an optoelectronic scanning chamber that utilizes a scanning mirror for illuminating the chamber.

With reference to FIG. 36, a schematic representation of an exemplary embodiment of using a scanning mirror to generate light patterns for optoelectronic scanning and an epi-fluorescence optical pathway for imaging the optoelectronic scanning chamber is illustrated. In FIG. 36, a scanning mirror 3610 is positioned so as to reflect light from a light source 3615 to illuminate an optoelectronic scanning chamber 3600 with patterned light. The optoelectronic scanning chamber 3600 may have a configuration consistent with the teachings herein such that light illuminating a photoconductive portion of the chamber, for example, located on a bottom of the chamber 3600 in FIG. 36, modulates an electric field and creates a DEP force that acts on particles within the chamber. The mirror 3610 may be configured to scan such that the light reflected to illuminate the chamber 3600 moves relative to the chamber 3600 so as to achieve optoelectronic scanning in accordance with the teachings herein. According to various exemplary embodiments, the mirror 3610 may be a piezo-electrically-driven mirror, a galvanometric mirror, and/or other mirrors capable of performing scanning of the light across the chamber 3600, as known to those having skill in the art. In exemplary embodiments, the scanning mirror 3610 may be configured to generate relatively complex light patterns to illuminate the chamber 3600, including movement of light in three dimensions within the chamber. The light source 3615 that transmits light to the mirror 3610 may be from an upright or inverted microscope and may emit light at a wavelength that ranges from about 600 nanometers (nm) to about 700 nm, for example, at about 633 nm.

A series of filters 3620, 3625, and 3630 may be positioned relative to the chamber 3600 so as to provide optical isolation of the scanning light beam fluorescence from an imaging pathway. The filters may include, for example, spectrally-sensitive filters, for example a short pass filter 3620 and a band pass filter 3625, and dichroic filters, for example, a dichroic filter 3630, such that the scanning light is spectrally-isolated from the epifluorescence-imaging pathway. By way of example, filter 3620 may be a 633 nm short pass filter and filter 3625 may be a 500-600 nm band pass filter. In another exemplary embodiment, a notch filter may be used in lieu of the short pass filter 3620. By way of nonlimitative example, the various filters 3620, 3625, and 3635 may be configured to permit the passage of light emitted from particles (e.g., cells) labeled with dyes that are useful in biological and/or other analysis, such as, for example FITC having a peak emission of 525 nm, PE having a peak emission of 568 nm, YoYo1 having a peak emission of 514 nm, tetramethylrhodamine having a peak emission of 546 nm, and DilC18 having a peak emission of 546 nm.

A fluorescence source 3635 may be disposed so as to transmit light through the filters 3620, 3625, and 3630 to the chamber 3600 so as to perform fluorescence detection and analysis of particles in the chamber, as is known to those skilled in the art. By way of example, the fluorescence source may have a wavelength of, for example, between 400-500 nm, for example, 407 nm or 488 nm. Examples of suitable fluorescence sources include, but are not limited to, lasers or arc lamps. Selection of the fluorescence source, and corresponding wavelength, may depend on, among other things, the required peak excitation of the fluorophores (common dyes noted above). The fluorescence detection and/or imaging of the particles may occur via detection through a CCD camera 3640 configured and positioned so as to detect the fluorescence emitted by the particles of interest in the chamber 3600. One or more detectors and/or controllers 3645 may be positioned so as to detect beam alignment and measure the output of the scanning beam 3615 and to control the scanning mirror 3610.

It is envisioned that a conventional microscope may be modified by attaching the various components of the exemplary embodiment of FIG. 36 thereto, thereby providing a relatively simple device for use in providing simultaneous light scanning and detection/imaging of an optoelectronic scanning chamber. In another exemplary arrangement, light could be projected from above the optics of an inverted microscope. For example, a projector could be used as the light source to produce a pattern of light, for example, in the 633-635 nm range, and a lens may be used to demagnify the projected light and transmit the demagnified light image via a mirror to the chamber sitting on a microscope stage. This arrangement utilizes the projector, lens, and mirror to turn light projected from a side of the microscope onto the chamber, for example, at a ninety degree angle and permits viewing of the chamber via the microscope viewing mechanism. In some cases, it is possible to modify a microscope by removing the transmitted light condenser and place the projector and lens on top of the chamber. In such an arrangement, the use of a mirror can be dispensed with. In various exemplary embodiments, the projector may be programmable so as to project a desired light pattern relative to the optoelectronic scanning chamber.

Figure 3A:
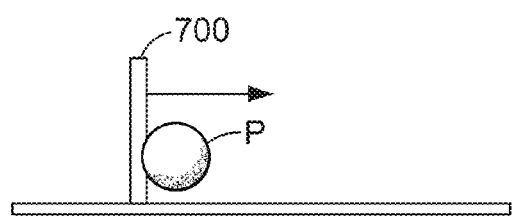
FIG. 3A is an exemplary schematic representation of a light beam scanning across a particle.
Figure 3B:
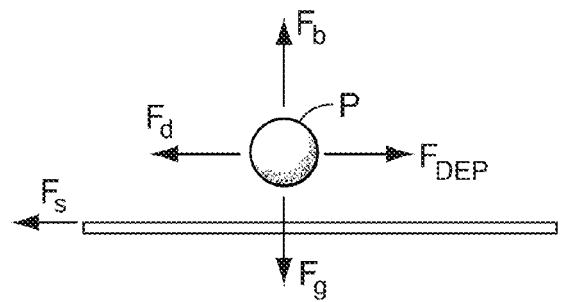
FIG. 3B is a schematic representation of various forces acting on the particle of FIG. 3A in accordance with various exemplary embodiments.

FIG. 3A schematically illustrates a side partial view of an exemplary particle P being scanned by an incident light beam 700 in an optoelectronic manipulation device according to exemplary aspects of the invention. FIG. 3B illustrates a force analysis on the particle P of FIG. 3A as it is subject to and dragged by the DEP force created by the scanning light beam and the manipulation chamber. If the particle P has a positive Clausius-Mosotti value, the particle P is attracted to the relatively strong electric field that occurs proximate the scanning light and if it has a negative Clausius-Mosotti value, it will be repelled by the relatively strong electric field proximate the light beam. In either case, however, the force analysis is the same. As shown in FIG. 3B, as the light beam 700 scans across the manipulation chamber and illuminates the photo-conductive surface, a DEP force is created and acts on the particle P, as shown by the arrow labeled $F_{DEP}$ in FIG. 3B, substantially in the direction of the scanning light. The other forces acting on the particle P simultaneously with the DEP force are gravity $F_g$, buoyancy $F_b$, surface force $F_s$, and viscous drag, $F_d$. Each of these various forces are labeled in FIG. 3B with the direction each force acts being indicated by corresponding arrows.

The relative magnitudes of the various forces described with reference to FIG. 3B depend on factors such as, for example, the characteristics, such as, for example, dielectrophoretic characteristics, of the particle P, the characteristics of the surrounding medium in which the particle is suspended, the intensity of the light beam, and the applied voltage. Thus, the various forces may be controlled, at least to an extent, by selecting suitable mediums, strength of DEP force, scanning speed, and other factors. In addition, by providing various agents and/or other techniques to modify the surface of the particle, the medium in which the particle is suspended, and/or the surfaces of the manipulation chamber, the forces acting on the particles also may be controlled. By way of example only, it may be possible to reversibly modify particles to control whether the particle has a negative DEP force (is repelled by the scanning light source) or a positive DEP force (is attracted by the light source) and/or to modify the strength of the DEP force, for example, by modifying the charge and/or other dielectrophoretic characteristics of a particle. Further, it may be possible to modify the size of the particle by coating or other similar surface modification techniques.

For example, the liquid medium in which a particle of interest is suspended may be selected so as to balance the buoyant force with gravity. When manipulating cells, the medium preferably is iso-osmotic. For low-ionic strength media, a variety of agents, such as, for example, sucrose, mannitol, polysaccharides, and other similar agents, may be used to modify the medium in order so as to provide a relatively electrically neutral medium. Moreover, the surface force may be altered, for example, minimized, by providing a surface coating on one or both of the surfaces in contact with the sample layer in the manipulation chamber. In an exemplary aspect, the wettability of one or both surfaces in contact with the sample layer may be altered so as to make the surface either more or less hydrophilic or hydrophobic.

According to various exemplary aspects, a viscosity enhancer may be added to the liquid medium carrying the particles in order to control (e.g., increase) the viscous drag force acting on the particle P. In various embodiments, the viscous drag forces may be altered by the addition of a viscosity enhancer chosen from neutral, anionic, or cationic enhancers. By way of example, suitable viscosity enhancers may be selected from polymeric materials, including but not limited to, celluloses, such as, for example, hydroxymethy-cellulose and 2-hydroxyethyl cellulose; polysaccharides, such as, for example, chitosan; agar and agarose; ethyleneglycol and its derivatives; homopolymers, such as, for example, polyacrylamide, poly(N,N-dimethylacrylamide), poly(vinyl alcohol), polyoxazoline, poly(N-vinyl pyrrolidone), poly(N-vinylimidazole), poly(4-vinyl pyridine), poly (2-hydroxyethyl(meth)acrylate), poly(vinyl methyl ether), salts of polyaspartic acid; copolymers of the preceding monomeric units; and combinations thereof.

Further, in various exemplary embodiments, the viscosity enhancers may be chosen from inorganic materials, including, but not limited to, fume silica for example. According to yet further exemplary embodiments, the viscosity enhancers may be chosen from organic solvents, including, but not limited to, glycerol, dimethyl sulfoxide (DMSO), and N-methyl-2-pyrrolidone (NMP), and mixtures thereof, for example. In yet further exemplary embodiments, the viscosity enhancers may be chosen from proteins, such as, for example, bone morphogenetic protein (BMP). Those skilled in the art would understand that various viscosity enhancers may be selected and that factors such as, for example, chemical structure, molecular weight, and concentration of an enhancer may alter the viscosity of a particular formulation.

Regardless of the viscosity enhancer that may or may not be used, the viscous drag force acting on a particle being moved through the liquid medium by the DEP force may be expressed by the Stokes Equation in the case of low Reynolds number flow and assuming the particle has a spherical shape, as follows:

$$F_d = 3\pi \mu d V$$

Where $\mu$ is the viscosity of the liquid medium, d is the diameter of the particle, and V is the velocity of the particle. Under a prescribed set of conditions, such as, for example, constant AC voltage, constant frequency, constant intensity of light, etc., the DEP force is a constant force for a given particle type in a given buffer medium. Under the same set of conditions, therefore, the above equation implies that the viscous drag is directly proportional to the velocity of the particle. Thus, at a sufficiently large scanning velocity, the viscous drag may exceed the DEP force, and consequently, the particle will not move at the same speed as the scanning light beam. In other words, the particle is left behind (escapes) the scanning light source.

For a given AC frequency, a given applied voltage, and a given liquid medium, $F_{DEP}$ remains constant, independent of the scanning speed and hence the driven particle velocity. The drag force, $F_d$, however, increases as scanning speed and particle speed increases. Above a threshold velocity, $F_d$ exceeds $F_{DEP}$ and a given particle type is left behind (escapes) the scanning incident light. The threshold velocity differs for differing particle types and depends on the dielectrophoretic property of the particle (e.g., including particle size and dielectric constant (permittivity), as can be seen by the DEP force equation above). For a given particle (e.g., cell) type, the dielectrophoretic property of the particle is determined by the membrane of the cell, including it capacitance, permittivity, conductivity, for example, and size. For a given particle type, therefore, the dielectrophoretic property of the cell is unique and constant.

Figure 4A:
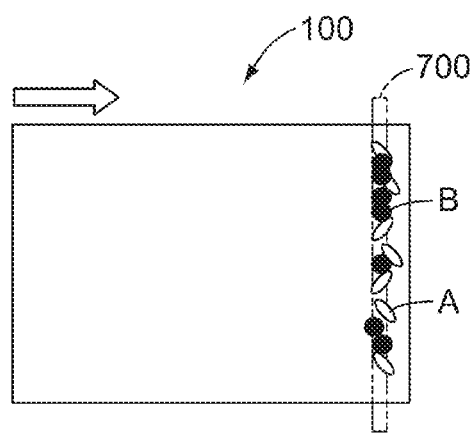
FIGS. 4A-4C are schematic illustrations showing exemplary embodiments of optoelectronic manipulation of particles.
Figure 4B:
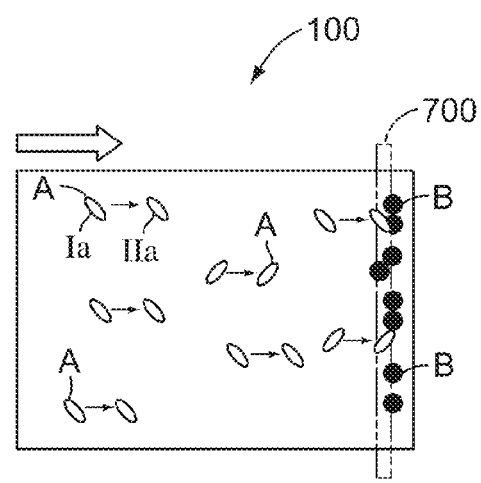
Figure 4C:
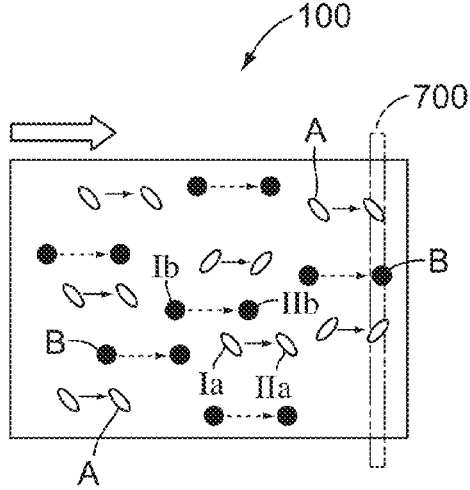

FIGS. 4A-4C illustrate a schematic perspective top view of an exemplary embodiment of optoelectronic scanning for two particle types A and B having positive Clausius-Mosotti factors, which make the particles A and B attracted to the light beam (e.g., positive DEP). FIGS. 4A-4C respectively show the effect on the particles A and B for three different scanning speeds of a light beam 700 across the manipulation chamber in the direction of the large arrows shown in each of the figures.

Referring first to FIG. 4A, a relatively low scanning speed of the light beam 700 is illustrated, with the direction of the scanning light being indicated by the arrow in the figure. As illustrated, at a relatively low scanning speed, both particle types A and B are swept along the length of the manipulation chamber 100 with the scanning light beam. In other words, in FIG. 4A, the DEP force acting on both particle types A and B is greater or equal to the viscous drag force experienced by each of the particle types A and B. Therefore, the particles move across the manipulation chamber in response to the DEP force at a velocity that is approximately equal to the scanning speed of the light beam 700, and thus stay "trapped" in the light beam 700 as it scans across the chamber 100.

The illustration in FIG. 4B shows the effect on the particle types A and B for a medium scanning speed of the light beam 700 across the manipulation chamber. The scanning speed of FIG. 4B is higher than both the scanning speed of FIG. 4A and the threshold speed corresponding to the particle type A, but is at or below the threshold speed corresponding to the particle type B. In this situation, therefore, the particle type A escapes the scanning light beam 700 while the particle type B continues to move along with the scanning light beam, as shown in FIG. 4B. As shown in FIG. 4B, the DEP force created by the scanning light beam 700 continues to move particle type A along the manipulation chamber 100, as illustrated by the displacement between positions Ia and IIa shown for the particle type A.

At the scanning speed illustrated in the exemplary embodiment of FIG. 4C, which is higher than the scanning speeds of FIGS. 4A and 4B, the scanning speed exceeds the respective threshold speeds of particle types A and B. In this case, both particle types A and B are left behind (escape) the scanning light beam 700. However, as shown by the positions Ib and IIb in FIG. 4C, at a given time, the displacement of particle type B is larger than the displacement of particle type A due to the difference in DEP force acting on each particle type A and B, which is a result of the differing dielectric properties and/or size of each particle type. Thus, differing particle types exhibit differing dielectrophoretic movement characteristics based on the particle's dielectric properties and/or size, for example. In other words, the motion imparted as a result of a DEP force differs for differing particle types and therefore different types of particles exhibit unique dielectrophoretic movement characteristics. For example, such dielectrophoretic movement characteristics include the displacement (dielectrophoretic displacement) of a particle type and the speed of manipulation (dielectrophoretic speed) of the particle type as a result of an applied DEP force resulting from a moving incident light relative to the particle type.

It should be noted that in various exemplary embodiments, the scanning velocity may be constant with time, may increase linearly with time, may be a triangular function of time, or may be a square function of time. Those skilled in the art will understand that various waveforms may be used to control the scanning speed as a function of time, and that the particular function used will depend on, among other things, the scanning application.

According to various exemplary embodiments, optoelectronic scanning principles, such as in the manner described with reference to FIGS. 4B and 4C, may be used to perform cell identification and in turn create a database regarding the behavior of differing particle (e.g., cell) types when subject to optoelectronic scanning under predetermined conditions. That is, optoelectronic-driven DEP forces may be studied for various cell types of interest and a functional relationship between the displacement of a cell type and the light beam scanning speed may be determined. Further, the scanning speed at which a cell type can be trapped (e.g., swept along with) and/or the threshold speed at which a cell type escapes the scanning light beam also may be determined. This information may be collected and stored for the purpose of creating a database for use in providing an automated technique to identify, sort, collect, and/or otherwise manipulate various particle types. For example, once information regarding displacement characteristics of a particular cell type has been determined and stored in a database, the identity of that particular cell type in a large population of other cell types can be determined by selecting an appropriate scanning speed and measuring the displacement of the various cell types over a predetermined time period. By matching the measured displacement with the stored displacement characteristics, the particular cell type can be identified.

According to various exemplary aspects, the dielectrophoretic movement characteristics, such as, for example, displacement, of the various particles in the sample layer of a manipulation chamber may be determined by capturing images of the sample in the chamber before, after and/or during scanning using a CCD camera and image processing software. Multiple light scans may be performed on the sample to improve resolution. Speed of the various particles may be another dielectrophoretic movement characteristic that may be measured. As used herein, "dielectrophoretic movement characteristic" may refer to any parameter that may serve to characterize the movement of a particle as a result of dielectrophoresis (e.g., DEP force acting on the particle). Examples of such dielectrophoretic movement characteristics may include speed, displacement, and acceleration, for example.

According to an exemplary embodiment, in order to perform image processing, the manipulation chamber may be placed on a translation stage and a CCD camera (either monochrome or color) may be used to capture images through an optical imaging system, which may be a microscope. Such a system may be configured to magnify the chamber and generate and image. The image could be an image chosen from phase contrast, differential interference contrast, reflectance, light scatter, fluorescence, or other types of images. In an exemplary aspect, the CCD camera may be interfaced with a computer so as to achieve image processing capabilities and to store various data. Software for image processing could include, for example, Universal Imaging Metamorph, Image Pro, or other image processing software. Images also may be captured via a spatially sensitive photodiode.

Using a CCD camera with an objective lens, a field of view, for example, approximately 0.5 mm×0.5 mm can be generated, and either brightfield or darkfield illumination may be used. By moving the translation stage while the CCD camera remains stationary, or vice versa, images of multiple locations of the manipulation chamber can be captured and processed.

It is contemplated that in addition to capturing still images of the manipulation chamber at various snapshots in time during the scanning process, real-time moving images also may be taken.

Aside from utilizing optoelectronic scanning to identify the presence of particular particle types from among other particle types in a sample, optoelectronic scanning may be used to sort and collect particle types. In an exemplary aspect, the sorting and collecting steps may follow an identification step. FIGS. 5A-5C, FIGS. 6A-6C, and 7A-7C depict various exemplary embodiments of utilizing optoelectronic manipulation principles (e.g., including optoelectronic scanning) to sort and collect particle types.

Figure 5A:
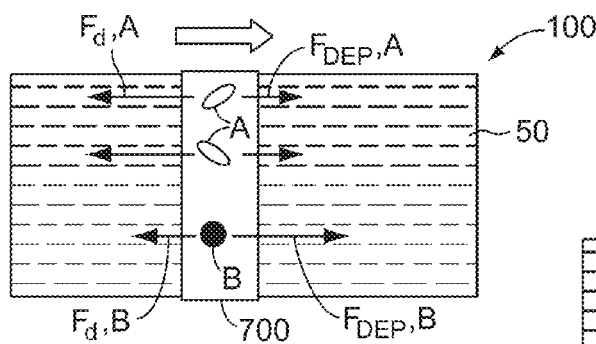
FIGS. 5A-5C are schematic illustrations showing another exemplary embodiment of optoelectronic manipulation of particles.
Figure 5B:
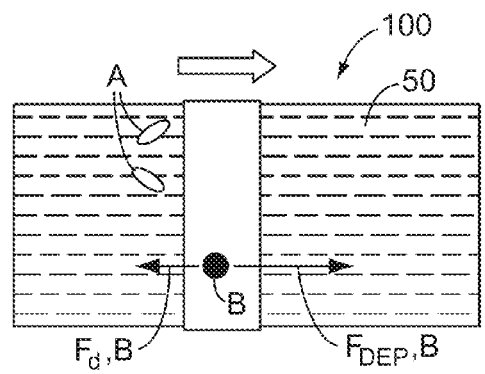
Figure 5C:
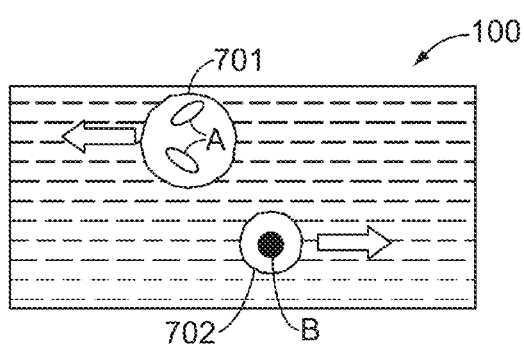

FIGS. 5A-5C schematically illustrate an exemplary embodiment for sorting two differing particle types A and B contained in a suspension 50, with both particle types A and B having positive Clausius-Mosotti values such that both are attracted to the scanning light beam 700. In the exemplary embodiment of FIGS. 5A-5C, due to the dielectrophoretic properties of each particle type, at a given velocity, particle type A has a relatively small DEP force $F_{DEP,A}$ and a relatively large drag force $F_{d,A}$ acting on it, whereas particle type B has a relatively large DEP force $F_{DEP,B}$ and a relatively small drag force $F_{d,B}$ acting on it. As indicated in the equations above, for a given particle type, the DEP force remains constant, while the drag force may change based on the speed of the particle (e.g., the speed of the particle as it is moved by the DEP force).

FIG. 5A illustrates a portion of the scanning mode (e.g., time=0) when, due to the speed of scanning which has not yet exceeded the threshold velocity of either particle type, both particle types A and B are attracted to the stationary light beam and are thus trapped within the light beam. As the light beam reaches above a threshold scanning speed corresponding to particle type A, which speed may be predetermined, for example, based on previously gathered and stored displacement/scanning speed relationships, particle type A escapes the scanning light beam 700 and is left behind while particle type B remains trapped and swept along with the scanning light beam 700. FIG. 5B illustrates a snapshot of the scanning assembly at a time after the light beam has reached the threshold scanning speed at which particle type A escapes the light beam 700.

Following the trapping of one or more particles of particle type A, a collection scheme, for example, as illustrated in the exemplary embodiment of FIG. 5C may be utilized to sort the particles and collect them for further processing, manipulation, and/or disposal. According to various exemplary embodiments, a collection scheme may include illuminating the sorted particles, e.g., types A and B, with separate beams of light (e.g., footprints of focused light which may have a solid circular or other configuration) focused so as to respectively trap one or more particles of particle type A and one or more particles of particle type B, for example. Although FIGS. 5A-5C show two differing particle types, it should be understood that several differing particle types may be present and sorted. The segregated particle types trapped respectively by the focused light beams 701 and 702 can now be moved out of the scanning assembly to collection reservoirs or other desirable locations by moving each light beam 701 and 702 at a speed such that the particle types A and B remain trapped by the light beams 701 and 702, respectively.

Figure 6A:
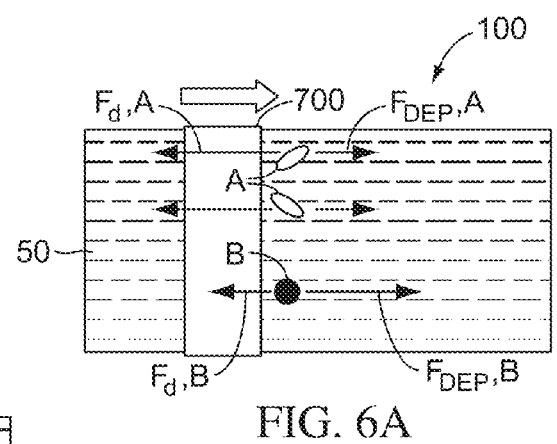
FIGS. 6A-6C are schematic illustrations showing yet another exemplary embodiment of optoelectronic manipulation of particles.
Figure 6B:
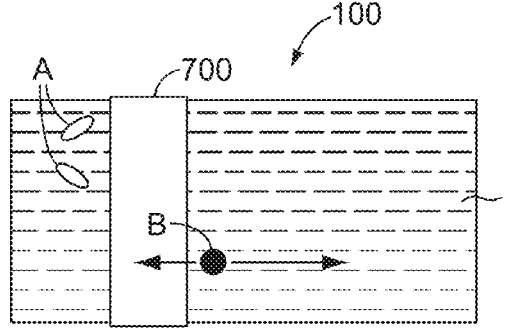
Figure 6C:
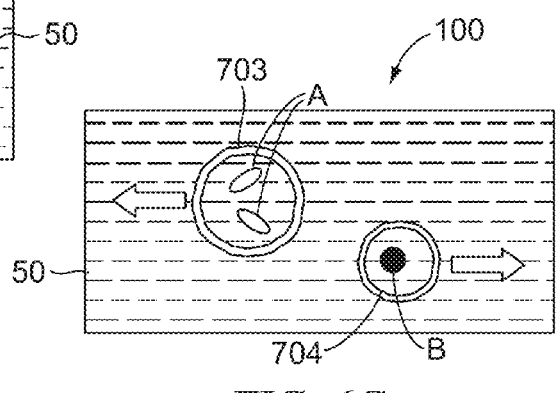

Another exemplary embodiment of a sorting and collection scheme that may be useful in manipulating particles having negative Clausius-Mosotti values, leading to a negative DEP force which causes the particles to be repelled by a light source and the electric filed generated by it, is illustrated schematically in FIGS. 6A-6C. In this exemplary embodiment, particles of particle type A and particle type B have negative Clausius-Mosotti values and thus during a portion of the scanning mode, such as the start of the scanning mode (e.g., time=0) when the scanning speed of the light source has not reached the threshold speed corresponding to either particle type A or B, as illustrated in FIG. 6A, both particle types are repelled by the scanning light beam 700 and the DEP force acts to move the particles A and B in a direction away from the scanning light beam 700.

Due to differences in their respective dielectrophoretic properties (e.g., size and dielectric constant), particle type A is influenced by a relatively large drag force $F_{d,A}$ and a relatively small DEP force $F_{DEP,A}$, whereas particle type B is under the action of a relatively small DEP force $F_{DEP,B}$ and a relatively large drag force $F_{d,B}$. The scanning speed of the light beam 700 can be adjusted such that it is above the threshold velocity of particle type A, thereby causing the drag force acting on the particle type A to become larger than the DEP force acting on that particle type so that at a later time (e.g., time=t) during scanning particle type A is left behind the scanning light beam 700 (e.g., particles of particle type A escape the scanning light source). On the other hand, the scanning speed is selected such that it is below the threshold speed corresponding to particle type B such that the DEP force acting on particle type B continues to be larger than the drag force acting on that particle type. In this case, particle type B continues to be expelled from the light source and thus particles of particle type A and particle type B are separated from one another (e.g., divided by the light beam 700), as shown in FIG. 6B.

As discussed above with reference to FIGS. 5A-5C, the scanning speed of the light beam 700 in the exemplary embodiments of FIGS. 6A-6C may be predetermined based on information known about the varying particle types that are being scanned. By way of example, the scanning speed sufficient to separate particle type A from particle type B, as shown in FIG. 6B for example, may be predetermined based on information collected during an optoelectronic scanning identification process such as that described with reference to FIGS. 4A-4C, for example.

Once the differing particle types A and B have been separated, as illustrated in FIG. 5B, each particle type may be collected or otherwise manipulated separately from the other particle type. By way of example, FIG. 6C illustrates an exemplary embodiment of a collection scheme that may be used to collect one or more particles of particle type A for further processing and/or manipulation and to collect one or more particles of particle type B for further processing and/or manipulation. It should be understood that the collection of the particles may include removing the particles from the manipulation chamber 100.

As discussed above, both particle types A and B in the exemplary embodiment of FIGS. 6A-6C have negative Clausius-Mosotti values. By encircling each of the segregated particle types A and B with separate light beams 703 and 704 focused into ring-like configurations, the particles of each particle type A and B become trapped within the respective light rings 703 and 704 due to the negative DEP, repelling force acting on them. Once trapped within each ring of light 703 and 704, the differing particle types A and B may be moved to different collection reservoirs or other locations by moving the light rings 703 and 704 at a speed such that the respective particle types A and B trapped therein are not able to escape.

In various exemplary embodiments, optoelectronic scanning also may be employed to separate and/or otherwise manipulate particle types of both positive and negative Clausius-Mosotti values contained in the same sample layer. By way of example, FIGS. 7A-7D schematically illustrate an exemplary embodiment of using optoelectronic scanning to identify and sort particles in a sample containing at least a first particle type having a positive Clausius-Mosotti value and at least a second particle type having a negative Clausius-Mosotti value. In the exemplary embodiment of FIGS. 7A-7D, particle type A has a positive Clausius-Mosotti value and particle type B has a negative Clausius-Mosotti value.

Figure 7A:
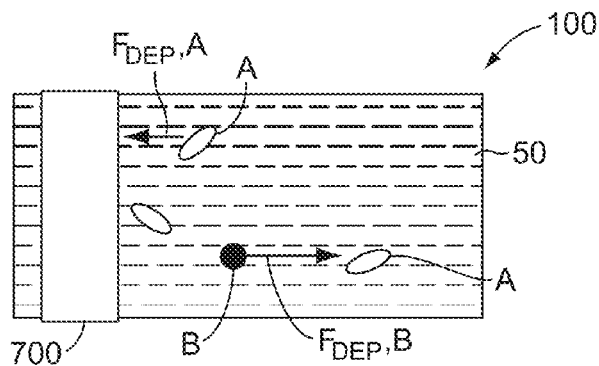
FIGS. 7A-7D are schematic illustrations showing yet another exemplary embodiment of optoelectronic manipulation of particles.

As scanning begins and the light beam 700 scans the manipulation chamber 100 so as to be moved toward the particles A and B shown in FIG. 7A, particles of particle type A will be attracted to the scanning light beam 700 due to their positive Clausius-Mosotti values. In contrast, particles of particle type B will be repelled by the scanning light beam 700. FIG. 7A illustrates an exemplary snapshot of the manipulation chamber 100 at the beginning of scanning, wherein the DEP forces $F_{DEP,A}$ and $F_{DEP,B}$ are shown acting on each particle type A and B. As shown in FIG. 7A, $F_{DEP,A}$ acts in a direction to move particle type A toward the light beam 700 and $F_{DEP,B}$ acts in a direction to move particle type B away from the light beam 700.

Figure 7B:
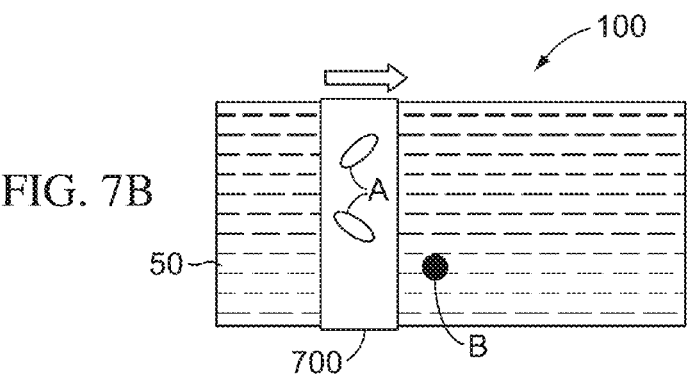

Due to the attraction of particle type A toward the light beam 700, at a later time during the scanning process and with the scanning speed of the light being controlled, particles of particle type A become captured by (e.g., trapped in) the light beam 700 and move along with that incident light 700 as it scans across the manipulation chamber 100 in the direction shown by the arrow in FIG. 7B. Assuming the scanning speed does not exceed particle type A's threshold velocity, more and more particles of particle type A will become trapped by the light beam 700 as it scans across such particles during its travel across the manipulation chamber 100. At the same time, particles of particle type B continue to be repelled by the light beam 700 and therefore move along the manipulation chamber 100 ahead of the scanning light beam 700, also in the direction of the arrow shown in FIG. 7B.

Figure 7C:
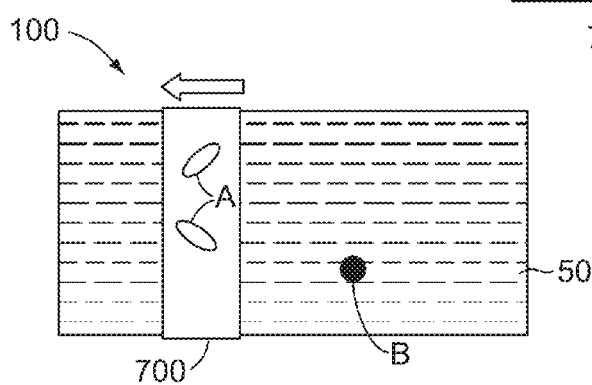

Once the scanning light beam 700 is swept across the manipulation chamber 100, the direction of scanning of the light beam 700 relative to the chamber may be reversed such that the light beam 700 scans in the direction shown in FIG. 7C. By scanning in the reverse direction, separation of particle type A and particle type B may be improved by further separating (e.g., increasing the distance between) particle type A particles from particle type B particles. That is, particle type B, which is repelled by the light, may remain at its position prior to the reverse scanning, which may be at the right hand side of the chamber if the light beam 700 scans across the entire chamber in the direction shown in FIG. 7B. Particle type A, on the other hand, will continue to be attracted by the light beam 700 during the reverse scan shown in FIG. 7C, and thus further separation between particle type A and particle type B may be achieved.

Figure 7D:
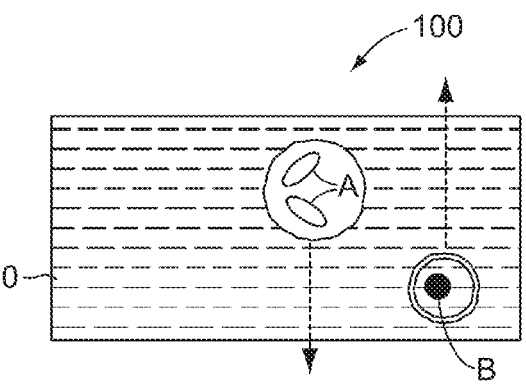

Once the desired separation between particle types A and B is achieved and/or at some time after reverse scanning of the light beam 700, the scanning mode may be stopped and focused light beams used to independently move particles of particle type A and particles of particle type B, for example, to collection reservoirs or the like. As illustrated in FIG. 7D, a focused light beam having a solid circular configuration may be used to collect particles of particle type A having a positive Clausius-Mosotti value. A focused light beam having a ring-like configuration can be used to encircle and collect particles of particle type B having a negative Clausius-Mosotti value.

It should be understood that the number of scanning iterations, including reverse scanning, of FIGS. 5-7 can occur numerous times as needed to achieve desired separation of particles. Further, the reverse scanning step of the exemplary embodiment of FIG. 7 could occur numerous times during the scanning process. In other words, the reverse scanning can take place at any point during the scanning of the manipulation chamber and need not occur only once the light has scanned the entire chamber in one direction. Moreover, the speed of forward and reverse scanning may vary independently with time during the course of scanning.

It should be understood that in the exemplary embodiments described herein, any number of particles of each particle type may be in the sample layer introduced into the manipulation chamber and may be separated from the other particle types and collected, and that the number of each particle types illustrated in the figures is exemplary only. Further, it also should be understood that the exemplary embodiments could be used to separate and/or collect more than two differing particle types and that the use of two particle types A and B is for ease of reference and explanation. Moreover, a variety of focused light configurations, other than rings or solid circles, for example, may be used to move the sorted particles to respective collection reservoirs. And it is envisioned that groups (e.g., clusters) of trapped particles may be moved together via a focused light beam.

Also, in the description of FIGS. 5-7 and otherwise herein, when incident light is referred to as moving (e.g., scanning or otherwise) relative to the chamber, it should be understood that such moving is intended to imply relative movement between the incident light and the chamber. It is envisioned that such relative movement may be achieved by moving the light while the chamber remains stationary, moving the chamber while the light remains stationary, moving both the chamber and the light source, or independently illuminating a plurality of stationary light sources configured in an array so as to achieve movement of incident light relative to the chamber. It also should be understood that the velocity of the relative movement of incident light relative to the chamber (e.g., the scanning speed) may be varied as a function of time.

Figure 8:
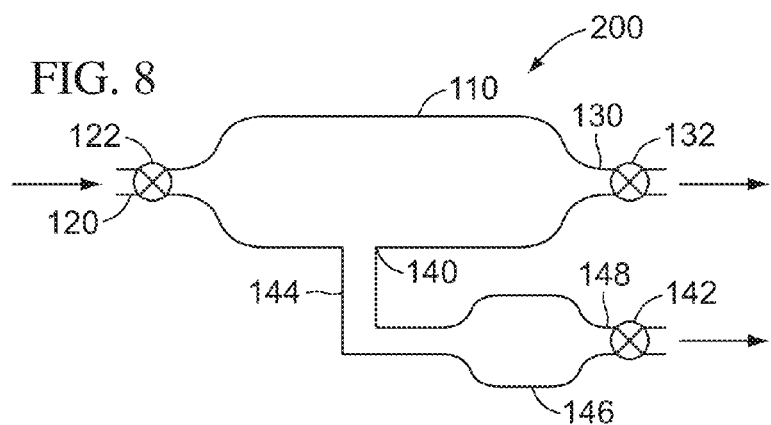
FIG. 8 is a schematic top view of an exemplary embodiment of a particle sorting device.

FIG. 8 schematically illustrates an exemplary embodiment of a device that may be used to identify particles of interest (e.g., target particles) in a sample containing a plurality of differing particle types and to separate and collect those particles of interest utilizing the principles of optoelectronic manipulation (e.g., optoelectronic scanning) described herein. As shown in FIG. 8, an exemplary optoelectronic identification and sorting device 200 may comprise an optoelectronic manipulation chamber 110 comprising an inlet 120 and at least two outlets 130, 140. A first outlet 130 may lead, for example, to a waste collection region in flow communication with the manipulation chamber 110 and a second outlet 140 may lead to a channel 144 configured to collect the target particles from the manipulation chamber 110. The channel 144 may be in flow communication with a collection reservoir 146 configured for collecting one or more target particles after those particles are moved from the manipulation chamber 110 and through the collection channel 144. A third outlet 148 may be provided in flow communication with the collection reservoir 146 to pass the collected target particles from the optoelectronic sorting device 200 to other instrumentation and/or locations for further processing and/or other manipulation of the collected target particles.

One or more of the various inlets and outlets may be associated with valves, for example, microfluidic valves 122, 132, and 142, so as to control flow through those inlets and outlets. Although the valves 122, 132, and 142 of FIG. 8 are shown as being placed within the sorting device 200, it should be understood that one or more of the valves could be placed outside of the device 200 in conjunction with other instrumentation, such as, for example, reservoirs, pumps, including microfluidic pumps, or other instrumentation for feeding sample to the device 200 and/or for removing sample and/or cells from the device 200.

Figure 9A:
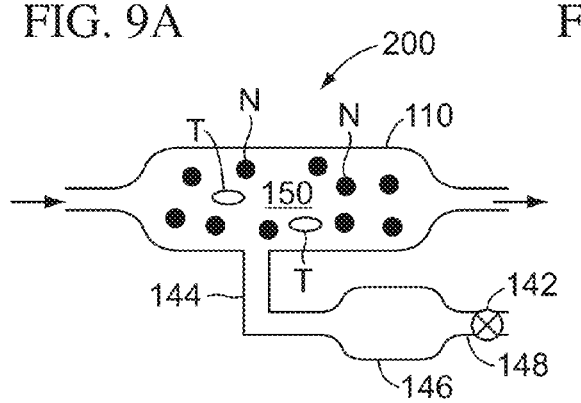
FIGS. 9A-9H are schematic illustrations of an exemplary embodiment of the use of the device of FIG. 8.
Figure 9B:
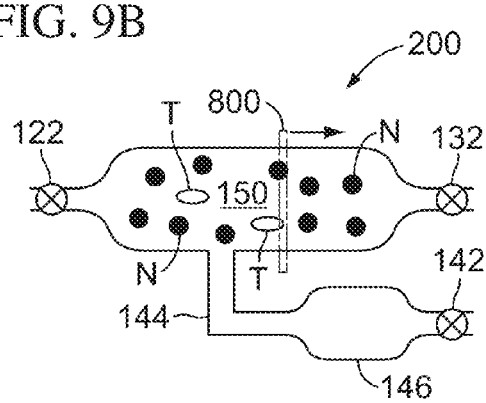

According to various exemplary embodiments, exemplary steps for using the device 200 of FIG. 8 to identify and sort particles of interest are shown in FIGS. 9A-9H. In FIGS. 9A-9H, the particles that are desired to be collected are referred to as target particles and are labeled T. The other particles in the sample are referred to as nontarget particles and are labeled N. To begin, as depicted in FIG. 9A, valves 122 and 132 are open, while valve 142 remains closed. A sample 150, such as a suspension containing target particles T and nontarget particles N is introduced into the chamber 110. By way of example, a microfluidic pump (not shown) may be placed in flow communication with the chamber 110 in order to supply the sample 150 to the chamber 110. Once the chamber 110 has been filled with the sample 150, valves 122 and 132 are closed and an elongated light beam 800 (e.g., a light beam that spans the width of the chamber) scans across the chamber 110 in the direction of the arrow, as shown in FIG. 9B.

In the exemplary step of FIG. 9B, the target particles T contained in the sample 150 within the chamber 110 are identified, for example, in accordance with the exemplary embodiment for particle identification described with reference to FIG. 4C. According to various exemplary aspects, the cell identification step of FIG. 9B may occur by using image processing software and a CCD camera, for example, to take a snapshot of the particles in the chamber 110 before and after scanning. Based on information regarding the dielectrophoretic movement characteristics (e.g., displacement) that various particle types exhibit in response to predetermined light beam scanning speeds and other operational parameters of the chamber 110, the target particles T may be identified by comparing measured information resulting from the scanning step of FIG. 9B with stored information or otherwise known information.

After the target particles T in the manipulation chamber 110 have been identified in the exemplary identification step of FIG. 9B, the scanning light beam may be turned off and focused light sources 810 may be illuminated on the identified target particles T. By way of example, a focused ring of light like that described with reference to FIG. 6C may be used if the target particles T have a negative Clausius-Mosotti value. Alternatively, a focused solid circle of light like that described with reference to FIG. 5C may be used if the target particles T have a positive Clausius-Mosotti value.

Figure 9C:
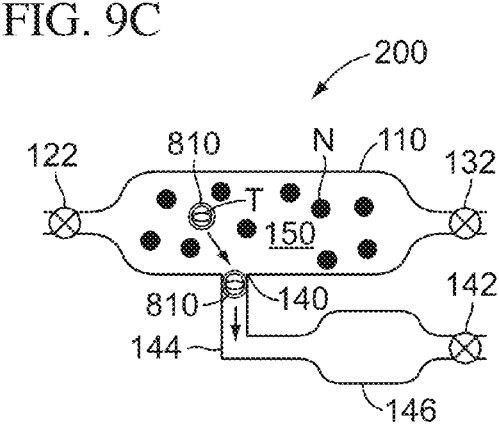
Figure 9D:
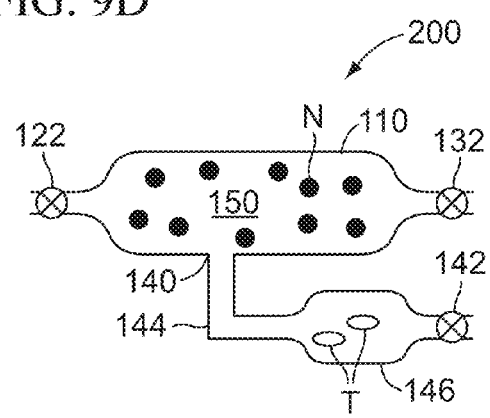
Figure 9E:
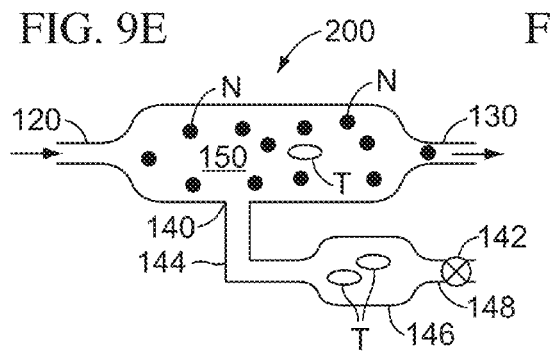

The focused light sources 810 may then be moved so as to route the target particles T through the outlet 140 and collection channel 144 and into the collection reservoir 144, as illustrated in FIGS. 9C and 9D.

Figure 9F:
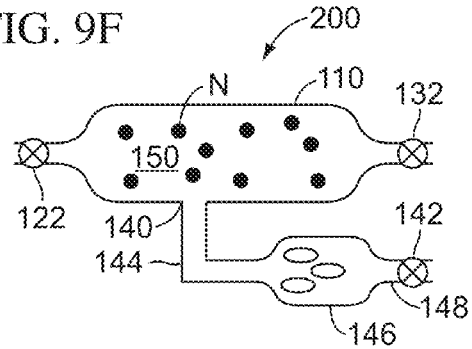

According to various exemplary embodiments, additional identification and sorting steps may be performed as desired. For example, if additional sorting is desired, valves 122 and 132 may again be opened and a new sample containing target particles T and nontarget particles N may be introduced into the manipulation chamber 110, as illustrated in the exemplary embodiment of FIG. 9E. As described with reference to FIGS. 9B-9D, the valves 122 and 132 may be closed, optoelectronic scanning may be performed to identify target particles T in the manipulation chamber 110, and then focused light sources 810 may be used to illuminate the target particles T and move those additional target particles T through the channel 144 and into the collection reservoir 146, as shown in FIG. 9F.

Figure 9G:
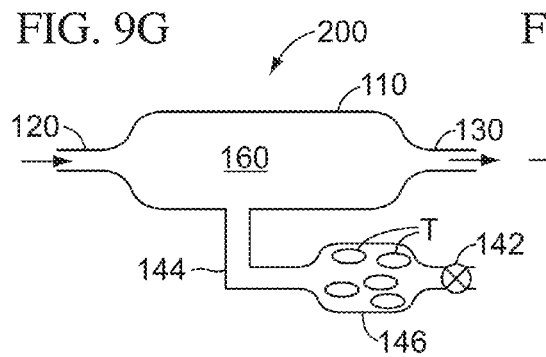

Once the desired number of target particles T have been collected in the collection reservoir 146 and/or the desired number of identification/sorting/collection iterations have been performed, valves 122 and 132 may again be opened and the manipulation chamber 110 may be cleared of the sample 150. According to various exemplary embodiments, and as shown in FIG. 9G, the manipulation chamber 110 may be washed by flushing the chamber with a medium 160. The medium may be the same as the medium used to suspend the cells. Other mediums may also be used, for example, buffer solutions, such as a phosphate buffer saline containing 1% BSA, that are compatible with the cells may be used.

Figure 9H:
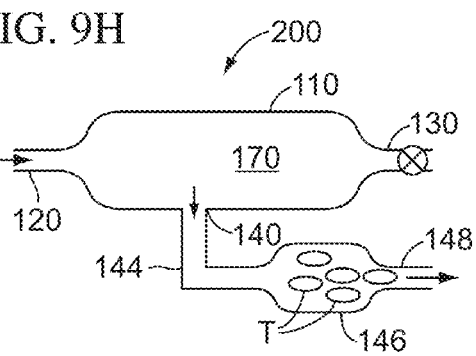

After the manipulation chamber has been flushed, valve 132 may be closed while valves 122 and 142 are opened, as shown in FIG. 9H. The target cells T in the reservoir 146 may be moved from the collection reservoir 144 and the sorting device 200 through outlet 148 to another location and/or instrumentation for further processing and the like of the target particles T. To remove the target cells T, an aqueous medium 170 (e.g., a solution or a solvent) may be introduced into the chamber 110 and drawn through the channel 144 and collection reservoir 146 to suspend the target particles T and remove them from the sorting device 200. A microfluidic pump or other device suitable for removing the target particles T may be placed in flow communication with the sorting device 200 to accomplish removal of the target particles T from the device. Media that may be suitable to flush the chamber include, but are not limited to, the same media that may be used to prepare the suspension of the particles. Thus, suitable media include buffers, such as, for example, phosphate buffers, phosphate buffer salines (which may contain 1% BSA), a solution of sodium- or potassium-chloride, or other buffers. The flushing medium also may in the form of an organic solvent, for example, a solution of ethanol or acetonitrile. As a further example, if the target particles T are cells that may be used and propagated after collection, e.g., stem cells, it may be desirable to use a cell growth medium, such as, for example, Eagle's, RPMI, Fischer's, Ham's F10, or other suitable cell growth media, to remove and collect the target particles T.

Figure 10A:
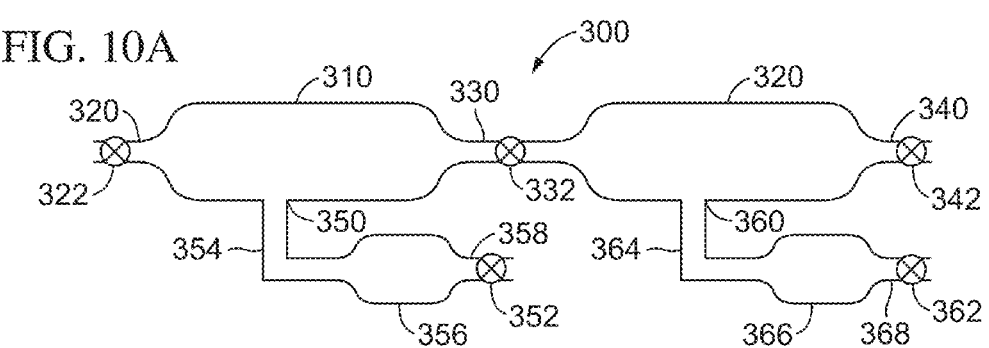
FIGS. 10A-10B are schematic illustrations of yet another exemplary embodiment of a particle sorting device.
Figure 10B:
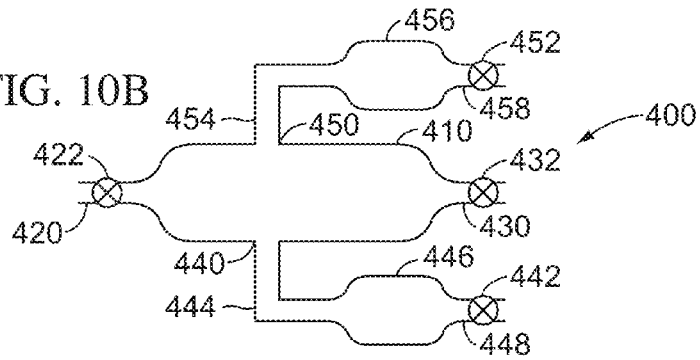

With reference to FIGS. 10A and 10B, two exemplary embodiments of a multi-manipulation chamber sorting device are illustrated. The multi-chamber sorting devices of FIGS. 10A and 10B may be used, in a manner similar to that described with reference to FIGS. 9A-9H, to identify, sort, and collect two or more target particle types.

The sorting device 300 shown in FIG. 10A is a serial multi-chamber sorting device comprising a first manipulation chamber 310 and a second manipulation chamber 320. The first and second manipulation chambers 310 and 320 may be configured so as to be capable of performing optoelectronic manipulation, including optoelectronic scanning, to identify and segregate differing particle types as has been described herein. The first chamber 310 and the second chamber 320 may be in flow communication with each other via a channel 330 and a valve 332. The first chamber 310 may also be provided with an inlet 320 and an associated valve 322, which may be similar to the inlet 120 and valve 122 described above with reference to FIG. 8. The second chamber 320 may be provided with an outlet 340 and a valve 342. Each of the chambers 310 and 320 may further be in flow communication with respective outlets 350 and 360 leading to collection channels 354 and 364 which in turn are in flow communication with respective collection reservoirs 356 and 366. Each of the collection reservoirs 356 and 366 may be provided with a valve 352 and 362 and an outlet channel 358 and 368 configured to direct collected target particles out of the sorting device 300.

Various modes of operation may be envisioned for the serial sorting device 300 of FIG. 10A and, based on the teachings provided herein, would be understood by one of ordinary skill in the art. According to various exemplary embodiments, the first manipulation chamber 310 may be filled with a sample containing a plurality of particle types, including a first target particle type, a second target particle type, and other nontarget particle types. The first manipulation chamber 310 may be filled with the sample while the valve 332 is closed such that the manipulation chamber 320 remains free of sample. A scanning light beam similar to that described with reference to FIG. 9B may be used to scan the manipulation chamber 310 and thus create a DEP force acting on the various particles in the chamber 310. By controlling the scanning speed of the light source and capturing images of the chamber so as to determine the dielectrophoretic movement characteristics (e.g., displacement) of the various particles as a result of the scanning, particles of the first target particle type may be identified and moved into the collection reservoir 356 by using focused light beams in a manner similar to that described with reference to FIG. 9C.

After the particles of the first target particle type have been collected in collection reservoir 356, the sample now containing the second target particles type and nontarget particles, and from which the first target particle type has been removed, may be moved into the second manipulation chamber 320, by opening at least valve 332. By way of example, a pump (e.g., a microfluidic pump) and/or other fluid handling equipment, which may be in flow communication with the manipulation chamber 320 (for example, via the inlet 320 or outlet 340) may be used to move the sample from the first manipulation chamber 310 into the second manipulation chamber 320. Those having skill in the art would understand that various methods may be used to cause the sample in chamber 310 to flow to chamber 320 and the corresponding positions of the valves 322, 332, 342 may be determined based on the desired flow and devices used to create that flow.

Optoelectronic scanning, identification, and collection of particles of the second target particle type can again be performed in manipulation chamber 320, consistent with the principles discussed herein and as described with reference to FIG. 9B-9D, and the particles of the second target particle type can be segregated and moved into the collection reservoir 366. The collected target particles of the first and second target particle type can then be removed from the sorting device 300 by passing through the respective outlet channels 358 and 368 with the valves 352 and 362 in the open position. In an exemplary aspect, the target particles may be removed via flushing, pumps, or other fluid handling mechanisms, for example, in a manner similar to that described with reference to FIG. 9H. It should also be understood that flushing of the manipulation chambers 310 and 320 may occur as desired during the sorting/collection process described with reference to FIG. 10A.

In an alternative exemplary aspect, the serial sorting device 300 of FIG. 10A may be used to accomplish simultaneous sorting of a first target particle type and a second target particle type by filling both chambers 310 and 320 with a sample containing one or more particles of the first target particle type, one or more particles of the second target particle type, and one or more nontarget particles. Once sample fills both chambers 310 and 320, two differing scanning light beams (not shown) may be used to respectively scan each chamber 310 and 320. Using the various principles described herein, particles of the first target particle type may be identified in chamber 310 and collected in collection reservoir 356 and particles of the second target particle type may be identified in chamber 320 and collection in collection reservoir 366. Once the first and second target particle types are collected in chambers 356 and 366, respectively, they may be removed from the sorting device 300 for further processing and/or manipulation.

As with the embodiment of FIGS. 9A-9H, multiple iterations of sample filling, scanning, collecting, flushing, etc. may be performed as desired in the sorting device embodiment of FIG. 10A. Moreover, although FIG. 10A shows two manipulation chambers and corresponding collection reservoirs, it is envisioned that the device could include any number of chambers and collection reservoirs, depending, for example, on the number of differing target particle types it is desired to collection, the total number of particles it is desired to collect, and other factors.

Referring now to FIG. 10B, an exemplary embodiment of a parallel multi-manipulation chamber sorting device is schematically depicted. In this embodiment, the sorting device 400 comprises a manipulation chamber 410 having two outlets 440 and 450 leading to collection channels 444 and 454 and ultimately to two respective collection reservoirs 446 and 456. Each collection reservoir 446 and 456 may have an outlet 448 and 458 and corresponding valve 442 and 452, which may be a microfluidic valve, for example. Similar to the manipulation chamber 110 described with reference to FIGS. 9A-9H, the manipulation chamber 410 also may have an inlet 420 for sample introduction and an outlet 430 for waste removal, with corresponding valves (e.g., microfluidic valves) 422 and 432.

According to various exemplary aspects, the sorting device 400 may be used for parallel optoelectronic identification, sorting, and collecting. For example, a sample containing a first target particle type, a second target particle type, and nontarget particles may be introduced so as to fill the manipulation chamber 410 by opening valves 422 and 432, while valves 442 and 452 remain closed. The sample in the manipulation chamber 410 may be scanned via a scanning light beam (not shown) in a manner similar to that described with reference to FIGS. 9A-9H, for example. After scanning, identification of particles of the first and second target particle types in the sample may occur in accordance with various principles described herein. Such identification may occur as explained with reference to FIG. 4C, for example. Once the particles of the first and second target particle types have been identified and located, focused light beams, such as, for example, rings of light or solid circles of light, may be used to capture the target particles and move them via respective collection channels 444 and 454 into respective collection reservoirs 446 and 456. For example, the first target particle type may be moved into the collection reservoir 446 and the second target particle type may be moved into the collection reservoir 456, or vice versa. The sorting device 400 may be flushed and numerous iterations of sample addition, scanning, particle collection, and/or flushing may occur as desired.

Further, although FIG. 10B depicts two collection channels and collection reservoirs in flow communication with the manipulation chamber 410, it should be understood that any number of collection channels and collection reservoirs may be used depending, for example, on the number of differing target particle types it may be desired to sort and collect.

The velocity of particle movement via optoelectronic scanning or other optoelectronic particle manipulation may be determined by the size and dielectric constant of the particle, the intensity of the light, the applied potential bias, the frequency of the AC current, the medium in which the particles are suspended, and other factors that affect the DEP force acting on the particle. In some circumstances, such as, for example, in some sorting processes where it may be necessary to carefully sort a specific particle type or types from among others, it may be desirable to have a relatively slow velocity at which the particle or particles move during manipulation. A relatively slow manipulation velocity may also be used to capture and reroute particles having a relatively weak DEP force (e.g., a relatively low threshold or escape velocity) in order to prevent such particles from escaping. In other situations, however, it may be desirable to move particles at a faster speed. For example, for particles having a relatively strong DEP force, a relatively high velocity may be used for capturing and rerouting the particles, which may in turn increase sorting throughput. As discussed above, it may be possible to alter the DEP force acting on a particle by changing various parameters.

Figure 11A:
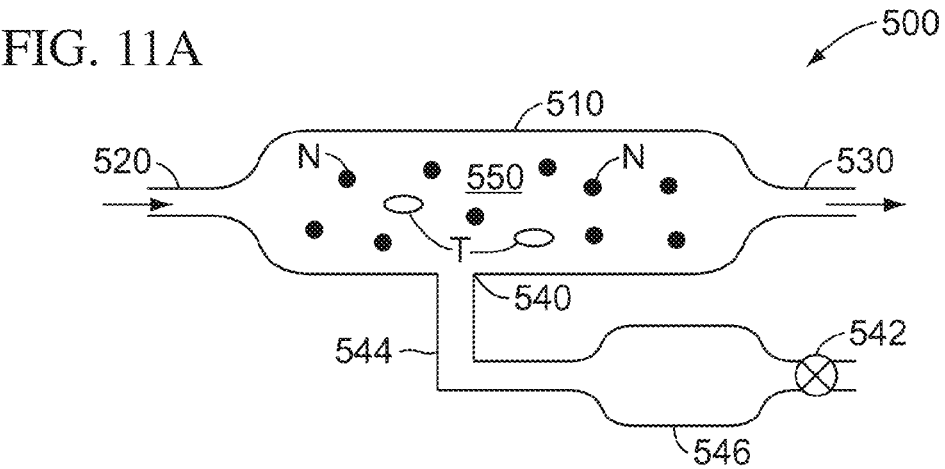
FIGS. 11A-11C are schematic illustrations of another exemplary embodiment of use of the device of FIG. 8.
Figure 11B:
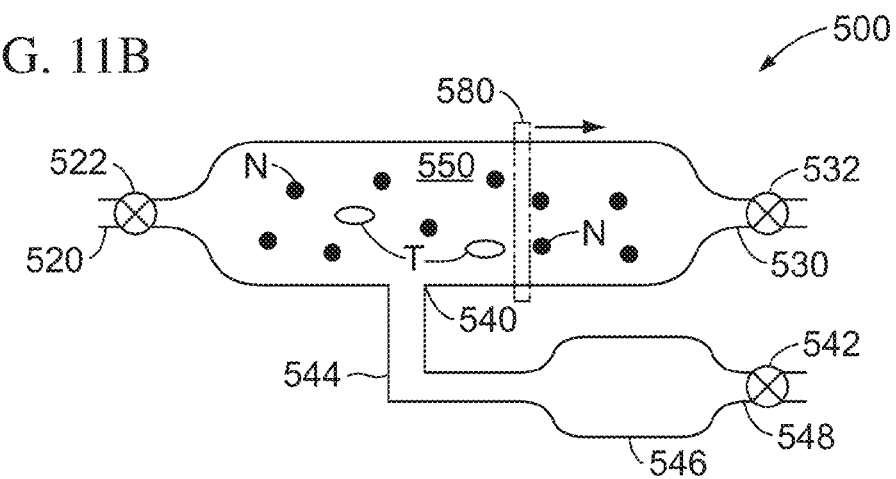
Figure 11C:
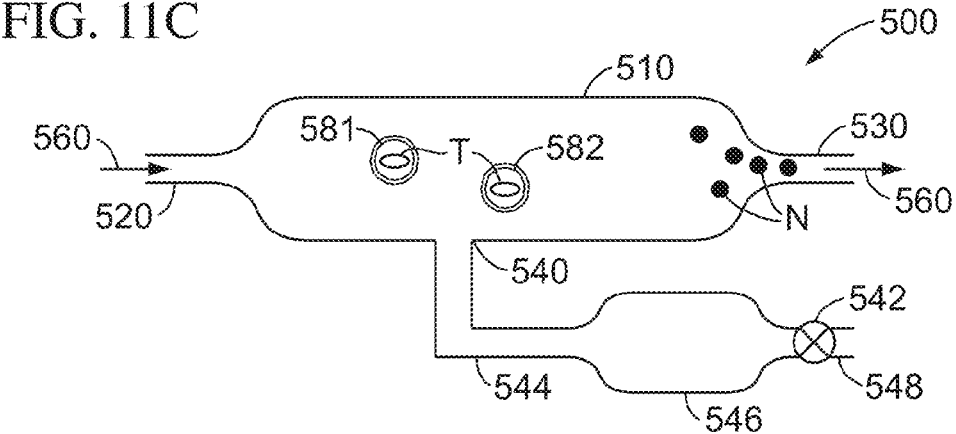

The exemplary embodiment of FIGS. 11A-11O schematically depicts an optoelectronic sorting device and technique in which the particle manipulation speed (e.g., the speed at which nontarget particles N are removed from the chamber) may rely on the flow of the medium rather than the speed of the optoelectronic (DEP) manipulation of the particles. In this case, as will be explained further below, the nontarget particles may be separated from target particles T and removed from the chamber by flushing the chamber 510 while the target particles T are held stationary by focused incident light 581 and 582 and a corresponding DEP force, as shown in FIG. 11C. Thus, collection of the target particles T in the chamber 510 occurs substantially at the flow speed at which the nontarget particles N are removed from the chamber, rather than the speed of DEP manipulation out of the chamber, as described, for example, with reference to FIGS. 9C and 9D. After removal of the nontarget particles T, the target particles T may also be moved into the collection reservoir 546 via flowing the target particles T into the chamber. In this way, a higher sorting throughput may be achieved since several particles at a time may be moved from the chamber via flushing, as opposed to moving smaller amounts or individual particles from the chamber via optoelectronic manipulation. The speed at which the particles T and/or N are removed from the chamber depends on a flow speed rather than the speed of optoelectronic manipulation. The flow can be induced, for example, by pressure, electro-osmosis, or other flow inducing mechanisms. In an exemplary aspect, pressure may be used to flush the particles from the chamber may occur. Further, the process of the exemplary embodiment of FIGS. 11A-11C, which will be described below, may comprise an optoelectronic scanning step, a capturing step (via optoelectronic dielectrophoresis), and two flushing steps (one for flushing nontarget particles and one for flushing target particles for collection). Thus, the sorting aspect of the process relies in large part on the speed at which the flushing occurs.

As depicted in the exemplary embodiment of FIGS. 11A-11C, a sample 550 containing one or more particles of a target particle type T and one or more particles of a nontarget particle type N may be introduced into a manipulation chamber 510 of a sorting device 500 which may be similar in structure to the sorting device 200 described with reference to FIGS. 9A-9H. That is, the manipulation chamber 510 may include an inlet 520 and corresponding valve 522 to allow for introduction of sample and/or flushing medium into the manipulation chamber 510. The manipulation chamber 510 also may comprise an outlet 530 and corresponding valve 532 to permit removal of sample and/or flushing medium out of the chamber 510. Another outlet 540 may lead to a collection channel 544 for the routing and collection of target particles T in a collection reservoir 546 that is in flow communication with the channel 544. The collection reservoir 546 may comprise an outlet 548 and corresponding valve 542. As was described with reference to the sorting device and technique of FIGS. 9A-9H, a variety of fluid handling devices and other instrumentation, such as, for example, microfluidic pumps, electro-osmosis fluid handling devices, and various other flow control mechanisms, including valves (e.g., microfluidic valves) may be provided in connection with the sorting device 500 of FIGS. 11A-11C so as to control flow therethrough.

By way of example, use of the sorting device 500 for sorting target particles T having a negative Clausius-Mosotti value from nontarget particles N having a negative Clausius-Mosotti value will be described. It should be understood, however, that the sorting device 500 could also be used to sort target and nontarget particles which both have positive Clausius-Mosotti values or to sort target particles of negative Clausius-Mosotti value and nontarget particles of positive Clausius-Mosotti value or vice versa.

Referring to FIG. 11A, with valves 522 and 532 open and valve 542 closed, sample 550 may be introduced into the manipulation chamber 510. Once the manipulation chamber 510 has been filled with the sample 550, the valves 522 and 532 may be closed and a light beam 580 (e.g., a light beam that spans the width of the chamber 510) may be used to scan across the length of the manipulation chamber 510, for example, in the direction of the arrow shown in FIG. 11B. After the light beam 580 has scanned the manipulation chamber 510, the respective displacements (or other dielectrophoretic movement characteristics) of the particles T and N may be measured, for example, via a CCD camera and image processing software. From those displacement measurements, the target particles T may be identified, for example, as described with reference to FIG. 4C or by otherwise correlating the measured displacement of the various particles with individual particle types.

With the scanning light beam 580 turned off, the identified target particles T in the sample 550 may then be captured by using a focused light beam to individually trap each identified target particle T (or possibly clusters of particles T) in the sample. For the example of FIGS. 11A-11O wherein the target particle type T has a negative Clausius-Mosotti value, the focused light beams used to trap the particles T may have a substantially ring-like configuration, as shown by focused light beams 581 and 582 in FIG. 11C. If, however, the target particle type had a positive Clausius-Mosotti value, the focused light beams used to trap the target particles could have a solid substantially circular configuration such that the target particles would be trapped within the light surrounding the particles.

With the target particles T captured (e.g., trapped) by the focused light beams 581 and 582, the valves 522 and 532 may be opened and the chamber 501 may be flushed with a flushing medium 560 (e.g., an aqueous buffer solution) to remove the nontarget particles N, as depicted in FIG. 11C. Because the target particles T are trapped (captured) by the negative DEP force created by the light beams 581 and 582, the target particles T are not removed from the manipulation chamber 510 with the flushing medium. In order to hold the target particles T within the focused light 581 and 582 while the nontarget particles N are being flushed from the chamber, the target particles T should have a relatively strong DEP force. In other words, the DEP force acting on the target particles T should be sufficient to prevent the particles from escaping the focused light 581 and 582 and being flushed out of the chamber with the nontarget particles N.

Once the chamber 510 has been flushed and rid of all the nontarget particles N, the trapped target particles T may be routed through outlet 540, channel 544, and into collection reservoir 546. The routing of the target particles T may be accomplished via a variety of fluid handling techniques, including, but not limited to, pressure-induced flow, for example, pumping, electro-osmotic flow. Alternatively, as with other embodiments described herein, the target particles T could be removed from the chamber 510 via optoelectronic manipulation.

Figure 30:
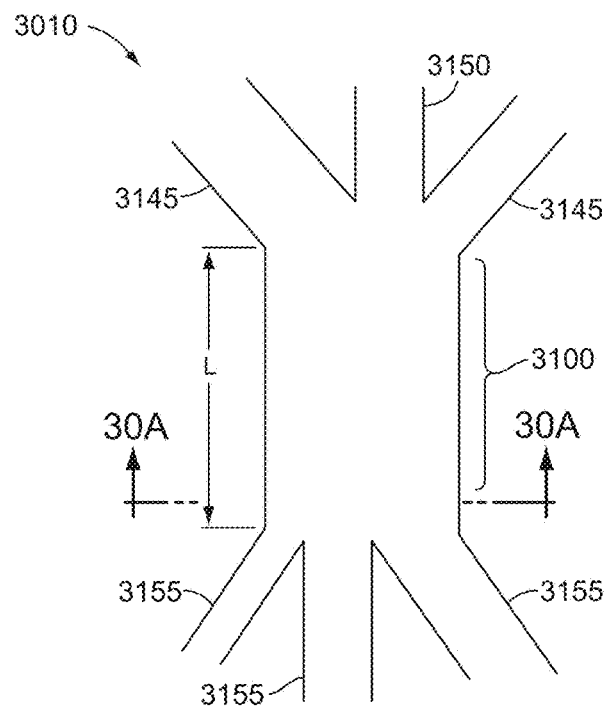
FIG. 30 is a schematic view of an exemplary embodiment of a particle sorting device that uses an optoelectronic scanning chamber.
Figure 31:
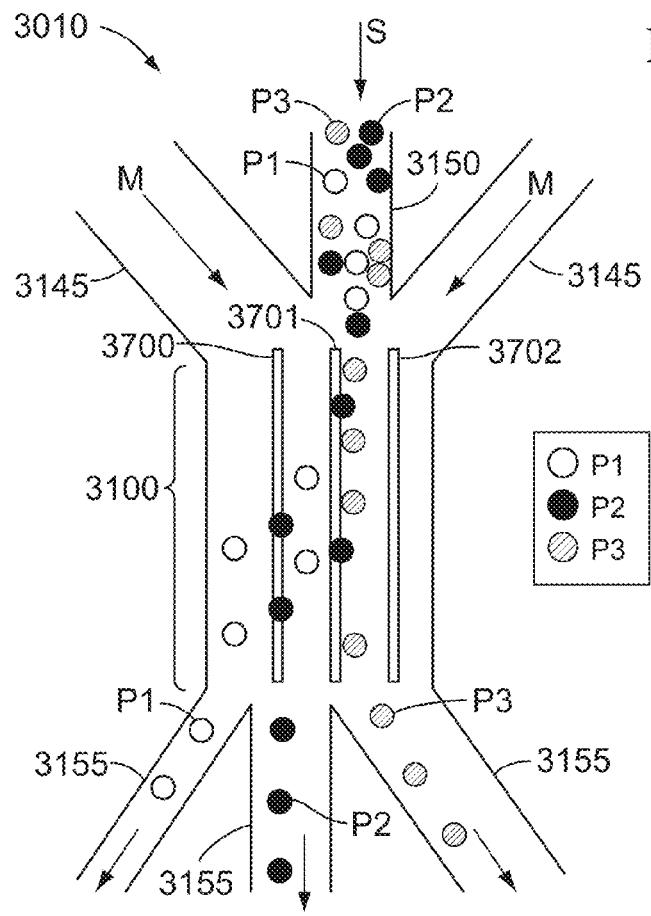
FIG. 31 is an exemplary embodiment of sorting and collecting particles using the device of FIG. 30.
Figure 32:
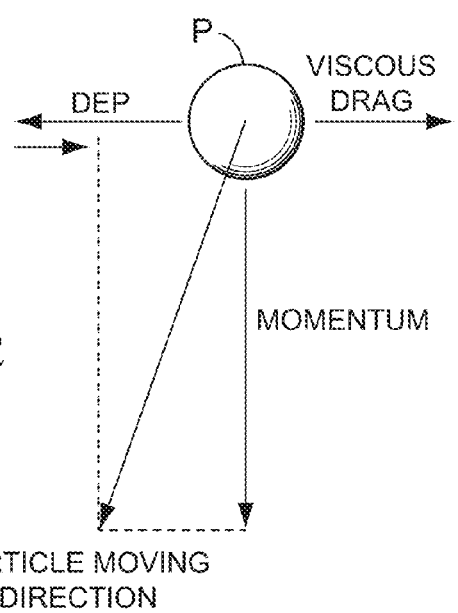
FIG. 32 is a force diagram of a particle in FIG. 31.

FIGS. 30-32 illustrate yet another exemplary embodiment of a device and technique for identifying differing particle types, including, for example, particles of interest, in a sample containing a plurality of differing particle types, separating the differing particle types, and collecting the differing particle types utilizing the principles of optoelectronic manipulation (e.g., optoelectronic scanning) described herein. As explained further below, the exemplary embodiment of FIGS. 30-32 may achieve a relatively high throughput of particles (e.g., cells) because the optoelectronic scanning occurs over a flowing stream of particles rather than over a stationary solution of particles. Moreover, as compared to conventional sorting techniques such as, flow cytometry and/or techniques relying on patterned, deposited electrodes and/or high-power lasers, for example, the embodiment of FIGS. 30-32 may be easier and less costly to fabricate, may be simpler to operate without the need for chemical labels, an analysis region, and/or may provide operational flexibility by changing scanning parameters.

Figure 30A:
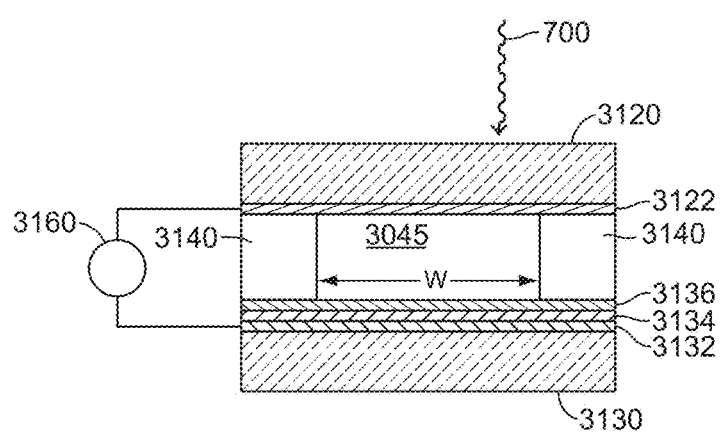
FIG. 30A is a cross-sectional view of the device of FIG. 30 taken through line 30A-30A.

In various exemplary embodiments, a device 3010 for sorting, separating and collecting small particles utilizing optoelectronic scanning may have a configuration similar to a conventional flow cytometer, as depicted, for example, in FIG. 30. The device 3010, however, may include an optoelectronic manipulation chamber 3100 in place of the analysis and sorting regions typically found in conventional flow cytometers. FIG. 30A, shows the optoelectronic manipulation chamber 3100 portion of the device 3010 in greater detail in the cross-sectional view taken through line 30A-30A. By way of example and not limitation, the chamber 3100 may have a configuration substantially the same as the chamber 100 depicted and described with reference to FIG. 1. Like parts of the chamber 3100 are represented by the same reference labels as the chamber 100 in FIG. 1 except in the 3100 series. The spacers 3140 in FIG. 30A may be configured so as to form a microfluidic channel 3045 through which the flow of particles may pass during sorting and separating. The spacers 3140 may have a variety of forms as would be understood by those skilled in the art. According to an exemplary embodiment, the spacers 3140 may be a pressure sensitive adhesive layer that is die-cut to form channels and chambers. Those having ordinary skill in the art would also understand that the chamber 3100 may have a variety of configurations consistent with the teachings herein to perform optoelectronic scanning of particles.

The device 3010 also may include a sample input port 3150 for introducing a sample containing a plurality of particles of differing types into the device 3010 (e.g., a biological sample containing a suspension of differing types of cells). Ports 3145 may be disposed on either side of the sample input port 3150 for introducing an aqueous medium, buffer solution, such as, for example, phosphate buffered saline with 1% bovine serum albumin, or other suitable buffer medium for suspending the particles as described herein, into the device 3010. The buffer can be introduced in a manner that causes a sheath flow similar to that in conventional flow cytometers. In other words, the flow through the portions 3145 "pinches" the sample that is introduced into the portion 3150 so as to cause the particles in the sample to substantially align and flow through the microfluidic channel 3045 of the optoelectronic scanning chamber 3100.

A plurality of branch channels 3155 may be positioned on a side of the chamber 3100 opposite to the ports 3145 and 3150. The branch channels 3155 may be configured to collect the differing types of particles that have been sorted and separated in the chamber 3100. Each branch channel 3155 may be configured to collect a differing type of cell or, alternatively, waste. Although the exemplary embodiment of FIGS. 30 and 31 depict three branch channels 3155, it should be understood that the device 3010 may include any number of branch channels, depending, for example, on the number of differing particle types for which collection is desired. In an exemplary aspect, the number of channels may equal the number of differing particle types that are being collected plus an additional channel to collect waste.

FIG. 31 illustrates an exemplary embodiment of using the device 3010 of FIG. 30 to sort three differing types of particles (e.g., cells) in a sample. The differing particle types P1, P2, and P3 are indicated by different shading in FIG. 31. To begin, a sample S containing the differing particle types P1, P2, and P3 may be introduced into the sample introduction port 3150 and a sheath flow medium M may be introduced into the ports 3145 in the directions shown by the arrows in FIG. 31. The sheath flow medium M is directed toward the sample S so as to "pinch" the flow of sample S and the particles P1, P2, and P3 contained in the sample into a columnated flow substantially through the microfluidic channel 3045 in the chamber 3010.

As the sample S containing the particles P1, P2, and P3 flows through the channel 3045, a series of differing scanning light beams 3700, 3701, and 3702 may scan across the chamber 3100 in the direction of the arrow shown in FIG. 31 (e.g., from right to left across the chamber 3100). The speed, frequency, and/or intensity of the light beams 3700, 3701, and 3702 may be selected so as to entrain and capture the differing particle types P1, P2, and P3 via the DEP force associated with each light beam 3700, 3701, and 3702, as is described in the teachings herein. The optoelectronic scanning that occurs as the particles P1, P2, and P3 pass through the optoelectronic scanning portion 3100 of the device 3010 causes the particles P1, P2, and P3 to become sorted and separated into substantially three distinct columns as they move down the length of the device 3010. That is, due to the varying balance of the viscous drag, the DEP force, and the momentum of the moving stream of sample acting on a particle, as schematically represented in FIG. 32, the differing particle types P1, P2, and P3, are sorted and separated in the lateral direction as they move through the chamber 3100. Thus, by the time the flow of the sample S and particles P1, P2, and P3 reach the branch channels 3155, they are sorted into columns that substantially align with each branch channel 3155. This permits the particles of each particle type P1, P2, and P3 to be collected in a respective branch channel 3155, as shown in FIG. 31, and removed from the device and/or moved to a location for further processing. In various exemplary embodiments, the branch channels 3155 may be positioned and configured such that all of the differing particles flow into a single channel 3155 in the absence of optoelectronic scanning as they pass through the portion 3100 of the device 3010. Those having skill in the art would recognize that one of the branch channels 3155 in FIG. 31 may be used to collect waste and/or particles not of interest, while the other two are used to collect differing particle types of interest.

In various exemplary embodiments, various design parameters associated with the device 3010, such as, for example, the width W and the length L of the channel 3045, the rate of flow of the sample S, the rate of flow of the medium M, the flow pinch ratio, the scan speed of the light beams, etc., may be determined by running experiments in an optoelectronic scanning chamber to determine the amount of displacement that particles of particular type experience as they are subject to optoelectronic scanning. A database may be compiled that stores the displacement data for each particle type along with the various parameters used to achieve the displacement. The design, configuration, and operational parameters of the optoelectronic scanning chamber portion 3100 may be selected accordingly to achieve the desired sorting, separating, and collection as described above.

The various sorting device embodiments depicted in FIGS. 8-11 and 30-32 are schematic depictions intended to illustrate various exemplary steps that may be used to scan, identify, sort, and/or collect particles of interest from other particles in a sample. It should be understood that the manipulation chambers, the inlets and outlets thereto, the collection reservoirs, the light sources, and the various other elements of the sorting devices could have a variety of configurations permitting the implementation of optoelectronic manipulation and other flow handling as described and/or otherwise taught herein. Further, in order to provide control over the scanning, identification, and/or sorting techniques described herein and in particular with reference to FIGS. 8-11 and 30-32, it may be desirable to alter the positivity or negativity of the Clausius-Mosotti values of the target particles and/or the nontarget particles. By way of example, surface-active agents may be applied to the target and/or nontarget particles as desired to change the Clausius-Mosotti values of those particles from positive to negative or vice versa. According to exemplary aspects, such a change to the particles may be a reversible change such that the original Clausius-Mosotti value can be recovered after scanning, identification, sorting, and/or collection has been performed.

As described above, DEP (dielectrophoresis) is the motion imparted on uncharged particles, for example, through a solution, as a result of polarization induced by nonuniform electric fields, whereas electrophoresis (EP) is the migration of particles through a solution under the influence of an applied electric field by virtue of the particle's charge. It is envisioned that both optoelectronically induced DEP and EP may be used to manipulate particles in accordance with various exemplary aspects of the invention. FIGS. 12A-12D illustrate an exemplary embodiment for utilizing an optoelectronic manipulation chamber subject intermittently to an AC current source and a DC current source in order to manipulate particles in a sample via DEP forces and EP forces. Utilizing such intermittent AC-DEP and DC-EP manipulation schemes may achieve enhanced particle separation and sorting.

In the exemplary embodiment of FIGS. 12A-12D, an optoelectronic manipulation chamber 810 may be similar in structure to the manipulation chamber described with reference to FIG. 1. In accordance with an exemplary aspect, the first substrate 820 of the chamber 810 may be a glass substrate and may comprise a transparent electrode layer 822, such as, for example, PEGylated transparent gold electrode, which will be described in further detail in the example below. The second substrate 830 may be a glass substrate and may comprise an electrode layer 832, such as, for example, an aluminum, gold, or ITO electrode, and a photoconductive layer 834. The photoconductive layer 834 may be, for example, a PEGylated photoconductive layer 834. A variety of other materials may be used for the substrate materials and various layers on the substrate and could be selected based on the desired operating features of the manipulation chamber. For various examples of suitable materials, reference is made to U.S. application Ser. No. 10/979,645, incorporated by reference herein. The various exemplary materials for the manipulation chamber 810 set forth above may be particularly suitable for using the manipulation chamber to perform both optoelectronic DEP and EP, as will be described below.

Figure 12A:
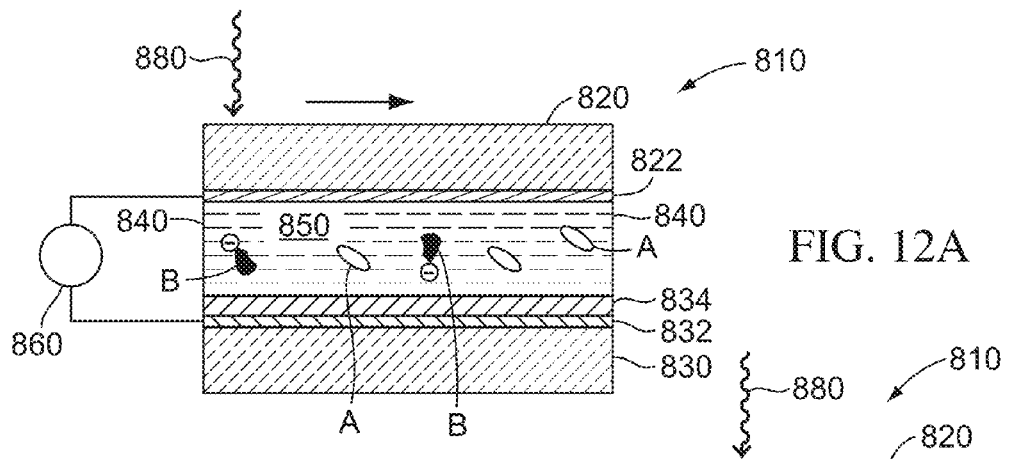
FIGS. 12A-12D are cross-sectional, side views of an exemplary embodiment of an optoelectronic manipulation chamber and use of the manipulation chamber.

A sample 850 containing a plurality of differing particle types, for example particle type A and particle type B, may be provided in the space formed between the substrate 820 and the substrate 830, as illustrated in FIG. 12A. As with the embodiment of FIG. 1, a seal 840 may be provided along the edges of the substrates 820 and 830 to hold the substrates together and to define a closed cavity configured to receive the sample 850. Though not shown in FIGS. 12A-12D, it should be understood that the chamber 810 may be provided with various inlets and outlets so as to permit addition of materials to the chamber and removal of materials from the chamber as desired based on, for example, the manipulation processes that may occur in the chamber.

A light beam 880, which may extend in a direction into the drawing sheet so as to span across a width of the manipulation chamber 810, may be used to illuminate the photoconductive surface 834 and, in conjunction with the applied power source 860 (AC or DC), as will be described, create a DEP or EP force for manipulating the particles A and B contained in the sample 50.

The particles in the sample 850 may have either positive or negative Clausius-Mosotti values, respectively. In the exemplary embodiment shown in FIGS. 12A-12D, particle type B is negatively charged. The negative charge may be imparted to the particles of type B, for example, by a surface-active modification agent and/or a ligand, or may be the inherent charge of the particle type B. The negative charge on particle type B is depicted by the negative sign (−) in the circle attached to the particles.

Figure 12B:
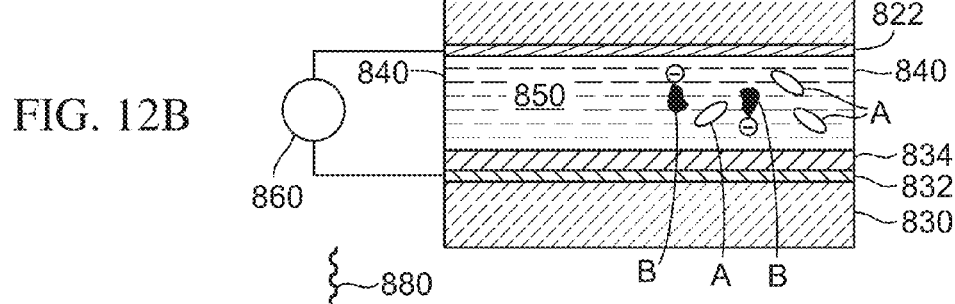

Optoelectronic scanning may be initiated and a DEP force created to act on the particles by applying an AC current from the power source 860 and by moving the light beam 880 along the manipulation chamber 810 in the direction of the dark arrow in FIG. 12A. When the light beam 880 scans along the manipulation chamber 810 in the direction shown in FIG. 12A, the DEP force pushes and concentrates all of the particles to the right side of the chamber 810, as illustrated in FIG. 12B. That is, assuming the scanning speed of the light beam has been selected appropriately, the light beam scans the manipulation chamber, particles with negative Clausius-Mosotti values will be repelled by the light and thus be expelled in front of the light beam and toward the end of the manipulation chamber at the right hand side of the drawing sheet. Particles with positive Clausius-Mosotti values will be attracted to the light beam as it scans and thus also will wind up at the end of the manipulation chamber toward the right hand side of the drawing sheet as they move toward the scanning light beam 880.

Figure 12C:
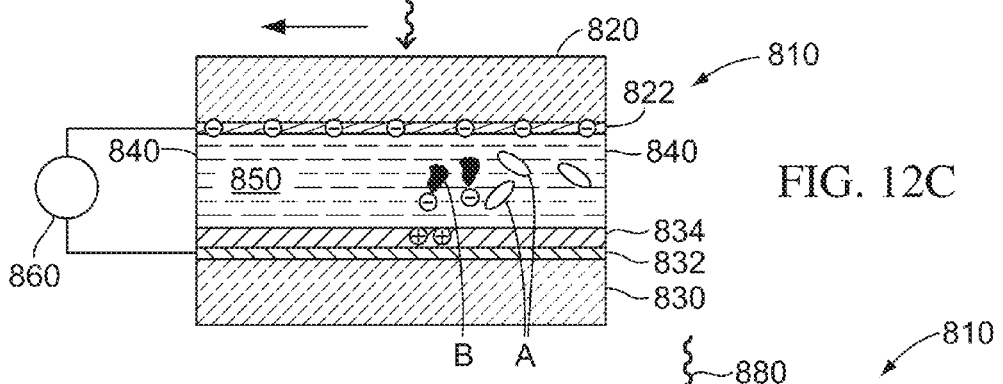
Figure 12D:
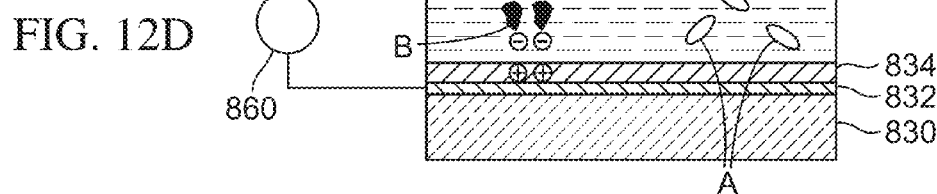

Once the particles have been pushed to the end of the manipulation chamber 810, as illustrated in FIG. 12B, the direction of scanning of the light beam 880 may be reversed, for example, such that the light beam 880 moves along the chamber 810 in the direction indicated by the dark arrow in FIG. 12C. At the same time, the power source 860 may be switched such that a DC signal is supplied instead of the AC signal. The DC power source may be controlled such that the electrode 822 becomes negatively charged and the portions corresponding to the regions of the photoconductive layer 834 that are illuminated by the light beam 880 become positively charged. The respective charges are illustrated by a plus sign (+) in a circle and a minus sign (−) in a circle in FIGS. 12C and 12D. As the light beam 880 moves along the manipulation chamber 810 in a direction toward the end of the chamber toward the left hand side of the drawing sheet, the negatively charged particles of particle type B move toward the scanning light beam 880 as a result of the EP force acting thereon. The negatively charged particles of particle type B move away from the neutral particles of particle type A, which are not under the action of the induced EP force. As illustrated in FIG. 12D, the particles of type B may be moved a relatively large distance away from the particle type B particles by continuing the scanning of the light beam 880 toward the end of the manipulation chamber 810 at the left hand side of the drawing sheet. Thus, due to the ability to move the particles of particle type B away from the particles of particle type A, substantially without moving the particle type A particles, enhanced separation of the particles may be possible.

The scanning steps of FIGS. 12A-12D may be repeated as many times as desired in order to achieve the desired separation and/or other manipulation of the particles. Those skilled in the art would understand that positively charged particles may also be separated from other neutral particles by altering the polarity of the applied DC source.

Figure 13:
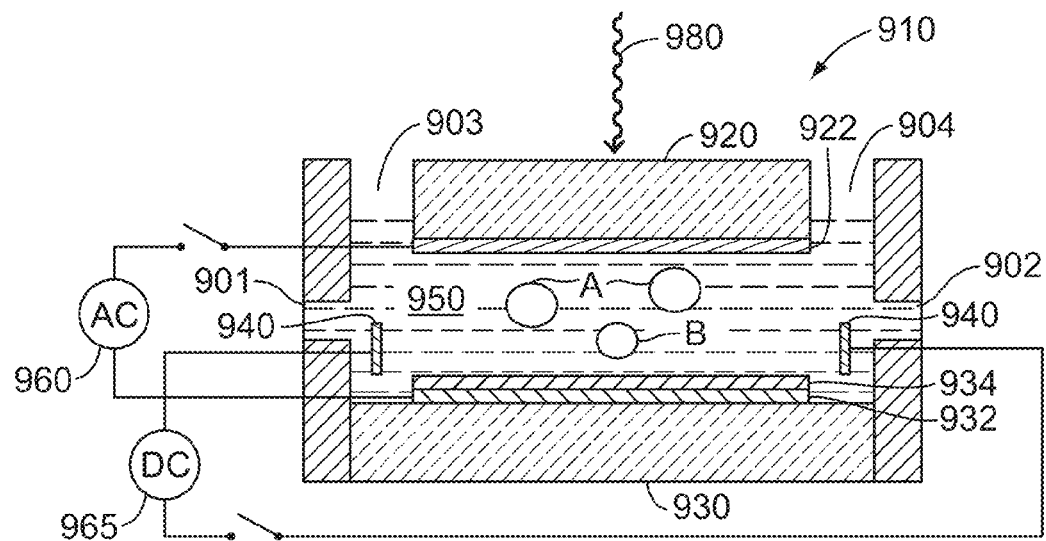
FIG. 13 is a cross-sectional, side view of yet another exemplary embodiment of an optoelectronic manipulation chamber.

In various exemplary embodiments, it may be useful to rely on both DEP and EP forces, either simultaneously or separately, to cause particles to move in two dimensions, such as, for example, and/or to enhance particle sorting. FIG. 13 illustrates an exemplary embodiment of a manipulation chamber 910 that utilizes both DEP and EP forces to enhance sorting.

The manipulation chamber 910 may comprise a first substrate 920 with a transparent electrode 922 and a second substrate 930 with an electrode layer 932 and a photoconductive layer 934. The photoconductive layer 934 may have a transparent protective layer provided thereon, as was described with reference to FIG. 1. According to an exemplary aspect, the first and second substrates and various layers provided thereon may be made of the materials set forth in the Example below, however other suitable materials also may be used, as has been described above with respect to the exemplary embodiment of the manipulation chamber of FIG. 1.

As illustrated in FIG. 13, the manipulation chamber 910 also may comprise an inlet 901 configured to permit introduction of material to the chamber 910, and an outlet 902 configured to permit removal of material from the chamber. Vents 903 and 904 also may be provided to release pressure that may develop in the chamber, for example, due to hydrolysis of water in the chamber during application of the DC power source. The number of inlets, outlets, and vents illustrated in FIG. 13 is exemplary only and it should be understood by those having skill in the art that any number of inlets, outlets and vents may be provided as desired depending on the application of the manipulation chamber. It also should be understood, that the manipulation chamber 910 could be in flow communication or otherwise coupled to a variety of other instrumentation, reservoirs, or the like for further fluid handling, manipulation, and/or processing of the sample and/or particles introduced to the chamber. Such instrumentation may include, for example, microfluidic pumps, valves, additional manipulation chambers, and/or other fluid handling devices.

Similar to the exemplary embodiment of FIG. 1, the manipulation chamber 910 may comprise an AC power source 960 connected between the electrodes 922 and 932. The power source 960 may be closed to complete the circuit between the electrodes 922 and 932 when optoelectronic scanning occurs. Thus, as was described above for various embodiments of optoelectronic scanning, a scanning light beam 980 may be used in conjunction with the applied AC signal to modulate a nonuniform electric field in the manipulation chamber and corresponding DEP force acting on particles A and B contained in an aqueous medium 950 supplied to the chamber 910.

The manipulation chamber 910 may further comprise electrodes connected to a device that imposes and controls a potential DC bias. For example, as illustrated in the exemplary embodiment of FIG. 13, electrodes 940 may be positioned at opposite ends of the chamber 910 so as to face one another. For example, the electrodes 940 may be positioned toward the left hand and right hand side of the chamber 910, as illustrated in FIG. 13. The electrodes 940 may be connected to a DC power source 965. In this manner, in addition to the DEP force created by the electrodes 922 and 932, the AC source, and the scanning light beam 980, the incorporation of an orthogonal DC potential bias across the length of the manipulation chamber 910 enables the particles to be separated in a second dimension via EP forces.

According to various exemplary aspects, the movement of a particle by virtue of the EP force may be the same or opposite to that of the OET scanning. For example, scanning the chamber from left to right creates a DEP force which concentrates the particles to the right hand side of the chamber shown in FIG. 13. If a DC bias is applied, either during or after scanning, such that the electrode 940 on the left hand side of the chamber 910 is positive, the drag force for a negatively charged particle, such as particle type B illustrated in FIG. 12, may be artificially increased by adding an EP force to the particle in the same direction as the drag force, which will facilitate its escape from the scanning light beam and cause the negatively charged particles to migrate further to the left hand side of the chamber 910 in FIG. 13. The additional migration of the negatively charged particles may result in enhanced separation. Those having ordinary skill in the art would understand how to alter the DC polarity of electrodes 940 in order to improve separation of positively or negatively charged particles.

According to various exemplary aspects, the manipulation chamber 910 may be repeatedly scanned with the light beam 980 and an electro-osmotic flow in the medium may be induced in a direction opposite the scan via the electrodes 940. In such circumstances, particles having sufficient positive DEP force acting on them may be collected to the right hand side of the chamber in the direction of scanning, for example, while other cells would be swept to the left hand side of the chamber 910 in the direction of the electro-osmotic flow, for example. A series of scans may be implemented with the electro-osmotic flow being relatively strong initially so as to collect cells experiencing a relatively strong positive DEP force. Those cells may then be diverted and collected in a collection area (e.g., reservoir) outside of the manipulation chamber. The electro-osmotic flow may then be progressively reduced in subsequent scans to collect cells of decreasing dielectric potential (e.g., decreasing DEP force acting thereon).

When compared to other fluid flow mechanisms, such as, pumping, for example, electro-osmotic flow may produce a plug flow profile as compared to a parabolic flow profile. This plug flow profile results in a flow velocity that is uniform throughout the manipulation chamber such that cell velocity is not reduced close to the walls of the manipulation chamber.

As described above, therefore, particle sorting may be achieved by subjecting the particles to competing forces, e.g., DEP force and fluid flow (electro-osmosis). An EP force also may be established, for example, by the electrodes 940 and DC power source 965 of the embodiment of FIG. 13. According to an exemplary aspect, the inner walls of the manipulation chamber 910 may be coated with substances designed to eliminate and/or reduce electro-osmotic flow such that the EP force becomes the dominant force outweighing (or replacing) the fluid flow forces moving particles in the description above.

In order to control and/or facilitate electrophoresis of one or more particles, surface active agents and/or ligands may be applied to the particles to introduce an artificial electric charge to the particles, such as, for example, as was described with reference to FIGS. 12A-12D. Additional examples of surface modification of particles can be found in U.S. application Ser. No. 10/979,645, incorporated by reference herein.

According to various exemplary embodiments, as discussed above, the EP forces created by the electrodes 940 also may induce electro-osmotic flow of the medium containing the particles. Again, by controlling the polarity of the DC bias of electrodes 940, the EP force acting on the medium may be altered and thus the flow direction may be the same as or opposite to the direction of scanning of the light beam 980. The electrophoresis and dielectrophoresis movement of particles and/or medium may take place concurrently, intermittently, or sequentially, depending on the desired movement and/or application.

Aside from positioning the electrodes 940 within the chamber 910 at opposite ends thereof as depicted in FIG. 13, it is envisioned that electrodes could be placed within reservoirs located at either end of the chamber 910. Such reservoirs could be disposed, for example, so as to be in flow communication with inlet 901 and/or outlet 902.

The electrodes used to create the EP force may have a configuration chosen from wires, flags, plates, dots, buttons, rods, tubes, thin layer coatings, arrays, and/or other suitable electrode configurations and combinations thereof. The electrodes may be made of a variety of materials including, but not limited to, noble metals, such as, for example, gold and platinum; non-ferrous metals, such as, for example, aluminum; alloys, such as, for example, stainless steel; and oxides, such as, for example, indium tin oxide; or combinations thereof. A variety of techniques may be used to fabricate the electrodes 940 including, but not limited to, sputtering, vapor deposition, ink-jet printing, electroplating, welding, or other suitable fabrication techniques. According to an exemplary aspect, it may be desirable to fabricate electrodes on a surface with robust adhesion characteristics and those skilled in the art would be familiar with how to accomplish such fabrication.

As discussed, the various substrates, electrode layers, photoconductive layer, and surfaces facing the cavity configured to receive the sample containing particles to be manipulated may be made of a variety of materials and/or have various configurations. According to various exemplary embodiments, it may be desirable to provide the electrode that is disposed underneath the photoconductive layer as a noncontinuous electrode rather than a continuous surface underneath the photoconductive layer. An exemplary embodiment of a manipulation chamber having a noncontinuous electrode in association with the second substrate 1130 is illustrated in FIGS. 14A and 14B.

Figure 14A:
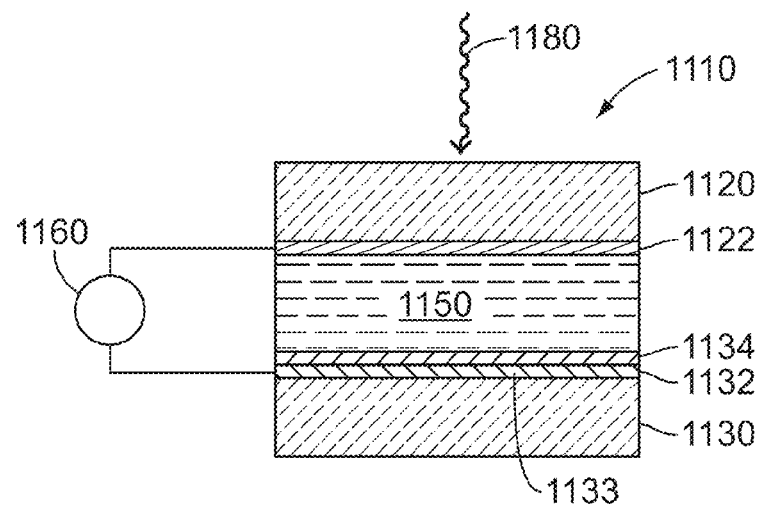
FIG. 14A is a cross-sectional, side view of yet another exemplary embodiment of an optoelectronic manipulation chamber.
Figure 14B:
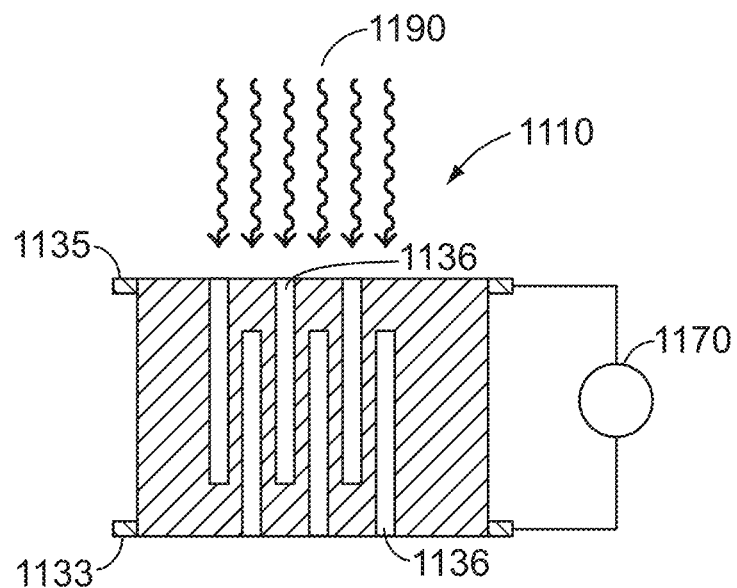
FIG. 14B is a top view of the manipulation chamber of FIG. 14A from the perspective of line B-B shown in FIG. 14A.

FIG. 14A depicts a side view of an exemplary embodiment of a manipulation chamber 1110 having a noncontinuous electrode underneath the photoconductive layer, and FIG. 14B depicts a top view of the bottom substrate layers of the manipulation chamber 1110 of FIG. 14A. For sake of clarity in FIG. 14B, the glass substrate 1130 itself is not shown. As shown in the figures, the manipulation chamber 1110 may have a configuration similar to other manipulation chambers described herein including a first substrate 1120 (e.g., a glass substrate) having a transparent electrode layer 1122 deposited thereon (e.g., layer 1122 may be ITO or a PEGylated gold layer) and a second substrate 1130 (e.g., a glass substrate) having an electrode layer 1132 (e.g. a transparent or nontransparent metal electrode layer such as, for example, aluminum, gold, or ITO) and a photoconductive layer 1134. An additional protective layer (e.g., surface) may be provided on the photoconductive layer 1134 as discussed above. By way of example only, the photoconductive layer 1134 may be provided with a PEGylated $SiO_2$.

As shown in FIG. 14A, a power source 1160, such as for example an AC power source, may be provided so as to complete the circuit between the electrode 1122 and 1132. Moreover, an incident light beam 1180 may be provided so as to scan or otherwise induce the nonuniform electric field and consequent DEP forces acting on the sample within the cavity of the manipulation chamber 1110, as has been described herein.

As shown in the side view of the manipulation chamber 1110 in FIG. 14B, the electrode layer 1132 comprises two individual electrodes 1133 and 1135 rather than a continuous electrode surface. The individual electrodes 1133 and 1135 may be deposited as two elongate strips along the edges of the glass substrate 1130. The electrodes 1133 and 1135 may be deposited by a variety of techniques, including, for example, vapor deposition, sputtering, electroless plating, electroplating, inkjet printing, screen printing of conductive paint, or other suitable deposition techniques. It should be noted that only one of the electrode strips 1133 is illustrated in FIG. 14A, as the other electrode strip 1135, shown in FIG. 14B, is deposited along the edge of the substrate 1130 opposite to the edge shown in FIG. 14A and into the drawing sheet.

According to an exemplary aspect, the photoconductive layer 1134 may be illuminated by a light pattern, such as, for example, by a plurality of individual light beams 1190, such that a plurality of strips on the surface of the photoconductive layer 1134 are illuminated so as to form virtual (e.g., photo-activated) electrodes 1136. The term virtual (or photo-activated) electrode should be understood to refer to an illuminated region of the photoconductive layer 1134 such that the electric field proximate that illuminated region is modulated (e.g., strengthened). The virtual electrodes 1136 may be established via illumination such that adjacent electrodes 1136 are each placed in contact with a different electrode strip 1133 and 1135, as illustrated in FIG. 14B, and such that each electrode 1136 is placed in contact with only one of electrode strips 1133 and 1135.

In accordance with an exemplary aspect, the photo-activated electrodes 1136 may extend from the respective electrode strip 1133 and 1135 in which they are in contact in a direction substantially perpendicular to the direction in which the electrode strips 1133 and 1135 extend. For example, a plurality of individual photo-activated virtual electrodes 1136 may be positioned so as to alternatively contact one of the electrode strips 1133 and 1135 and not the other of the electrode strips 1133 and 1135, as shown in FIG. 14B. Each virtual electrode 1136 may extend in a direction substantially perpendicular to the direction in which the electrode strips 1133, 1135 extend.

It should be understood that the dimensions, position, and number of virtual electrodes that are activated by illuminating the photoconductive layer 1134 may be altered as desired by modifying the light pattern which is mapped onto the photoconductive layer 1134. Moreover, with reference to the description of FIGS. 26A and 26B below, the intensity of the light illuminating the photoconductive layer may also be varied to modulate the strength of the electric field in the vicinity of illuminated regions of the photoconductive layer 1134. Thus, the electric field strength corresponding to the virtual electrodes 1136 may be controlled as desired by respectively varying the intensity of the light illuminating each respective virtual electrode 1136.

A power source 1170, which may be, for example, an AC power source, may be provided so as to electrically couple (e.g., bias) the electrode strips 1133 and 1135. When the strips 1133 and 1135 are biased with an electric potential and when light beams 1190 are activated to individually illuminate each of areas of the photoconductive layer 1134 so as to create virtual electrodes 1136, a nonuniform electric field may be generated between the virtual electrodes 1136, thereby creating DEP forces to act on the particles in the manipulation chamber 1110. It should be understood that the light beams 1190 are depicted schematically and that a footprint of light that illuminates substantially the entire area corresponding to a virtual electrode 1136 shown in FIG. 14B may be created from each respective beam 1190.

Thus, the exemplary embodiment of the manipulation chamber 1110 of FIGS. 14A and 14B, may permit nonuniform electric fields, and resulting DEP forces, to be created between virtual electrodes within the same plane (e.g., virtual electrodes 1136) or between electrodes in differing planes (e.g., electrode 1122 and electrode/photoconductor 1132, 1134). A switch, which may be programmable, may be provided to activate either the power source 1160 electrically coupling the electrodes 1122 and 1132 or the power source 1170 electrically coupling the electrodes 1133 and 1135. Moreover, it is envisioned that only one power source may be used and switched so as to apply a potential to either electrodes 1122 and 1132 or 1133 and 1135. In this latter case, DEP could only occur in the direction corresponding to the coupled electrodes. On the other hand, if two power sources are used, it may be possible to apply a potential simultaneously to the electrodes 1122 and 1132 and the electrodes 1133 and 1135, which may permit manipulation of the particles in two dimensions.

By way of example only, in a first mode of operation, the AC power source 1160 may be used to apply an electric potential between electrode 1122 and electrodes 1133 and 1135, as shown in FIG. 14A. In this mode of operation, the light source 1180 may be used to illuminate the photoconductive layer 1134, such as, for example, via scanning or focused light beams, and the manipulation chamber 1110 may operate so as to induce optoelectronic manipulation (e.g., optoelectronically induced DEP) in a manner similar to various other manipulation chamber embodiments described herein, such as, for example, the embodiment of FIG. 1. A second mode of operation may include disabling power source 1160 and enabling power source 1170. In this mode, an electric potential from an AC power source may be applied between electrodes 1133 and 1135 and virtual electrodes 1136 may be activated by illuminating corresponding regions of the photoconductive layer 1134 with incident light, for example, in the pattern shown by 1190 in FIG. 14B. As a result of DEP forces created in the second mode of operation, manipulation of particles may occur between the photoactivated electrodes 1136. In yet another mode of operation, the power source of FIG. 14B may be a DC power source instead of an AC power source. In this case, the photoactivated electrodes 1136 will cause EP forces to be generated and thus the electrodes 1136 may be used to manipulate charged particles in the manipulation chamber 1110. The various modes of operation may occur concurrently, sequentially, intermittently, or any combination thereof in order to achieve desired separation, or other manipulation of particles in the manipulation chamber 1110. Those having ordinary skill in the art would understand how the coupling of the various electrodes and applied power sources may be altered in order to achieve desired DEP and/or EP manipulation of particles.

A manipulation chamber, such as, for example, manipulation chamber 1110, which permits modulation of a nonuniform electric field and DEP forces between virtual electrodes in the same plane may provide advantages for DEP application such as, for example, applications for which cell levitation is desired. For example, by applying an AC bias between electrodes 1133 and 1135 of FIG. 14, a negative DEP force that declines with distance away from the electrodes (e.g., toward upper substrate 1120) may be created. Thus, particles in the chamber 1110 having negative Clausius-Mosotti values will be repelled to a height in the chamber (as measured from photoconductive surface 1134) at which the DEP force is balanced by the gravitational force. Using an array of interdigitated virtual electrodes, such as electrodes 1136, where an AC bias is imposed between adjacent electrodes may levitate all the particles experiencing negative DEP above the array. The final levitation height of a particle depends on the balance of the DEP and gravitational forces acting on that particle. The negative DEP force is not uniform above the array, but is strongest near an electrode edge and weaker over the center of individual electrodes and in the gaps between electrodes.

Virtual electrodes such as electrodes 1136 of FIG. 14B may thus be used in a manner similar to patterned electrodes to achieve cell levitation, which has been described in Das et al., "Dielectrophoretic Segregation of Different Cell Types on Microscope Slides," *Anal. Chem.* May 1, 2005, vol. 77, pp. 2708-2719, incorporated by reference herein. Various degrees of control over the cell levitation may be obtained by altering the positions and shapes of the virtual electrodes, and/or the intensity of the light illuminating the photoconductive layer to create the virtual electrodes. Advantages to using virtual electrodes for cell levitation, rather than patterned electrodes, may include reduction in fabrication costs and ability to observe a majority of the manipulation chamber.

According to yet another exemplary aspect, a series of parallel, stationary virtual electrodes could be formed by illuminating respective regions of the photoconductive layer 1134 and an AC bias could be applied between the electrode 1122 and the virtual electrodes such that the electric field is modulated between each virtual electrode and the electrode 1122. When using this configuration, it may be desirable to minimize the gap between the virtual electrodes in order to minimize potential dead regions corresponding to locations without electric field lines where particles may become trapped.

Although in the description of the various optoelectronic manipulation devices and techniques above, the light source used to illuminate the photoconductive surface and thereby generate the electric field and corresponding DEP force may be a light source of substantially uniform intensity, it is envisioned that light sources having varying intensity may be used. In this manner, assuming the conductivity of the photoconductor depends on the applied light intensity, it may be possible to vary the generated electric field along the surface of the photoconductor, and thus the resulting DEP force, by varying the light intensity that illuminates any particular location of the photoconductive surface. Reference may be made to Chiou et al., Sensors and Actuators, vol. 104, pp. 222-228, 2003, which is incorporated by reference herein, for information regarding light intensity modulated conductivity By way of example, as the light scans across the manipulation chamber, the intensity of the light source may be varied (e.g., in the direction of scanning) so as to alter the resulting electric field and DEP forces that are generated. The intensity of the light source may also vary in a direction perpendicular to the scanning direction (e.g. in the Y-direction depicted in FIG. 2). Thus, as the intensity of the projected light beam may vary in both the direction of scanning and in a direction perpendicular to the scanning direction, modification of the electric field generated by the illumination of the photoconductive surface can occur in two dimensions, as desired.

In contrast to existing techniques for sorting cells that rely on DEP forces created by patterned electrodes on a substrate surface subject to an increasing applied electric field in one direction along the substrate surface, use of the optoelectronic techniques with varying light intensity described herein permit variation of the generated electric field, and resulting DEP forces, in two dimensions as opposed to just one dimension. Thus, the optoelectronically-induced DEP may provide increased flexibility and control over the modulation of electric fields, in terms of both strength and location. Further, the optoelectronic methodology does not require complex and/or costly fabrication of patterned electrodes (e.g., microfabrication) and/or high voltage power sources. Rather, the technique relies on variation of light intensity. Moreover, due to the transparent configuration of the manipulation chambers used in optoelectronic techniques, subsequent cell analysis may be facilitated by enabling the entire manipulation chamber to be observed. In contrast, in techniques using surfaces which have patterned electrodes, a relatively large portion of the patterned surface may not be viewable due to the presence of the electrodes.

Thus, various advantages may be achieved by an optoelectronic manipulation chamber configured such that the light intensity illuminating the photoconductive surface is variable, either in a direction of scanning, a direction perpendicular to scanning, or both. Such advantages include, but are not limited to, the ability to generate numerous virtual electrode configurations by controlling location and/or intensity of illumination on the photoconductive surface, the ability to move the location of such virtual electrodes within the same device by controlling the location and/or intensity of illumination, and relatively inexpensive and simplified device configurations. It should be further noted that according to various embodiments, optoelectronic manipulation chambers disclosed herein can achieve most, if not all, configurations (e.g., location, shape, field strength, etc.) of patterned electrodes, as well as some configurations which patterned electrodes cannot achieve.

Figure 26A:
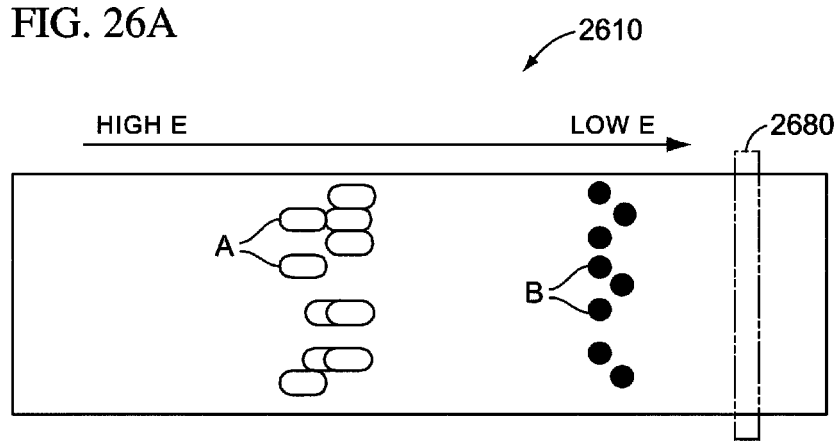
FIGS. 26A and 26B are schematic illustrations showing yet additional exemplary embodiments of optoelectronic manipulation of particles.
Figure 26B:
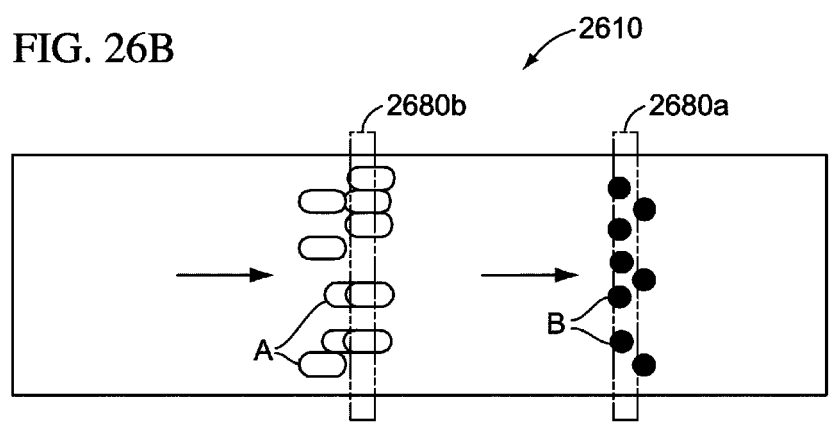

FIGS. 26A and 26B schematically depict an exemplary optoelectronic sorting technique that relies on varying the intensity of the incident light during a scanning process. The chambers 2610 of FIGS. 26A and 26B may have a configuration in accordance with various exemplary embodiments of the invention as disclosed herein. In FIG. 26A, the light beam 2680 may initially have a relatively high intensity which may produce a relatively strong electric field at locations of illumination of the photoconductive surface of the manipulation chamber 2610. The intensity and scanning speed of the light beam 2680 may be selected so as to be sufficient to overcome the viscous drag force on all particles in the chamber 2610 or of particles of interest in the chamber. The intensity, and thus electric field, may be reduced during the scanning process, for example, as the beam 2680 moves from left to right across the chamber 2610 as shown in FIG. 26A. As the intensity is reduced, particles with higher viscous drag as compared to DEP force, such as particle type A labeled in FIG. 26A, will escape from the beam 2680 before particles with lower viscous drag as compared to DEP force, such as particle type B labeled in FIG. 26A. This results in differing displacements (dielectrophoretic movement) of particles of particle type A as compared to particles of particle type B, as illustrated in FIG. 26A, thus enabling particle type A particles to be separated from particle type B particles.

In another exemplary technique illustrated in FIG. 26B, a plurality of scanning beams 2680*a* and 2680*b* may be utilized with each having an intensity that differs from the other. For example, in FIG. 26B, beam 2680a may have a relatively low intensity and beam 2680b may have a relatively high intensity. In this case, beams 2680a may be utilized to collect particles having relatively low viscous drag as compared to DEP force acting thereon. The beam 2680b of higher intensity, and thus higher DEP force, may then be used to trap particles having relatively higher viscous drag acting thereon. Those skilled in the art would understand that a series of any number of scanning beams of differing intensities could be used to separate various particle types. The series of beams could be used as a filter to collect particles of a particular type in each respective beam and those collected particles could be moved to collection areas within or outside the chamber by moving the respective beam trapping the particles and/or using various collection techniques described above. Further, although the embodiment of FIGS. 26A and 26B uses positive DEP force to move and sort cells, those skilled in the art would understand, based on the various teachings provided herein, how to utilize negative DEP forces for similar manipulation and sorting of particles. In some cases, negative DEP may reduce cell adhesion and damage.

Such optoelectronic scanning utilizing scanning beams of differing DEP strengths was used by the inventors to separate Hela and Jurkat cells from one another. Jurkat cells were labeled with CellTracker (Invitrogen) according to the manufacturer's recommendations. Hela and labeled Jurkat cells were washed in an isotonic buffer (8.5% sucrose, 0.3% dextrose) and resuspended in the same buffer. The cells were mixed and the conductivity of the mixture was adjusted to about 1.7 mS/m with growth media (Dulbecco's Modified Eagle's Media). The mixture was supplied to an optoelectronic scanning chamber and subjected to optoelectronic scanning with 2 beams of 633 nm light scanned at differing speeds ranging from about 3 micrometers/sec to about 11 micrometers/sec. The leading beam was about 15 micrometers wide and the trailing beam was about 23 micrometers wide. Lines of differing widths resulted in differing DEP forces experienced by the cells. At scanning speeds of about 8.7 μm/sec, Jurkat cells followed the leading beam, whereas Hela cells were dropped by the leading beam. Dropped Hela cells were then trapped by and followed the thicker trailing beam. Thus, the scanning beams of differing DEP strengths were generated in the optoelectronic scanning chamber and the beams were used to separate cells of different types.

FIGS. 29A-29D illustrate another exemplary embodiment of a scanning technique in which particle sorting may be achieved by a series of beams of differing intensities. In the exemplary embodiment of FIGS. 29A-29D, scanning may be performed within a continuous pattern such as a "race-track" pattern, as shown. Such a continuous, race-track pattern of scanning may be useful in circumstances where the distance and/or time required for particles to escape from a scanning light beam, for example, a light beam of lower intensity that does not overcome the viscous drag acting on a subset of particles, varies and may not be predictable. Providing a continuous scanning loop (e.g., race track), may enable the desired separation and sorting of all particles since the light beams can repeatedly scan around the loop until the desired separation of the particles occurs, as will be explained in further detail below.

Figure 29A:
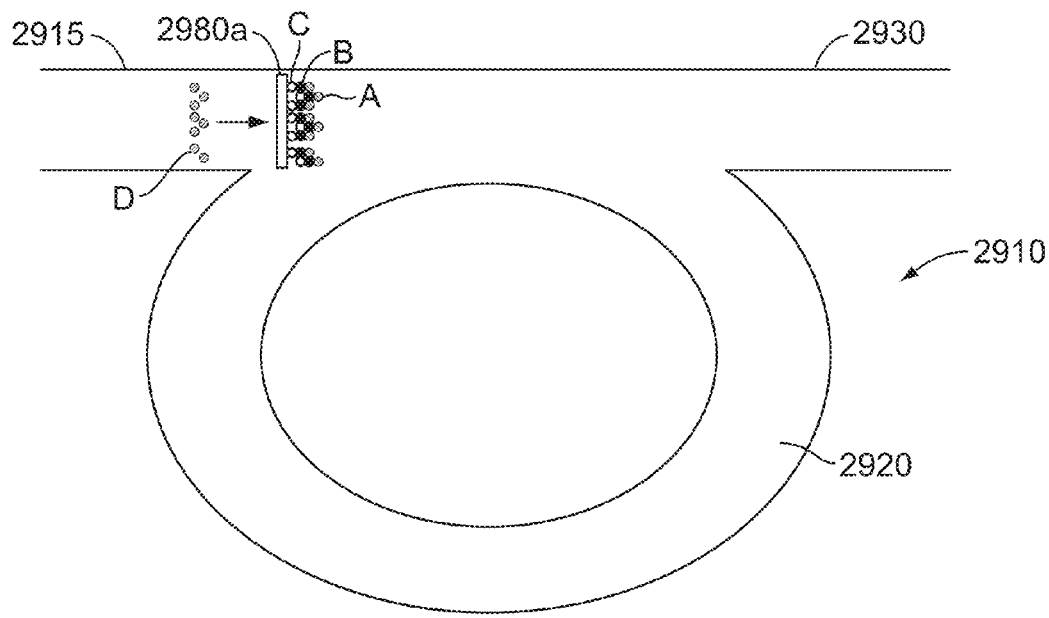
FIGS. 29A-29D are top schematic views of an exemplary embodiment of a technique for sorting particles utilizing optoelectronic scanning.
Figure 29B:
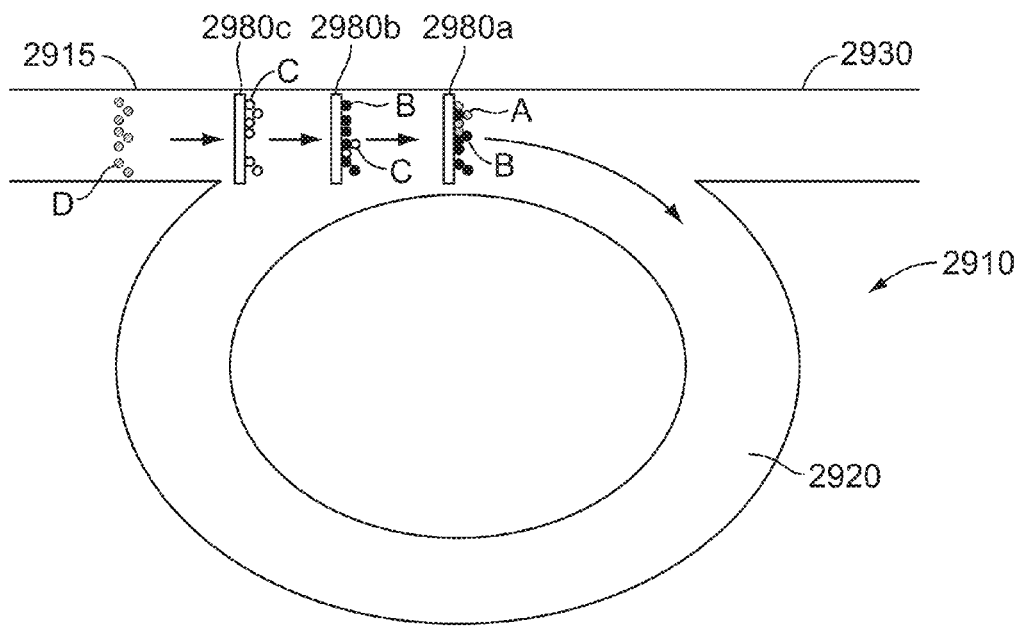
Figure 29C:
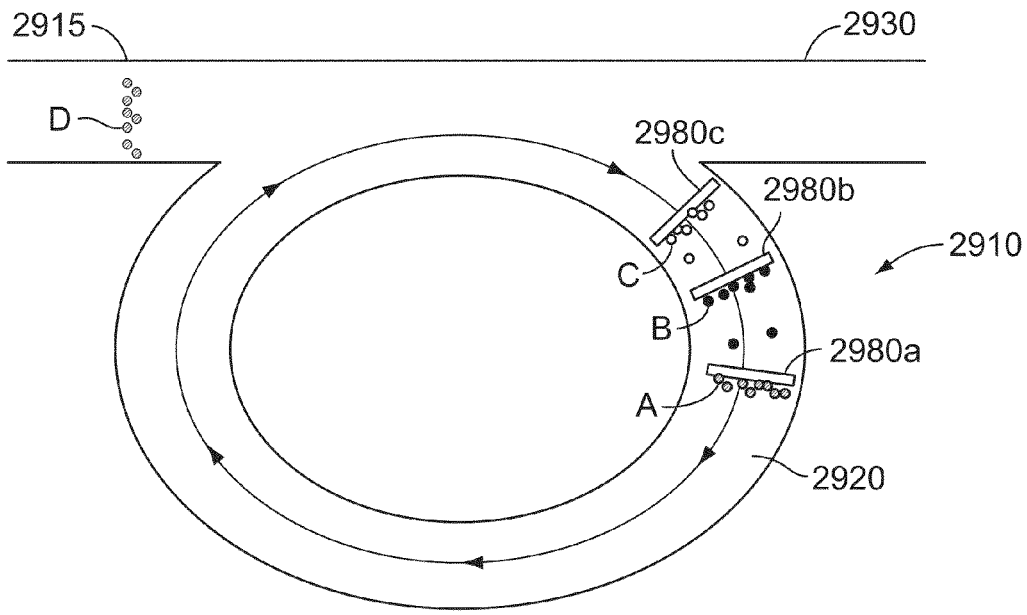

In various exemplary embodiments, a plurality of differing types of particles A, B, C, and D, (e.g., cells) may be introduced into an optoelectronic scanning chamber 2910 at an input area, as shown in a top view of the chamber 2910 in FIG. 29A. An initial scanning light beam 2980a may begin to move across the particles A, B, C, and D. As shown in FIG. 29A, the frequency of the initial scanning light beam 2980a may be selected so as to impose a cut off wherein undesired particles D do not enter the portion of the scanning loop 2920 past the input area 2915. Such a "cut off" frequency for the initial light beam is optional and in an alternative all of the particles may be initially entrained by the light beam 2980a so as to be swept into the scanning loop 2920. The initial scanning light beam 2980a may be followed by a series (e.g., two shown in FIGS. 29B-29C) of scanning light beams 2980b and 2980c of differing (e.g., progressively increasing) field intensities. Although FIGS. 29B and 29C depict a series of three scanning light beams 2980a, 2980b, and 2980c, those having skill in the art would understand that the number of light beams may vary. For example, any plurality of light beams may be used and chosen based on, for example, the number of particle types it is desired to sort and trap.

Figure 29D:
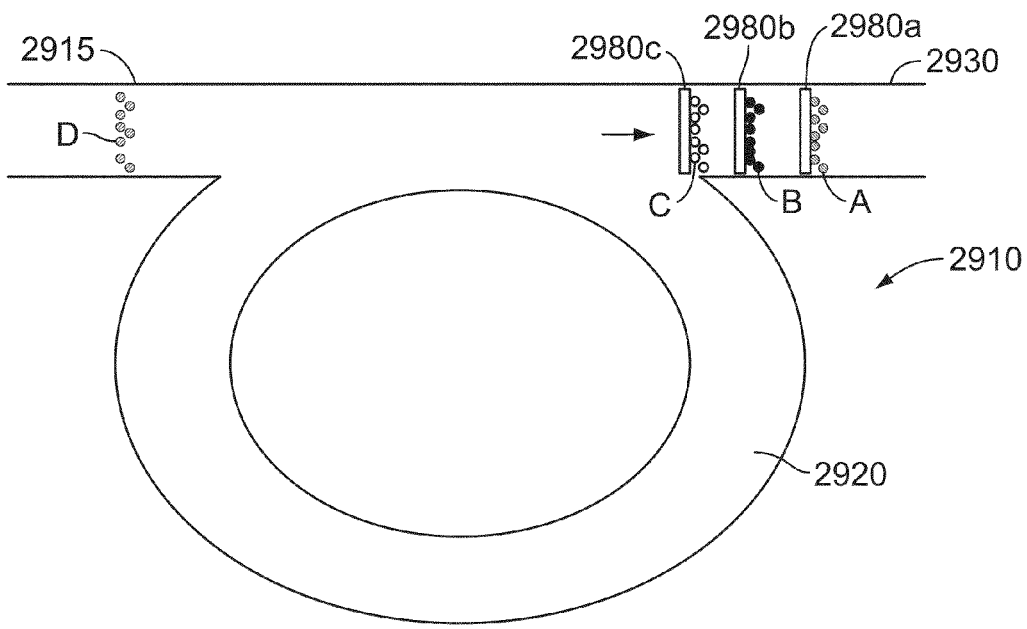

Thus, in the exemplary embodiment of FIGS. 29A-29D, three particle types A, B, and C, are sorted and respectively trapped via the DEP force created by the three scanning light beams of differing field intensities 2980a, 2980b, and 2980c. The particles A, B, and C, are "trapped" by one of the scanning light beams 2980a, 2980b, and 2980c when the field produced at the location of the virtual electrode created by the light beam 2980a, 2980b, and 2980c generates a DEP force sufficient to overcome the viscous drag associated with each particle type A, B, or C. At the beginning of the scanning, as shown in FIG. 29B, for example, particles of differing types may be moved together by one of the scanning beams 2980a, 2980b, or 2980c. For example, FIG. 29B depicts particles of types A and B being trapped by the light beam 2980a of lowest intensity and particles of types B and C being trapped by the light beam 2980b of medium intensity compared to light beams 2980a and 2980c. This may occur due to the variation in time and/or distance required for the particle types that experience higher viscous drag to escape the scanning light beam having a lower field intensity. The loop 2920 that the scanning light beams 2980a, 2980b, and 2980c travel around permits the light beams to continuously scan until sufficient distance and time has occurred to permit the desired separation between the differing particle types A, B, and C. Thus, as shown in FIG. 29C, the scanning light beams 2980a, 2980b, and 2980c may continue around the loop 2920 in the direction of the arrows shown until the desired separation of the differing particle types A, B, and C, is accomplished and each particle type A, B, and C is entrained in the appropriate respective light beam 2980a, 2980b, 2980c. Upon achieving this desired separation and entrainment, the scanning light beams 2980a, 2980b, and 2980c, with their respective entrained particle types A, B, and C may be moved out of the loop 2920 and to an exit area 2930, as illustrated in FIG. 29D, such that the particles A, B, and C, may be further collected and/or otherwise processed or analyzed.

Varying the frequency of the applied electric field may also vary the DEP force on particles, as the permittivity of both the particles and the medium depend on frequency and thus so does the Clausius-Mosotti value. At a frequency called the cross-over frequency, which is different for each particle type, the induced dipole on a particle is zero and $F_{DEP}$ is zero. Particles may experience negative or positive DEP at frequencies lower or higher than the cross-over frequency. Thus, both magnitude and direction of the DEP force experienced by a particular particle type may be altered by varying the applied frequency.

Figure 27A:
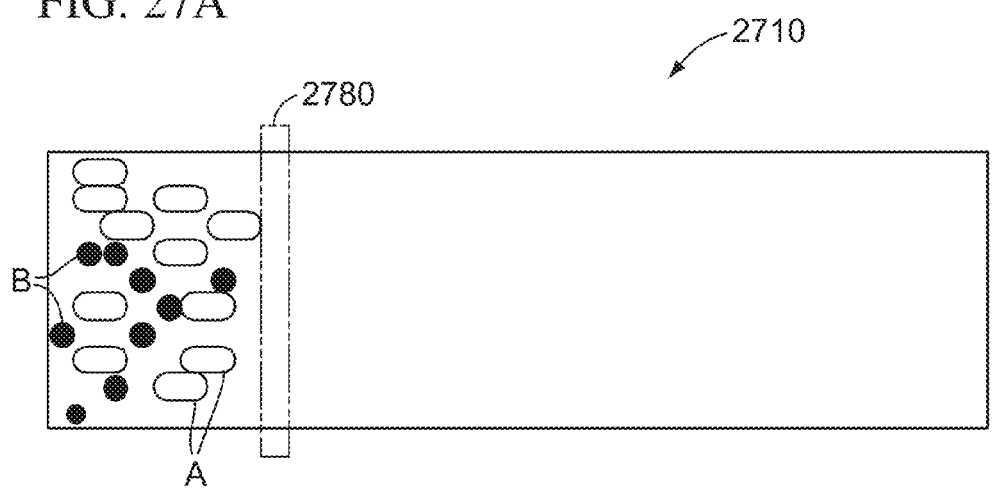
FIGS. 27A and 27B are schematic illustrations showing yet further exemplary embodiments of optoelectronic manipulation of particles.
Figure 27B:
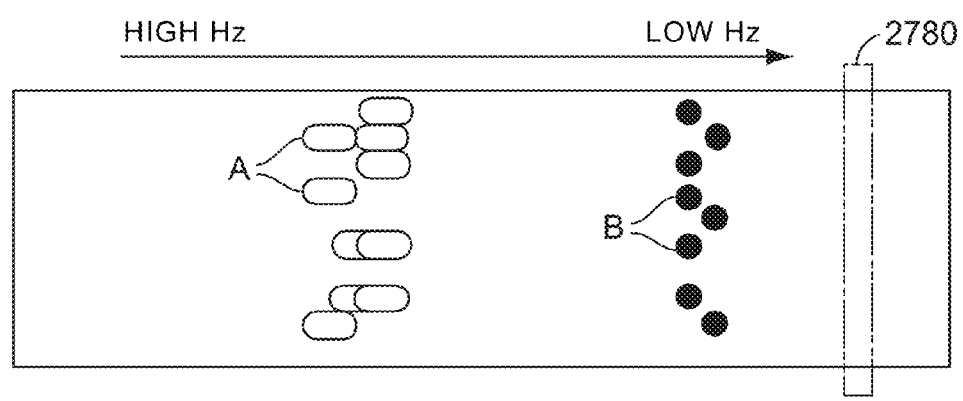

FIGS. 27A and 27B schematically depict exemplary optoelectronic sorting techniques that rely on varying the frequency of the applied electric field between the electrodes in a manipulation chamber in order to separate particles of differing particle types, such as A and B in FIGS. 27A and 27B. Initially, as shown in FIG. 27A, a light beam 2780 of an optoelectronic manipulation chamber 2710 may be operated at relatively high frequency, for example, greater than about 300 kHz such that a relatively strong electric field occurs in the proximity of the light beam 2780. Due to the relatively strong electric field, as shown in FIG. 27A, all of the particle types A and B may be dragged along in a group with the light beam 2780, assuming positive Clausius-Mosotti values in this example. As scanning continues, the frequency of the applied electric potential may be varied, for example, progressively decreased, as shown in FIG. 27B. As the frequency reaches the cross-over frequency for each particle type, that particle type will cease to migrate and as the frequency further declines, that particle type will experience a repelling, negative DEP force. Particle types experiencing negative DEP as a result of the variation in the frequency, may escape through gaps provided down the length of the scanning light beam 2780. That is, the light beam 2780 could be configured as a plurality of individual illuminated portions separated by gaps of unilluminated portions between adjacent illuminated portions down the length of the beam 2780. Alternatively, for a solid light beam without such gaps, as shown in FIGS. 27A and 27B, and scanning at a sufficiently high speed, the viscous drag on the particles of negative or weaker DEP may overcome the DEP force near the particles' threshold velocity such that the particles escape the scanning light beam.

Thus, as shown in FIG. 27B, differing particle types A and B may be collected in groupings based on cross-over frequency by altering the frequency of the applied electric field during scanning. By correlating the position along the chamber of the scanning beam 2780 with the applied frequency, the cross-over frequency of the differing particle types A and B also may be determined.

It should be understood that varying the intensity of the light and the frequency of the applied field either simultaneously or sequentially, with or without scanning, in an optoelectronic manipulation chamber may be utilized to potentially gain additional separation of differing particle types. Moreover, a two-dimensional separation may be achieved, for example, wherein an initial particle population is confined to a predetermined area, such as, for example, a corner of the chamber. Separation using field (intensity) modulation scanning could be used in a first dimension separation/sorting scheme while frequency modulation scanning could be used in a second dimension. In an exemplary aspect, pulsing light may be used so as to alter the intensity.

According to various exemplary embodiments, one or more interior surfaces of an optoelectronic manipulation chamber may be provided with surface modification treatments such that portions of the surface become non-selectively or selectively adsorptive. In an exemplary aspect, different areas of the chamber surface associated with the substrate comprising the photoconductive material may be treated with different modifiers (e.g., ligands, antibodies, smart polymers, lectins, etc.) so as to cause different types of particles to bind to the different areas after separation of the particle types via optoelectronic DEP. Examples of suitable materials that may be used to modify the surfaces of the chamber are set forth in U.S. patent application Ser. No. 10/979,645, incorporated by reference herein.

In yet another exemplary aspect, an optoelectronic manipulation chamber according to exemplary aspects of the invention may include electric field concentrators. For example, the chamber may incorporate insulating material, such as, for example, patterned insulating obstacles configured to produce electric field concentrations or otherwise alter the electric field within the chamber. Those with skill in the art would understand a variety of materials and techniques that may be used to form such insulating structures within the chamber in order to alter the electric field therein.

As discussed above, a variety of materials for the various components of optoelectronic manipulation chambers suitable for a variety of applications, including, for example, scanning, identifying, sorting, collecting, and/or otherwise manipulating small particles, such as, for example cells, including stem cells, DNA, and/or other biological material. An embodiment of an optoelectronic manipulation chamber that may provide advantages over other optoelectronic manipulation chamber embodiments is set forth below in the following example. In addition to the manipulation chamber materials, various methods of fabrication and data obtained by performing various tests on manipulation chamber components are described. It should be understood that the optoelectronic manipulation chamber described in the following example could be used for any of the applications described herein.

Example

Figure 15:
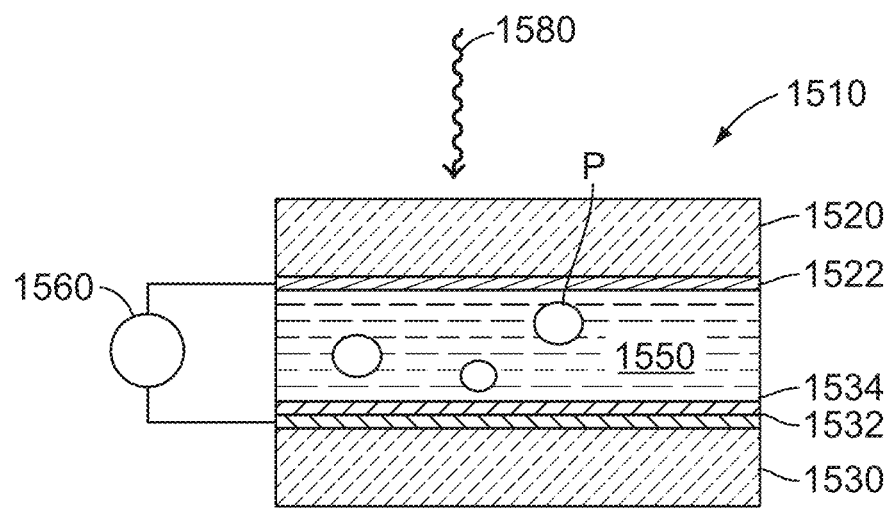
FIG. 15 is a side view of another exemplary embodiment of an optoelectronic manipulation chamber.

FIG. 15 is a side view of a manipulation chamber comprising a first substrate 1520 made of glass and having a PEGylated transparent gold electrode 1522 thereon. The manipulation chamber 1510 further comprises a second substrate 1530 made of glass with a metal electrode 1532 made of ITO deposited thereon in a relatively thin layer, followed by a PEGylated SiO$_2$ photoconductor 1534.

To obtain the PEGylated gold electrode layer 1522, a gold electrode was first deposited on the substrate 1520 via vapor deposition in a vacuum chamber. It is envisioned, however, that other suitable deposition techniques may be employed as well. The gold electrode may be deposited in a relatively thin layer having an average thickness ranging from about 30 angstroms to about 200 angstroms, for example, about 50 angstroms to about 100 angstroms. For the chamber of the present example, the gold electrode layer ranged from about 70 angstroms to about 80 angstroms thick.

As those skilled in the art will appreciate, deposition of the gold electrode layer does not result in a layer of uniform thickness, but rather a noncontinuous layer that is interconnected, for example, like a series of islands on the surface of the glass substrate 1510. By way of example, the gold electrode layer may permit about 10% to about 80% of light to pass through the layer. As will be discussed further below, the gold electrode layer formed in accordance with this example, and as described below with reference to the process illustrated in FIG. 16, permitted approximately 60% of transmitted light to pass therethrough.

Following deposition of the transparent gold electrode (TGE) on the glass substrate 1520, the gold electrode may be subject to a PEGylation process in which a PEG group is chemically bonded (e.g., covalently bonded) to the surface of the deposited gold layer. The surface of gold is relatively easily modified by such a PEGylation process. The term "PEGylation" is used herein to refer to a process or processes that covalently bond poly(ethylene glycol) onto a surface. The resulting PEGylated transparent gold electrode 1522 results in an electrode in which nonspecific adsorption of biomolecules may be reduced (e.g., minimized).

The use of a transparent gold electrode layer may permit operation of the manipulation chamber at a lower AC frequency and/or with a DC power source. Other electrode materials, such as, for example, ITO, may become oxidized and thereby reduced to an insulator when operated at relatively low AC frequencies or under DC current if the DC power source is coupled incorrectly. Thus, manipulation chambers using ITO electrodes are typically operated at relatively high AC frequency. Because metallic gold is highly conductive and it cannot be reduced any further, it may be used in conjunction with relatively low AC frequency and/or DC power sources, in addition to being used with high AC frequency power sources.

Figure 16:
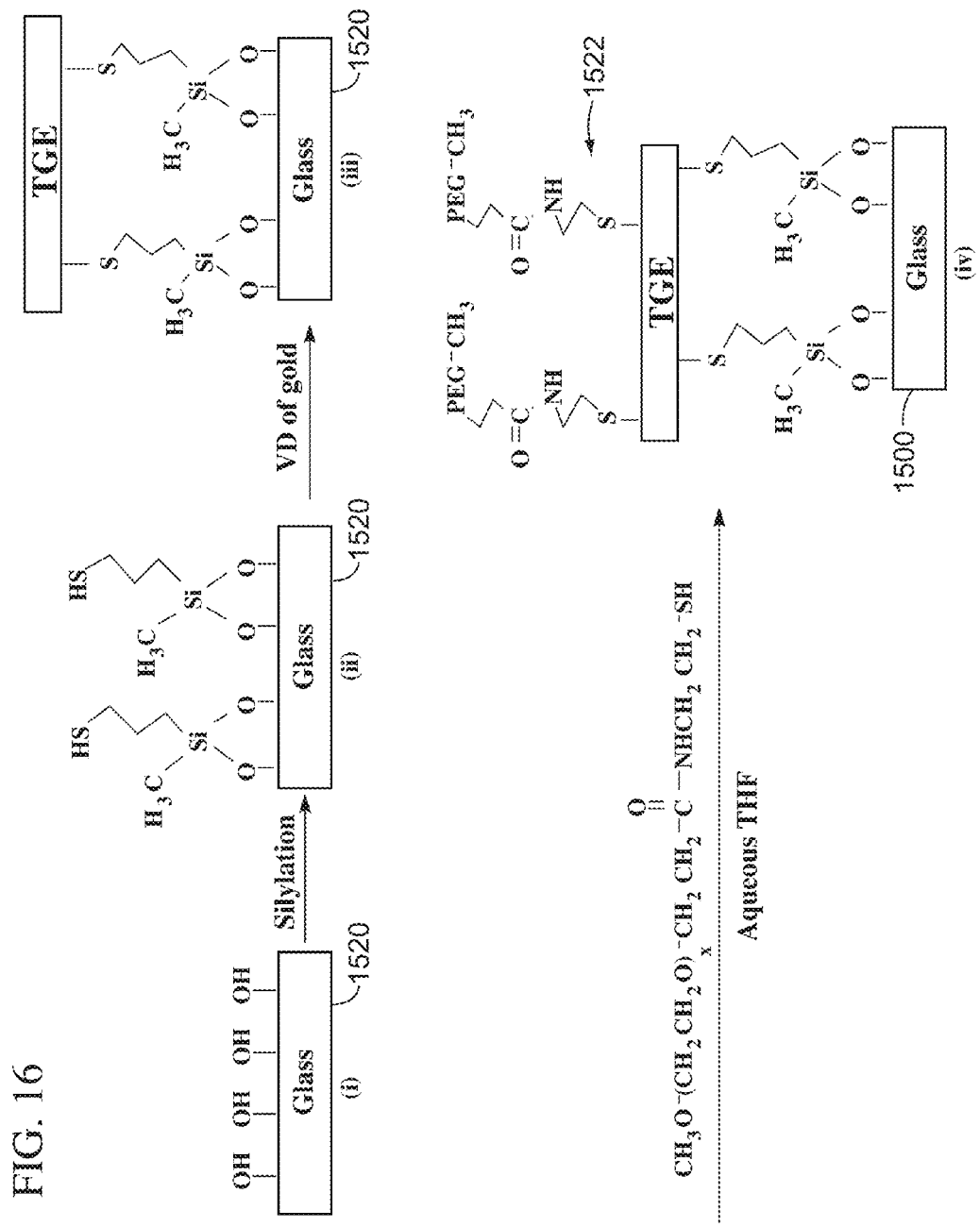
FIG. 16 is a schematic representation of exemplary steps for fabricating a substrate with a PEGylated transparent gold electrode layer.

FIG. 16 illustrates steps which were used to fabricate the PEGylated transparent gold electrode 1522 on the glass substrate 1520. Referring to FIG. 16, the glass substrate 1520 was first cleaned so as to remove impurities, such as, for example, organic impurities. A Piranah solution was used to clean the glass substrate 1520, The Piranah solution enhances surface density of silanol groups with OH groups bonded to the glass substrate surface, as shown in step 16(i) in FIG. 16. After cleaning the glass substrate 1520, a silylation process was used to treat the surface of the substrate 1520 on which the gold electrode layer is deposited. As shown in step 16(ii), the mercapto-containing silylating agent (obtained from Gelest, Inc.) reacts with the OH groups on the surface of the glass, resulting in the incorporation of surface hydrogen sulfide groups (HS). The silyation process ultimately provided good adhesion of the gold to the glass substrate because the formed HS groups (e.g., mercapto groups) react and form chemical bonds with gold.

After the silylation process, the gold was deposited on the glass substrate via a vapor deposition process. As shown in step 16(iii) of FIG. 16, the gold was deposited so as to achieve a transparent gold electrode layer (TGE). The mercapto functional groups also resulted in strong adhesion of the transparent gold layer to the glass surface, as shown by the resulting covalent bond formed between the deposited TGE and the sulfur (S) in step 16(iii).

The resulting glass substrate with a TGE deposited layer in accordance with the exemplary steps above demonstrated good adhesion of the TGE to the glass substrate. For example, the resulting substrate with a TGE deposited layer, as shown in step 16(iii) of FIG. 16 passed a standard ASTM D3359-02 "Scotch tape" test. In various produced samples, the thickness of the TGE ranged from about 71 angstroms to about 78 angstroms, and the sheet resistance was about 60 omhs/sq, representing relatively high conductivity.

Figure 17A:
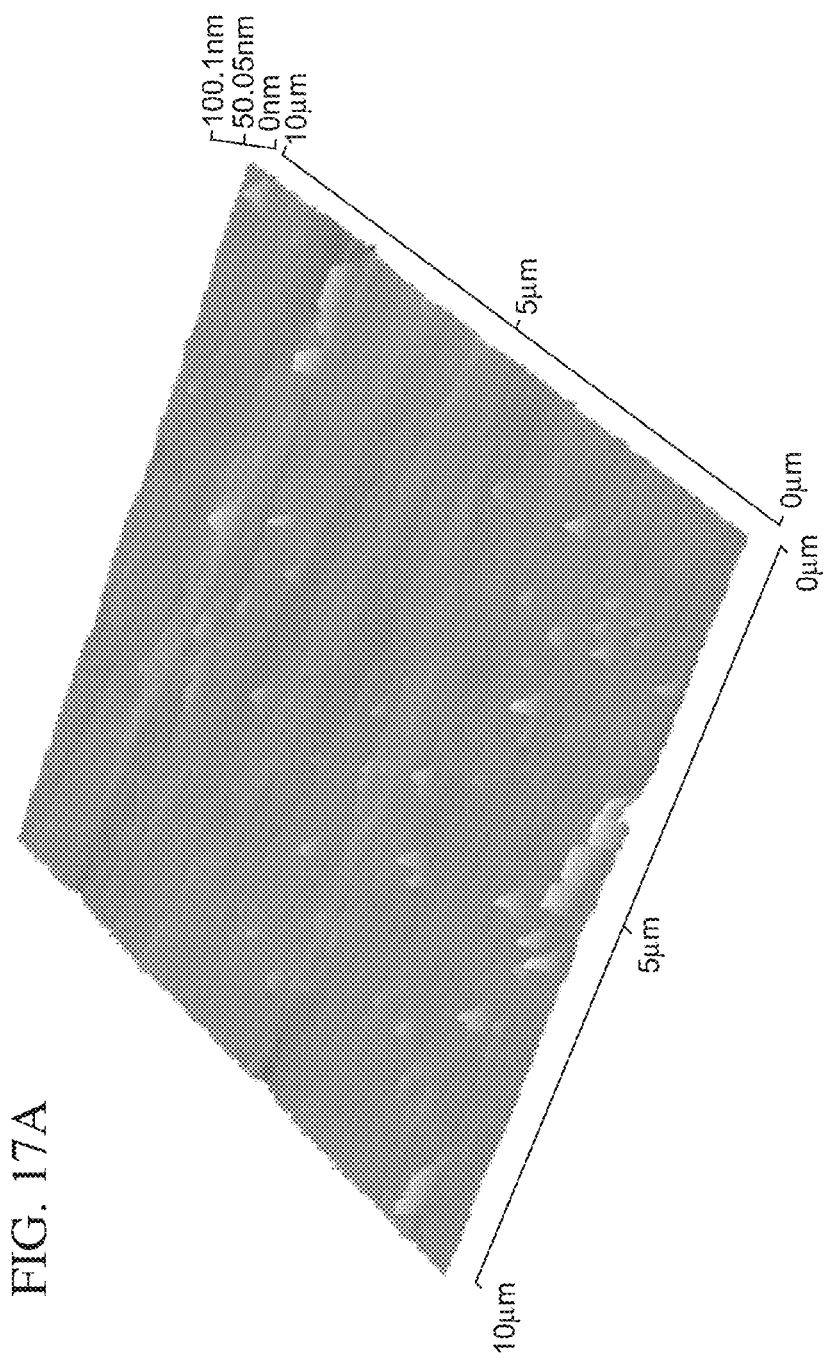
FIGS. 17A-17C show perspective views of a substrate surface after being subjected to the various surface treatment steps of FIG. 16
Figure 17B:
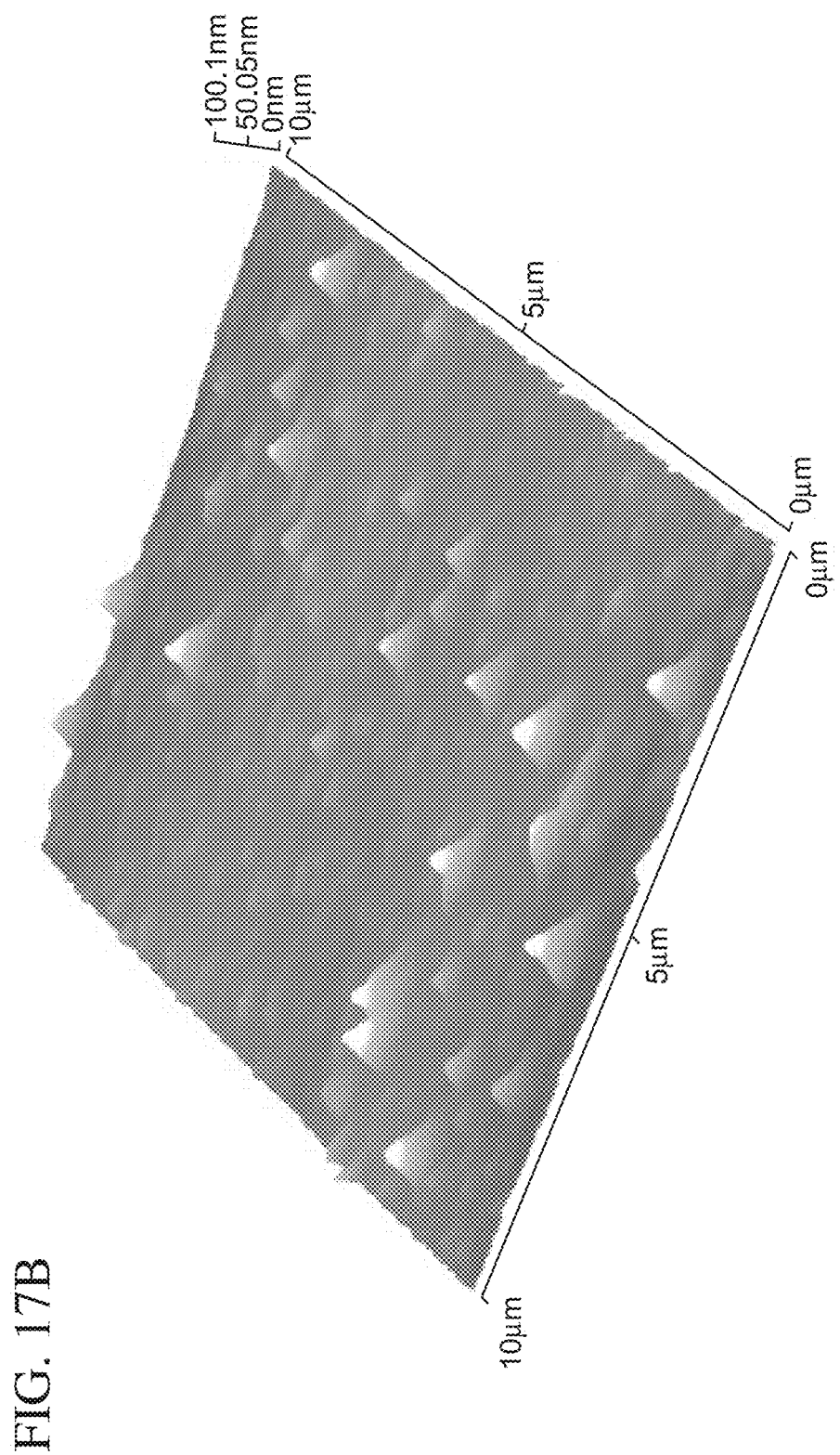

FIGS. 17A and 17B show perspective views of a 10 micron by 10 micron portion of a glass substrate (e.g., slide) after being subject to the silylation process and vapor deposition process of FIG. 16. That is, FIG. 17A shows a perspective view of a portion of the glass substrate resulting from the cleaning and silylation process as illustrated in step 16(ii) of FIG. 16, and FIG. 17B shows a perspective view of the portion of the glass substrate after the cleaning, silylation, and deposition processes as illustrated in step 16(iii) of FIG. 16. The pictures in FIGS. 17A-17C were obtained via Atomic Force Microscopy (AFM).

Referring again to FIG. 16, after the transparent gold electrode (TGE) was deposited on the surface of the glass substrate 1520, the deposited gold layer was subject to a PEGylation process, which may protect the surface facing the interior of the manipulation chamber against nonspecific passive adsorption of biomolecules. To perform the PEGylation, the gold surface was exposed to an aqueous tetrahydrofuran (THF) containing a mercapto-functionalized poly(ethylene glycol) (molecular weight 5723 Da, obtained from Nektar), with x equal to about 126, as shown by reference number 1521 in FIG. 16. In various exemplary aspects, the PEGylation of the gold surface may be achieved with x in FIG. 16 ranging from 5 to 1000, for example, from 10 to 300, or, for example, from 20 to 200. Those skilled in the art would be able to determine the value of x to achieve desired surface features. As with step 16(ii), the mercapto groups form a strong covalent bond with the gold electrode layer via the sulfur (S) bond, as shown in step 16(iv). The resulting gold electrode layer in step 16(iv) of FIG. 16 has poly(ethylene glycol) groups (PEG) bonded to the gold. The resulting PEGylated TGE layer 1522 resulted in a sheet resistance of about 20 ohms/sq.

Figure 17C:
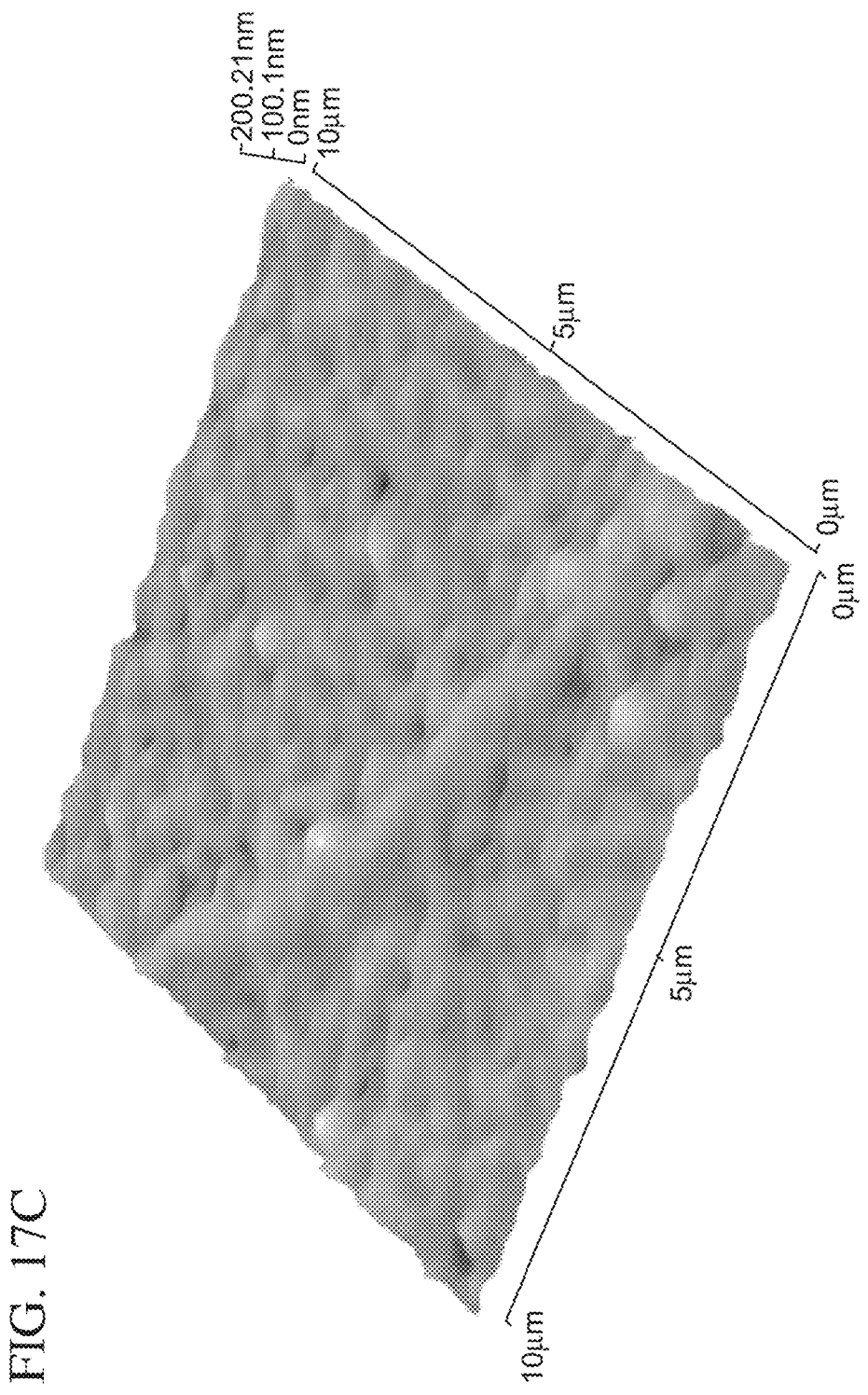

FIG. 17C shows a perspective view of the portion of the glass substrate of FIGS. 17A and 17B after being subject to the cleaning, silylation, vapor deposition, and PEGylation process of FIG. 16. Thus, FIG. 17C shows resulting substrate of step 16(iv) of FIG. 16. When compared with FIG. 17B, the PEGylated TGE has a smoother surface.

Figure 18:
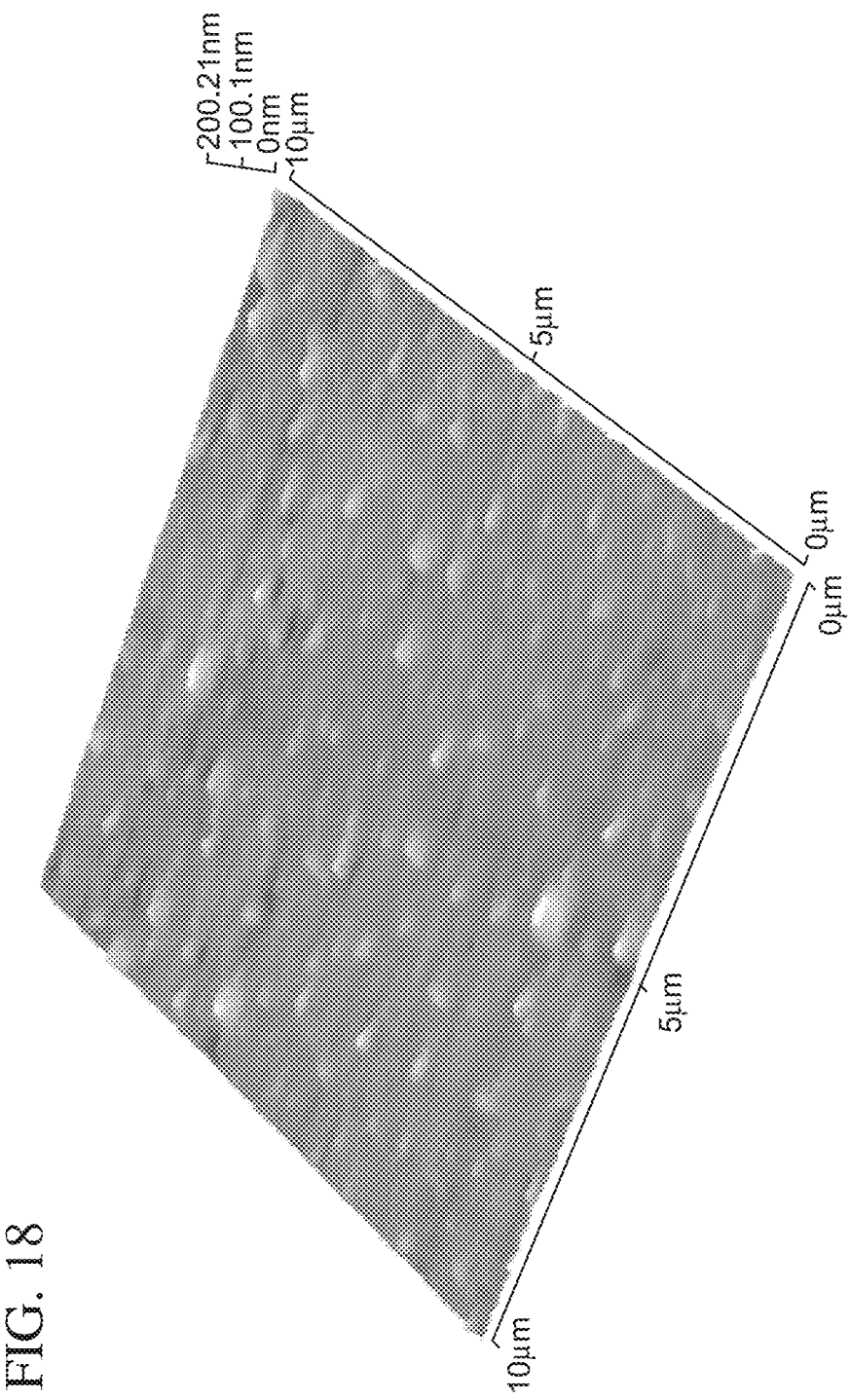
FIG. 18 is a partial, perspective view of a PEGylated transparent gold electrode substrate surface after having been exposed to 10×BSA (bovine serum albumin)

FIGS. 18-22 present data and results of various tests that were performed on glass substrates processed in accordance with FIG. 16 so as to obtain a PEGylated TGE layer deposited thereon. FIG. 18 shows a perspective view of such a processed substrate after exposure of the PEGylated TGE surface to a 10× bovine serum albumin (BSA) (e.g., a concentrate solution containing 1 mg/mL of BSA, whereas 1×BSA contains 0.1 mg/mL of BSA). As BSA is a protein, this BSA test may be used to observe the nonspecific passive adsorption characteristics of the surface.

Figure 19:
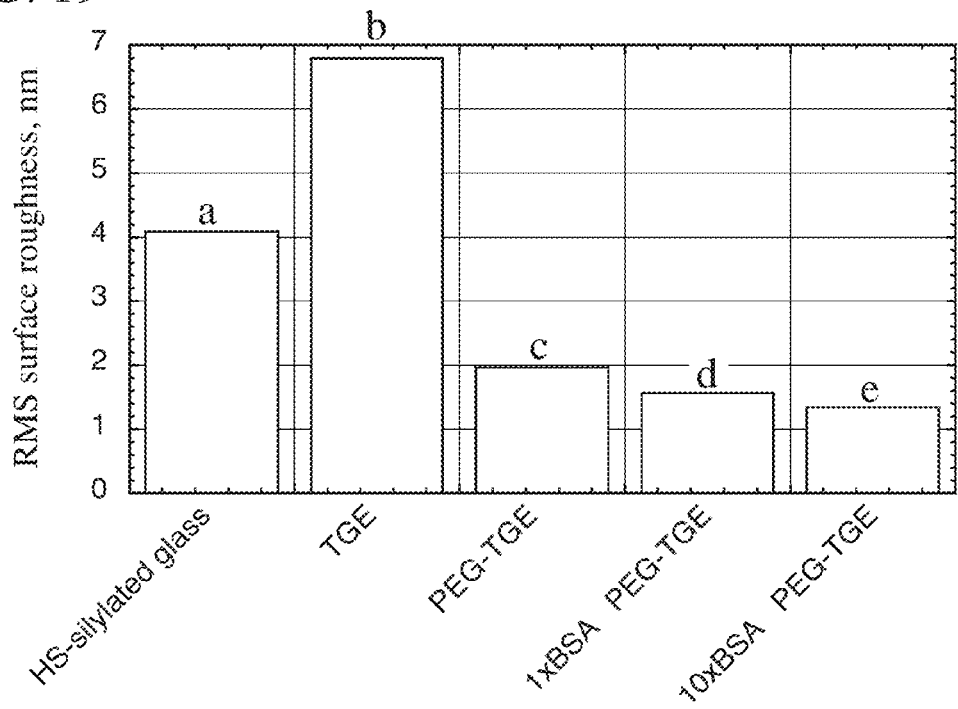
FIG. 19 is a chart comparing surface roughness measurements of various surfaces.

FIG. 19 shows a comparison of the surface roughness that resulted from subjecting the glass substrate to various treatment processes, including the resulting surfaces corresponding the various steps 16(ii)-16(iv) shown in FIG. 16. The surface roughness was measured by Atomic Force Microscopy (AFM) and is the root mean square (RMS) in nanometers. The results are taken over a 10 micron by 10 micron area of the surface of the treated substrate. Thus, the first bar to the left in FIG. 19 (labeled HS-silylated glass in FIG. 19), shows the resulting roughness of the substrate surface corresponding to step 16(ii) of FIG. 16, that is, after the substrate has been cleaned and subject to the silylation process in which the HS groups are bonded thereto. The second bar from the left in FIG. 19 shows the surface roughness of the substrate surface corresponding to step 16(iii) of FIG. 16, after the TGE layer has been deposited thereon (labeled TGE in FIG. 19), and the third bar from the left shows the surface roughness of the PEGylated TGE substrate surface corresponding to step 16(iv) of FIG. 16 (labeled PEG-TGE in FIG. 19). As can be seen by a comparison of the second and third bars, the PEGylation processing of the TGE results in a smoother surface (lower RMS surface roughness) than the TGE surface alone. The fourth and fifth bars from the left in FIG. 19 correspond to the exposure of the PEGylated TGE layer to 1×- and 10×-BSA, respectively (labeled 1×BSA PEG-TGE and 10×BSA PEG-TGE, respectively, in FIG. 19).

The slight decrease in roughness of the last two samples (i.e., the 1×BSA PEG-TGE and 10×BSA PEG-TGE samples, respectively, suggests a low degree of passive adsorption of BSA on the surface, resulting in some leveling (e.g., smoothing) effect on the surface.

Figure 20:
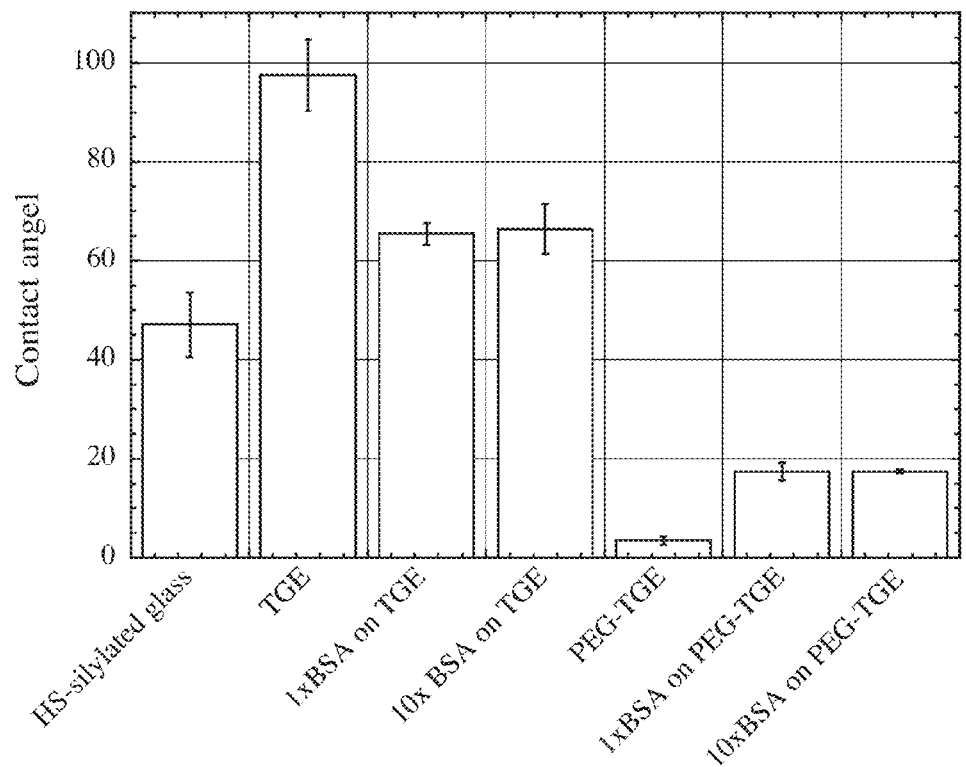
FIG. 20 is a chart comparing wettability of various surfaces.

FIG. 20 shows a comparison of surface wettability that resulted from subjecting the glass substrate to various treatment processes, including the resulting surfaces corresponding the various steps 16(ii)-16(iv) shown in FIG. 16. The results in FIG. 20 show measurements of contact angle for water applied to the various surfaces, with error bars for each also shown. In general, lower contact angles correspond to higher hydrophilicity/wettability and lower nonspecific adsorption due to hydrophobic-hydrophobic interaction. From left to right in FIG. 20, the bars correspond to the wettability measured for a glass substrate surface corresponding to step 16(ii) in FIG. 16 (labeled HS-silylated glass in FIG. 20); the glass substrate surface corresponding to step 16(iii) in FIG. 16 (labeled TGE in FIG. 20); the glass substrate surface corresponding to step 16(iii) in FIG. 16 in combination with an exposure to 1×BSA thereon (labeled 1×BSA on TGE in FIG. 20); the glass substrate surface corresponding to step 16(iii) in FIG. 16 in combination with an exposure to 10×BSA thereon (labeled 10×BSA on TGE in FIG. 20); the glass substrate surface corresponding to step 16(iv) in FIG. 16 (labeled PEG-TGE in FIG. 20); the glass substrate surface corresponding to step 16(iv) in FIG. 16 in combination with an exposure to 1×BSA thereon (labeled 1×BSA on PEG-TGE in FIG. 20); and the glass substrate surface corresponding to step 16(iv) in FIG. 16 in combination with an exposure to 10×BSA thereon (labeled 10×BSA on PEG-TGE in FIG. 20).

As can be seen from the results shown in FIG. 20, using a PEGylated TGE on the glass substrate yielded a surface having a relatively high wettability. The water contact angle for the PEGylated TGE surface (PEG-TGE) was significantly less than that of the TGE surface alone (TGE). In turn, non-specific adsorption of the PEGylated TGE was significantly reduced in comparison to the TGE surface. The reduction in nonspecific adsorption is demonstrated by the 1× and 10×BSA on TGE and on PEG-TGE results shown in FIG. 20.

Figure 21:
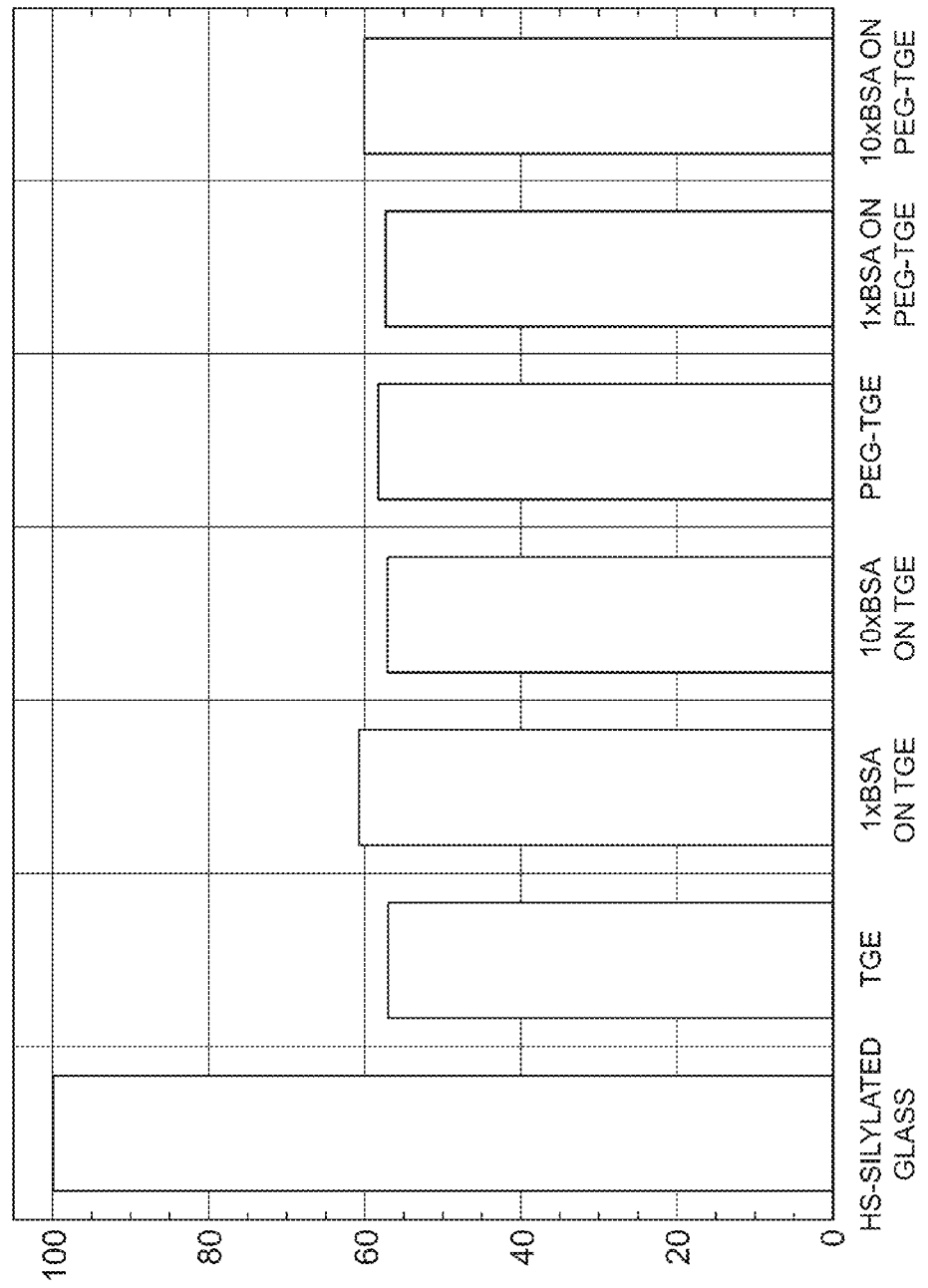
FIG. 21 is a chart comparing transparency measurements of various surfaces.

FIG. 21 shows results of measuring the transparency of the glass substrate after various surface treatment processes, including the resulting surfaces corresponding the various steps 16(ii)-16(iv) shown in FIG. 16. From left to right in FIG. 21, the bars correspond to the transparency measured for a glass substrate surface corresponding to step 16(ii) in FIG. 16 (labeled HS-silylated glass in FIG. 21); the glass substrate surface corresponding to step 16(iii) in FIG. 16 (labeled TGE in FIG. 21); the glass substrate surface corresponding to step 16(iii) in FIG. 16 in combination with an exposure to 1×BSA thereon (labeled 1×BSA on TGE in FIG. 21); the glass substrate surface corresponding to step 16(iii) in FIG. 16 in combination with an exposure to 10×BSA thereon (labeled 10×BSA on TGE in FIG. 21); the glass substrate corresponding to step 16(iv) in FIG. 16 (labeled PEG-TGE in FIG. 21); the glass substrate surface corresponding to step 16(iv) in FIG. 16 in combination with an exposure to 1×BSA treatment thereon (labeled 1×BSA on PEG-TGE in FIG. 21); and the glass substrate surface corresponding to step 16(iv) in FIG. 16 in combination with an exposure to 10×BSA thereon (labeled 10×BSA on PEG-TGE in FIG. 21).

The transparency was measured using a He—Ne laser light beam of 633 nm and 1.15 mW output. The intensity of the light passing through the HS-silylated glass slide was measured by a spectrophotometer and is considered to be 100% transparent. The results of the transparency measurements for each surface treatment shown in FIG. 21 are normalized with respect to the transparency measured for the HS-silylated glass. Thus, the HS-silylated glass is considered 100% transparent and the remaining results in FIG. 21 show transparency measurements as a percentage of the HS-silylated glass. As shown by the results of FIG. 21, the TGE surface and the various treatments to that surface (e.g., PEGylation and/or BSA treatments) yielded transparencies ranging from greater than about 55% of the HS-silylated glass to about just over 60% of the HS-silylated glass. As discussed above, for the various manipulation chambers and applications described herein, it may be desirable for the upper glass substrate and corresponding electrode surface thereon to have a transparency ranging from about 40% to about 80%. That is, in comparison with the HS-silylated, it may be desirable for the upper, first glass substrate provided with an electrode surface thereon (e.g., the nonphotoconductive substrate) to transmit about 40% to about 80% of incident light.

With reference to FIGS. 22A-22D, snapshots of real-time results of optoelectronic manipulation of polystyrene beads of about 20 microns in diameter suspended in a potassium chloride (KCl) solution prepared with deionized water and having a conductivity of 10 mS/m are shown. The optoelectronic manipulation chamber for which the results of FIG. 22 were obtained comprised a first, upper glass substrate having a PEGylated TGE thereon made according to the process of FIG. 16 and a second, bottom glass substrate having an ITO electrode layer, a α-Si:H photoconductive layer over the electrode layer, and a protective layer of silicon nitride over the photoconductive layer. It should be noted that for the results of FIGS. 22A-22D, the bottom substrate has the configuration disclosed in, for example, Chiou et al., "Massively parallel manipulation of single cells and microparticles using optical images," Nature, vol 436, July 2005, and not the configuration described above in the Example and which will be further described below with reference to FIGS. 24A and 24B.

The power source used for the manipulation of the polystyrene beads shown in FIGS. 22A-22D applied 18 volts at 90 kHz between the two electrodes of the chamber. An incident He—Ne laser light beam of 633 nm and 1.15 mW output was mapped onto the manipulation chamber in a series of moving consecutive rings, labeled A-G in FIGS. 22A-22D. The images shown in FIGS. 22A-22D were captured using a CCD camera, as discussed in Chiou et al., "Massively parallel manipulation of single cells and microparticles using optical images," Nature, vol 436, July 2005, incorporated by reference herein.

Figure 22A:
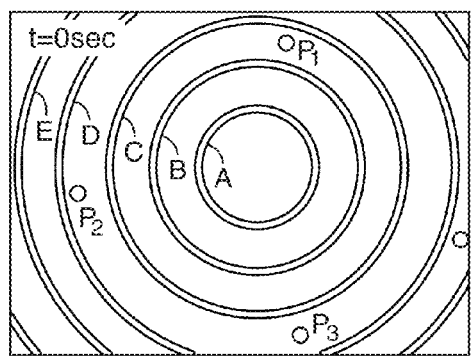
FIGS. 22A-22D show snapshots in time of particle manipulation using an optoelectronic manipulation chamber according to an exemplary embodiment.
Figure 22B:
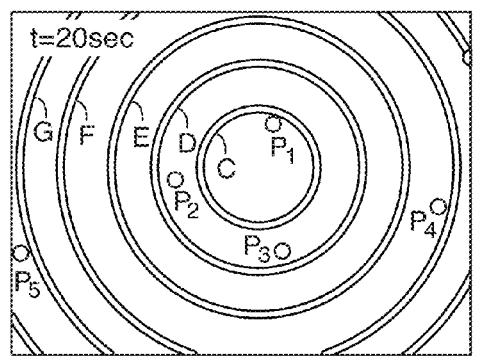
Figure 22C:
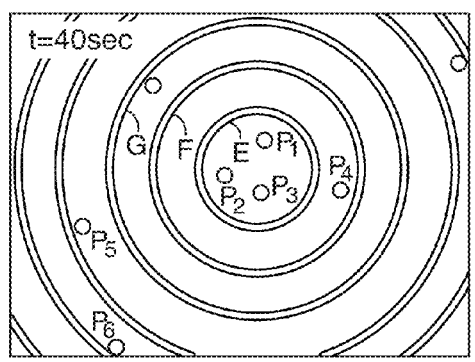
Figure 22D:
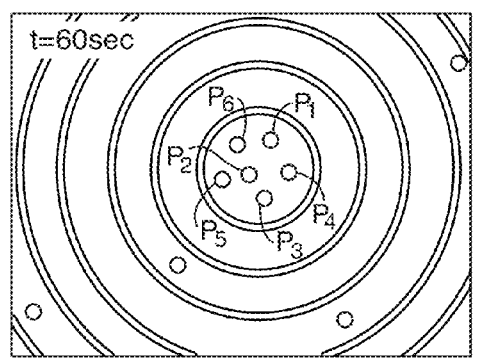

Thus, as shown in FIG. 22A, at the beginning of the optoelectronic manipulation of the beads (e.g., time=0 sec), concentric rings of light A-E are illustrated. As time progresses, for example at 20 seconds into the manipulation, rings A and B have disappeared and ring C has moved to become the innermost light ring, as shown in FIG. 22B. After 40 seconds, as shown in FIG. 22C, light ring E moves to the innermost position with rings A-D having disappeared. At 60 seconds into the manipulation process, as shown in FIG. 22D, all of the original light rings A-E shown in FIG. 22A have disappeared.

The polystyrene beads present in the aqueous medium in the manipulation chamber are labeled $P_n$ in FIGS. 22A-22D. As can be seen by the movement of the various labeled particles $P_n$ in FIGS. 22A-22D, by encircling the particles in continuously decreasing rings, the particles were moved from outer regions of the manipulation chamber so as to be collected within the innermost ring. Thus, the results of FIGS. 22A-22D demonstrate that a manipulation chamber wherein the first substrate is provided with a PEGylated transparent gold electrode, instead of ITO for example, may be used to manipulate particles via optoelectronically induced DEP.

Figure 23:
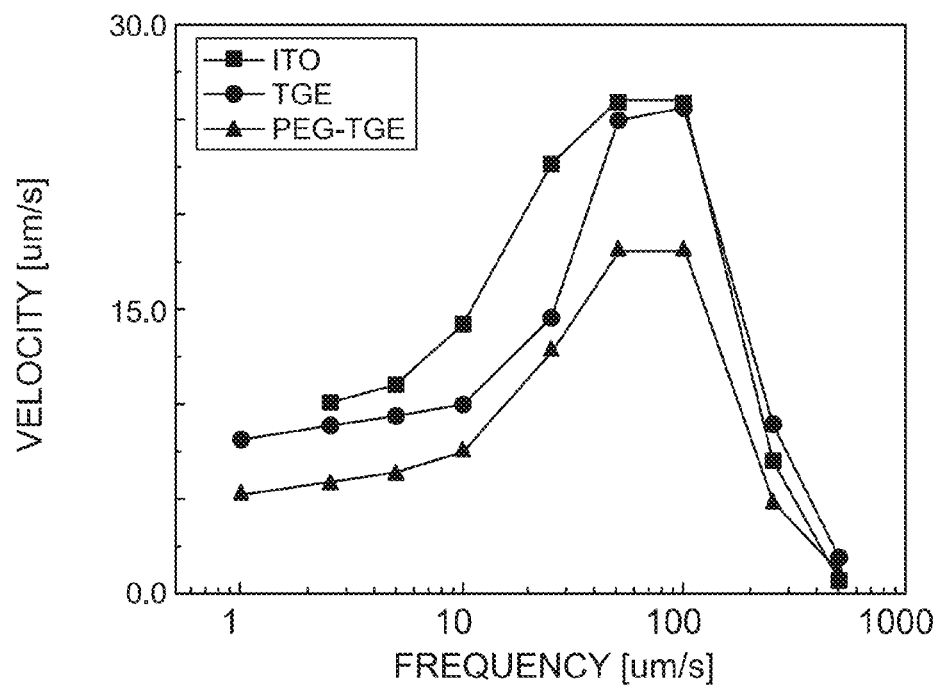
FIG. 23 is a graph showing manipulation speed as a function of applied AC frequency for various exemplary embodiments of optoelectronic manipulation chambers.

FIG. 23 shows a comparison of the manipulation speed of the polystyrene beads in a manipulation chambers using various electrode configurations for the first, upper substrate (e.g., the nonphotoconductor substrate). In particular the results for using an ITO electrode are shown by the squares, the results for using a transparent gold electrode (TGE) are shown by the circles, and the results for using a PEGylated transparent gold electrode (PEG-TGE) are shown by the triangles. The second, bottom substrate (i.e., with the photoconductor thereon) has the configuration described above with reference to the results in FIG. 22.

The results of FIG. 23 show manipulation speed as a function of applied frequency to a manipulation chamber filled with a 10 mS/m KCl solution in deionized water containing polystyrene beads having a diameter of about 20 microns. Velocity was measured by calculating the linear distance in pixels traveled by a bead over a fixed time period. Each data point in FIG. 23 represents an average of six velocity measurements take from two manipulation chambers.

As demonstrated by the results in FIG. 23, the peak manipulation speed corresponding to a manipulation chamber wherein the first substrate electrode was a TGE was about the same as that for a manipulation chamber wherein the first substrate electrode was an ITO electrode. The PEGylated TGE substrate surface resulted in a decrease in manipulation speed.

Figure 24A:
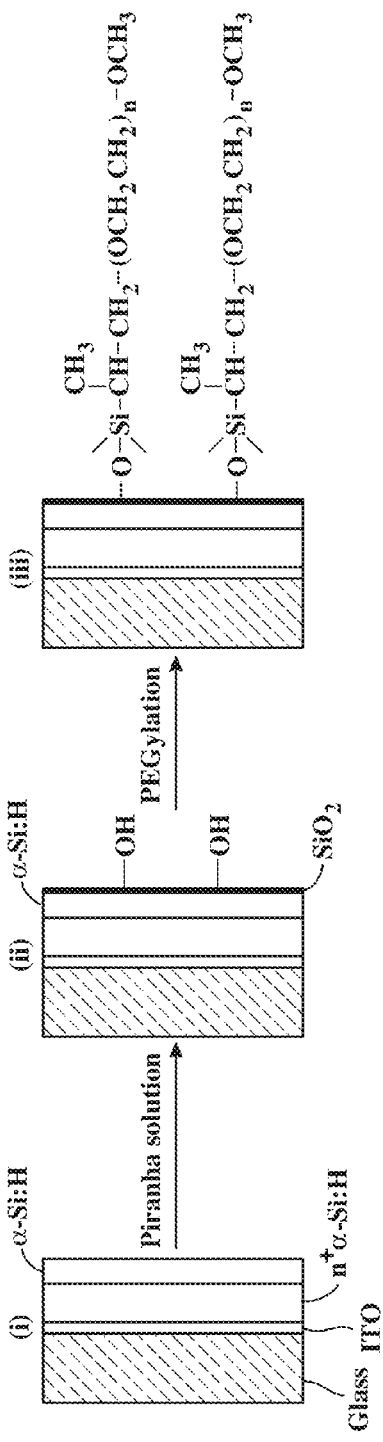
FIGS. 24A and 24B show schematic representations of exemplary steps for fabricating a substrate with a PEGylated SiO$_2$ photoconductive layer.
Figure 24B:
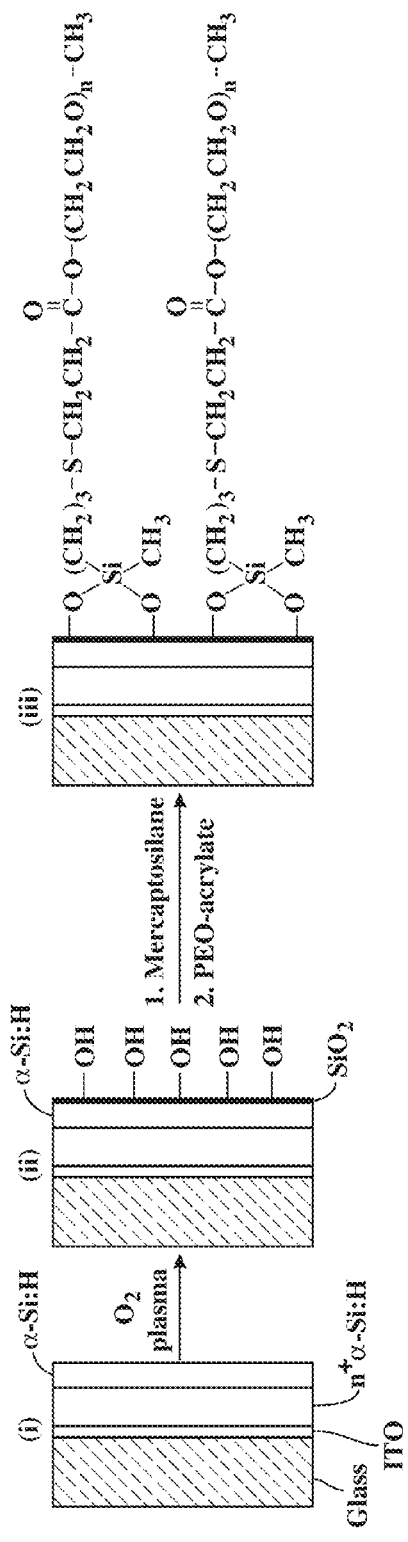

With reference now to FIGS. 24A and 24B, two exemplary approaches for fabricating a PEGylated photoconductive surface, such as layer 1534 shown in FIG. 15, are shown. In FIG. 24A, a glass substrate, e.g., substrate 1530, was provided with an electrode layer such as an ITO electrode layer 1532, which in turn was provided with a photoconductive layer thereon. In an alternative, the electrode layer can be an aluminum or gold electrode layer. Further, the electrode may be transparent or nontransparent.

In the exemplary approach shown in FIG. 24A, the photoconductive layer comprised a $n^+$ α-Si:H (doped amorphous silicon) photoconductor with a α-Si:H (amorphous silicon hydride) protective layer deposited thereon. A Piranha solution was applied to the surface of the substrate of step 24A(i) in FIG. 24A, which resulted in growing a skin (protective) layer of silicon dioxide with silanol hydroxy groups (OH) attached to the surface, as depicted in step 24A(ii). Silicon dioxide was then subjected to a PEGylation process using 2-methoxy(polyethyleneoxy)propyltrimethoxysilane obtained from Gelest, Inc., which yielded the configuration depicted in step 24A(iii). It should be noted that n in the PEG groups in step 24A(iii) can range from 2 to 100, however, in the examples made and tested n ranged from 6 to 9. As n increases, nonspecific adsorption may be reduced.

A second exemplary approach for achieving PEGylation of the photoconductor layer of the second substrate is illustrated in FIG. 24B. In this approach, cleaning and enhancing (e.g., PEGylating) the photoconductive surface may occur in a single step within a vacuum chamber. Thus, the glass substrate with the electrode and photoconductor layers thereon may be substantially the same as described with reference to step 24A(i) above. Within a single vacuum chamber process, the substrate shown in FIG. 24B(i) was subject to an oxygen plasma treatment. The oxygen plasma cleans the surface of the amorphous silicon hydride (α-Si:H) and at the same time grows a skin layer of silicon dioxide on the surface. The resulting skin layer of silicon dioxide was then subjected to a mercaptosilanization with 3-(mercaptopropyl)methyldimethoxysilane (obtained from Gelest, Inc.), as shown in step 24B(ii), implanting surface mercapto groups thereon. The mercapto groups further reacted with poly(ethylene glycol) methyl ether acrylate, PEO acrylate (obtained from Aldrich Chemical), to yield a PEGylated photoconductive layer, as depicted in FIG. 24B(iii). As with FIG. 24A, n in the PEG groups in step 24B(iii) can range from about 2 to 100, and as n increases, nonspecific adsorption may be reduced. In the example made and tested n was about 8.

Based on preliminary tests of the PEGylated photoconductive surface, subjecting the manipulation chamber to a 10V AC bias and a light source of 16 W/mm$^2$, surface adsorption of HeLa cells was less than about 10% using the PEGylation treatment approach of FIG. 24B and was less than about 20% using the PEGylation treatment approach of FIG. 24A, with n about 8 in both approaches. Using a substrate and photoconductive surface as described in, for example, Chiou et al., "Massively parallel manipulation of single cells and microparticles using optical images," Nature, vol 436, July 2005, incorporated by reference herein, the adsorption of HeLa cells under similar conditions was greater than about 80%. Thus, it appears that a PEGylated silicon dioxide photoconductive surface may reduce nonspecific adsorption.

Figure 25:
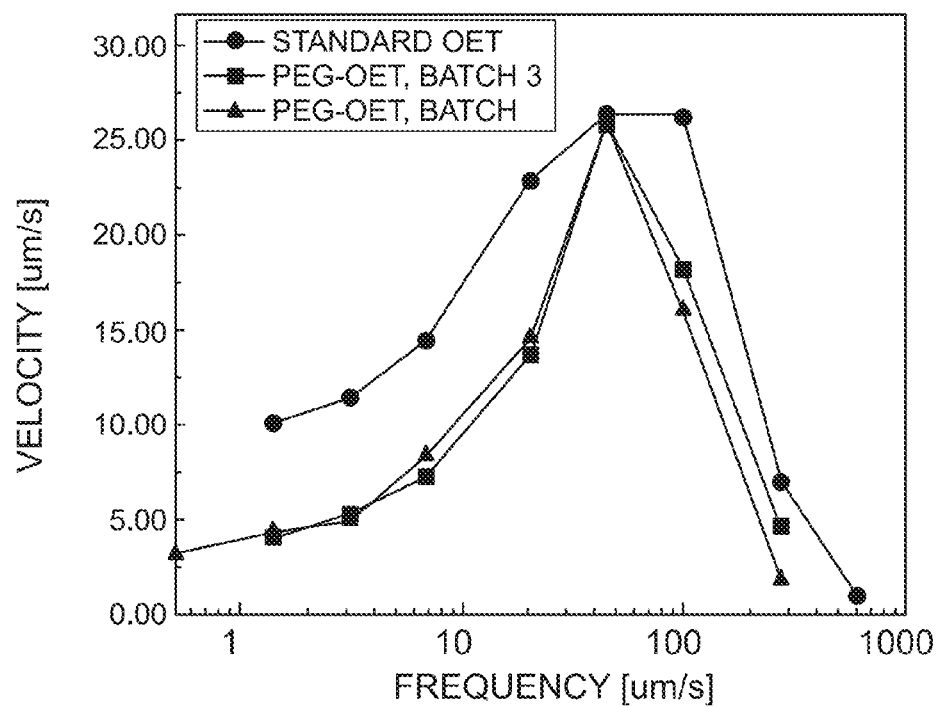
FIG. 25 is a graph showing manipulation speed as a function of applied AC frequency for yet further exemplary optoelectronic manipulation chamber embodiments.

FIG. 25 shows a comparison of the optoelectronic manipulation speed of polystyrene beads in a manipulation chamber comprising a first, upper substrate (e.g., the nonphotoconductor substrate) having a non-PEGylated transparent ITO electrode deposited thereon, such as for example, the nonphotoconductive substrate described in Chiou et al., "Massively parallel manipulation of single cells and microparticles using optical images," Nature, vol 436, July 2005, incorporated by reference herein, and various second, lower, photoconductive substrates. For example, tests measuring manipulation speed were performed using a bottom, photoconductive substrate having a configuration like that described in Chiou et al., "Massively parallel manipulation of single cells and microparticles using optical images," Nature, vol 436, July 2005, incorporated by reference herein (shown by the diamonds in FIG. 25), a PEGylated photoconductive surface like that resulting from the process of FIG. 24A (shown by squares in FIG. 25), and a PEGylated photoconductive surface like that resulting from the process of FIG. 24B (shown by triangles in FIG. 25). The other experiment conditions described with reference to FIG. 23 were also used for the results shown in FIG. 25. As illustrated in the results of FIG. 25, the peak optoelectronic manipulation speed for the three different photoconductive substrate configurations is approximately the same.

It is envisioned that in various exemplary embodiments, the optoelectronic techniques and devices described herein could be used in combination and as part of an accessory to a portable medical device or to a microscope in order to visualize, observe, and/or collect data about the manipulation of the various particles within the manipulation chamber. Moreover, it is envisioned that in various exemplary embodiments, the optoelectronic manipulation chambers in accordance with the invention could be used in combination with existing mechanical manipulation and analysis mechanisms, such as laser pressure catapulting, laser microdissection, laser microinjection, electroporation, microcapillaries, microdissection, microinjection, micromanipulation, piezoelectric microdissection, patch clamp electrodes, and/or drug interaction for cell response measurement. When using optoelectronic manipulation chambers in conjunction with other manipulation tools, it may be desirable to provide the manipulation chambers with ports and/or other openings to permit access to the interior of the chamber by such manipulation tools.

Further, it is envisioned that real time visualization and/or data collection and analysis of particle sorting and/or other particle manipulation using an optoelectronic manipulation chamber according to aspects of the invention may occur.

Figure 33:
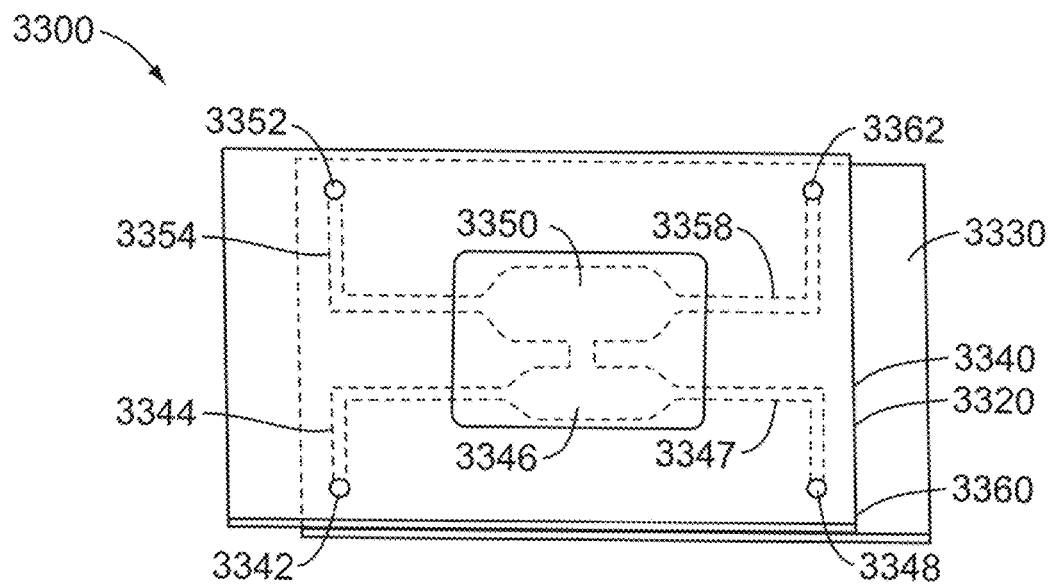
FIG. 33 is a perspective view of an exemplary embodiment of an optoelectronic manipulation chamber integrated with a cartridge assembly.

FIGS. 33-34 show exemplary embodiments of how optoelectronic sorting devices, including, for example, those depicted in FIGS. 8-11, may be integrated as part of a microcard, chip assembly, and/or other disposable cartridge assembly.

Figure 33A:
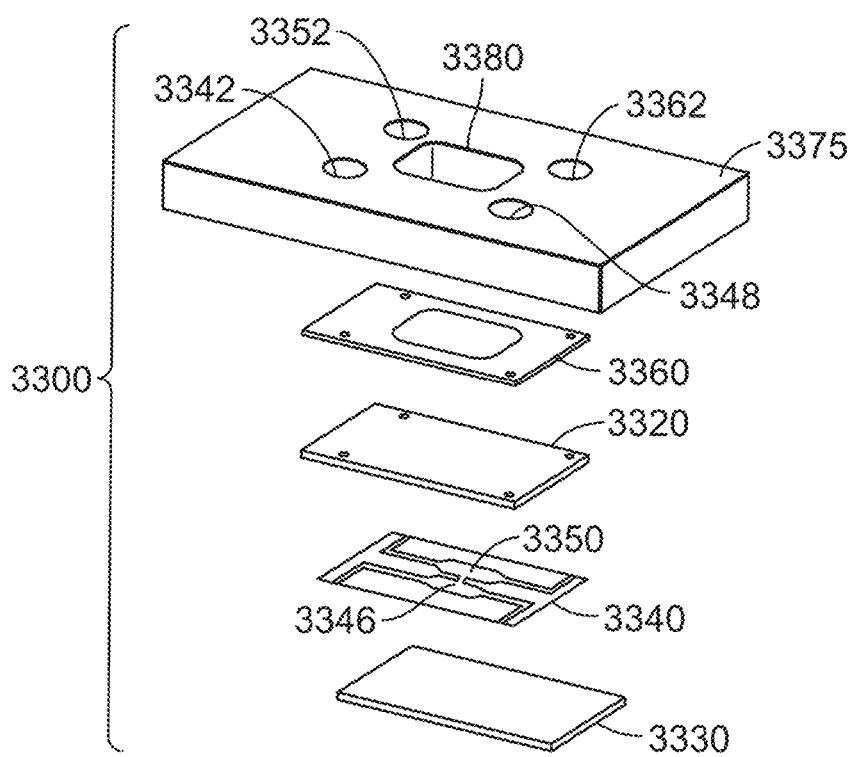
FIGS. 33A and 33B are isometric top and bottom views, respectively, of the exemplary embodiment of FIG. 33.
Figure 33B:
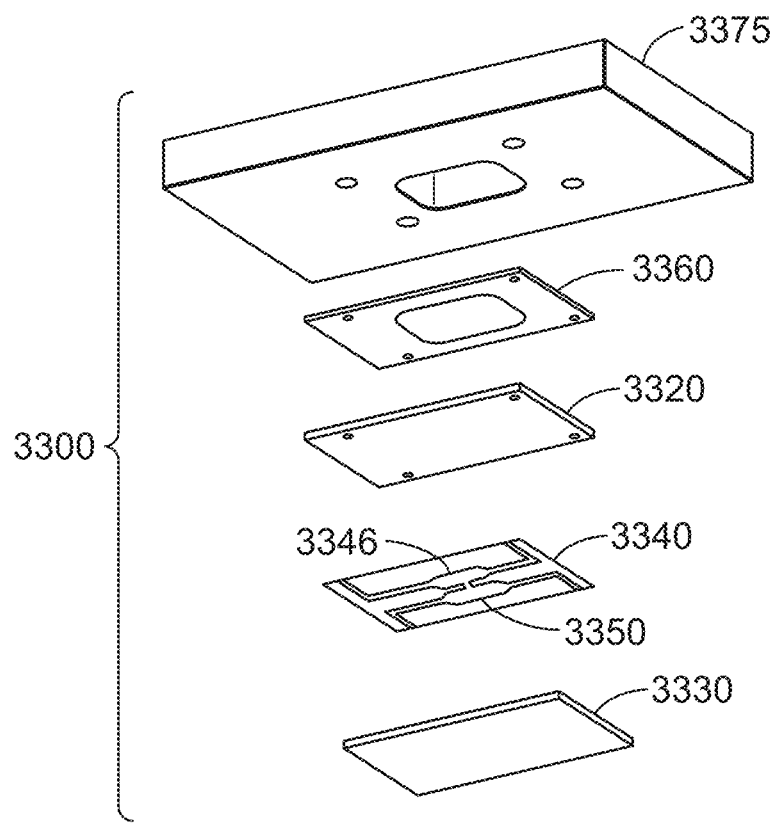

FIGS. 33, 33A, and 33B illustrate an exemplary embodiment of such a cartridge assembly 3300. FIG. 33 represents a top view of the assembly 3300, while FIGS. 33A and 33B represent isometric views of the assembly 3300 taken from the top and bottom, respectively. The cartridge assembly 3300 may include a bottom substrate 3330 and a top substrate 3320 with a spacer 3340 sandwiched therebetween. The bottom substrate 3330 may include the various layers (not shown) described with reference to substrate 30 of FIG. 1, including an amorphous silicon photoconductive layer consistent with the teachings herein. The top substrate 3320 may include the various layers (not shown) described with reference to substrate 20 of FIG. 1, including a transparent electrode.

The spacer 3340 may be provided with openings through the thickness of the spacer 3340 so as to define a series of chambers and channels, as shown in FIGS. 33, 33A, and 33B. The series of chambers and channels may have similar configurations as those in FIGS. 8-11 or other configurations, as would be understood by those with ordinary skill in the art. The series of chambers and channels defined by the openings in the spacer 3340 thus may serve as optoelectronic scanning chambers disposed between the top and bottom substrates 3320 and 3330, as is described with reference to various embodiments herein. Thus, when secured together, elements 3320, 3340, and 3330 define an optoelectronic scanning component configured to identify, sort, and/or collect particles via optoelectronic scanning.

By way of example, in the embodiment shown in FIGS. 33, 33A, and 33B, the spacer 3340 defines a first chamber 3350 in flow communication with an inlet channel and an outlet channel and a second chamber 3346 in flow communication with another inlet channel and outlet channel. The first and second chambers 3350 and 3346 also are in flow communication with each other via a small channel. The chamber 3350 may be configured as a sorting/identification chamber, for example, similar to chambers 110, 310, 410, and 510 described with reference to FIGS. 8-11. The chamber 3346 may be configured as a target collection chamber, for example, similar to the chambers 146, 356, 446, and 546 described with reference to FIGS. 8-11. The channel 3354 may be configured to introduce a sample containing a plurality of differing types of particles (e.g., a biological sample containing a plurality of differing cell types) to the chamber 3350 and the channel 3358 may be configured to lead nontarget particles from the chamber 3350 after optoelectronic sorting and/or identification has occurred in the chamber 3350, in a manner similar to that described with reference to FIGS. 8-11, for example. The channel 3344 may be configured to provide a buffer solution to the chamber 3346 and the channel 3347 may be configured to lead the buffer solution and collected particles from the chamber 3346 for further processing.

The elements 3320, 3340, and 3330 may be secured via a suitable adhesive layer 3360, such as, for example, a PSA layer, to a base 3375 that has various ports (e.g., cups) 3352, 3362, 3342, and 3348 in flow communication with channels 3354, 3358, 3344, and 3347, respectively, for loading and unloading sample, buffer, and collected target and/or nontarget particles. The base 3375 also may define a relatively large opening configured to provide optical access to the optoelectronic scanning chambers 3350 and 3346. In various exemplary embodiments, the base 3375 may be made of a plastic, such as, for example, cyclic olefin polymer (COP). The adhesive layer 3360 also may be provided with an optical access opening in alignment with the opening 3380, and the adhesive layer 3360 and substrate 3320 also may define a plurality of openings respectively aligned with and in flow communication with the openings 3352, 3362, 3342, and 3348.

Figure 34A:
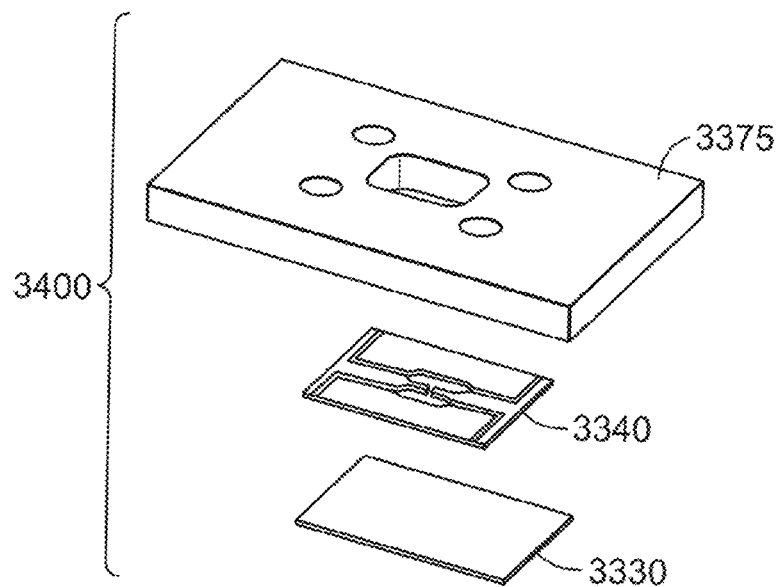
FIGS. 34A and 34B are isometric top and bottom views, respectively, of another exemplary embodiment of an optoelectronic manipulation chamber integrated with a cartridge assembly.
Figure 34B:
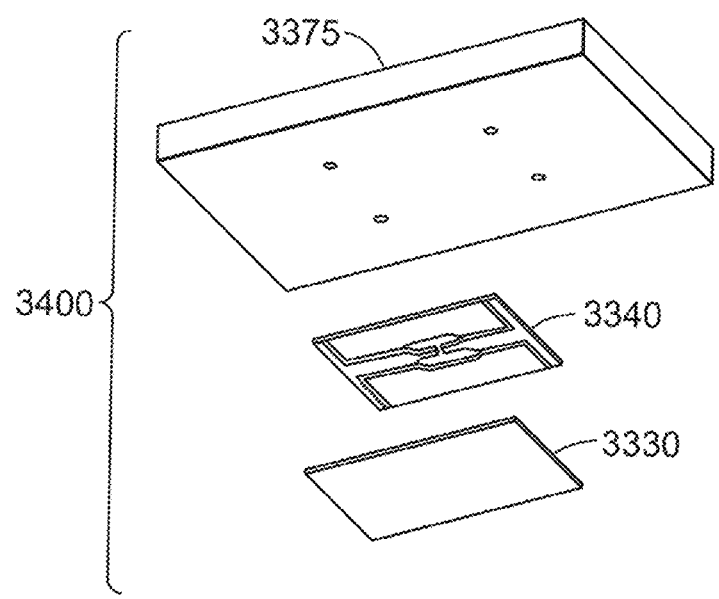

In an alternative exemplary embodiment, as depicted in the top and bottom isometric views of FIGS. 34A and 34B, a cartridge assembly 3400 may include a transparent electrode layer directly deposited on the surface of the base 3375 that faces the spacer 3340 rather than being deposited on a separate substrate. By way of example and not limitation, the transparent electrode layer may be coated via e-beam evaporation. In an exemplary embodiment, the electrode layer may be a gold electrode layer of about 7-8 nanometers in thickness. The transparent electrode may be patterned on the base 3375 using a shadow mask, Kapton tape, or other suitable patterning mechanism known to those skilled in the art. Due to the deposition of the transparent electrode directly on the base 3375, the exemplary embodiment of FIGS. 34A and 34B obviates the need for the substrate 3320 and adhesive layer 3360 of the embodiment of FIGS. 33, 33A, and 33B.

Figure 35A:
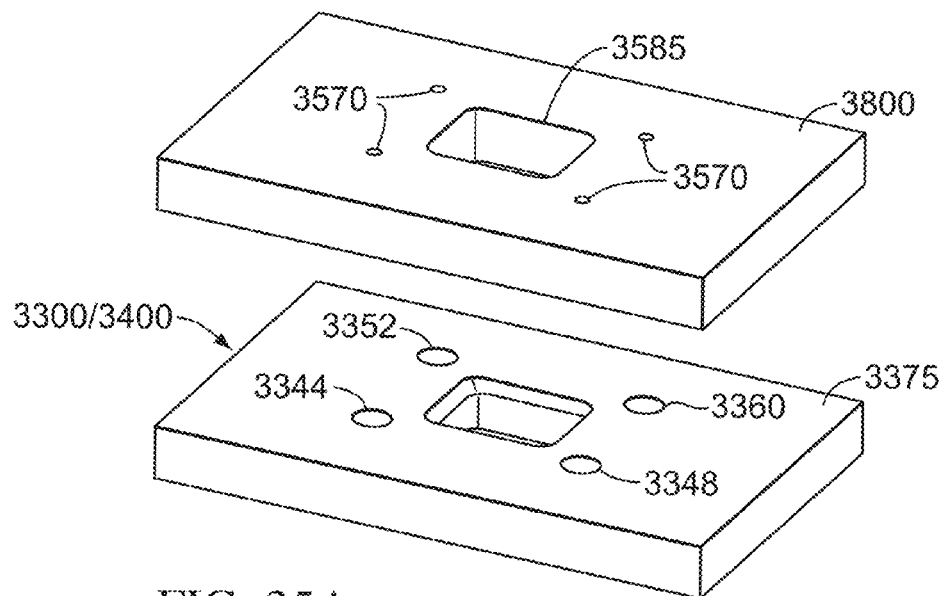
FIGS. 35A and 35B are perspective top and bottom views, respectively, of an exemplary embodiment of an interface mechanism and a cartridge assembly of FIGS. 33-34.
Figure 35B:
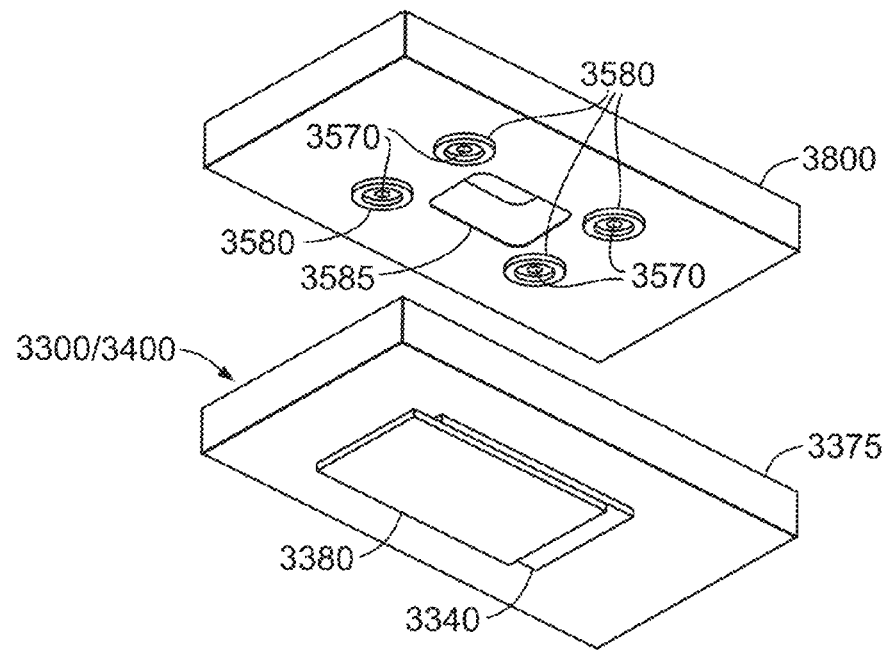

FIGS. 35A and 35B illustrate an exemplary embodiment of an interface mechanism configured to provide an interface between the assemblies 3300 and 3400 of FIGS. 33 and 34, and/or other cartridge assemblies in accordance with the teachings herein, with fluidic instrumentation (such as, for example, valves, pumps, etc.) in order to provide fluidic pumping of buffer, sample, etc. through the assemblies. FIG. 35A is perspective top view of a cartridge assembly 3300/3400 and an interface mechanisms 3500 and FIG. 35B is a perspective bottom view of the cartridge assembly 3300/3400 and interface mechanism 3500. As the various parts of the cartridge assembly 3300/3400 are discussed in detail above, they are not discussed in detail with reference to FIGS. 35A and 35B.

In various exemplary embodiments, an interface mechanism 3500 may be in the form of a card-like device having approximately the same dimensions as the cartridge assembly base 3375. The interface mechanism 3500 may include a plurality of ports 3570 configured to align with and provide fluid communication to the ports 3344, 3352, 3348, and 3362 provided in the cartridge base 3375. According to various exemplary embodiments, the ports 3570 may be ¼ 28 or barb. As depicted in FIG. 35B, a plurality of sealing mechanisms 3580, such as, for example, O-rings, may be secured to the interface mechanism 3500 so as to surround each of the ports 3570 on a surface of the interface mechanism 3500 facing the cartridge base 3375. The sealing mechanisms 3580 may be configured to provide a seal during loading and unloading of the cartridge assembly 3300/3400 with fluid while the cartridge assembly 3300/3400 is clamped to the interface mechanism 3500. The interface mechanism 3500 also may define an opening 3585 configured to align with the opening 3380 in the cartridge assembly 3300/3400 to provide optical access to the chambers 3350 and 3346. Air pressure and/or vacuum may be supplied through the ports 3570 to achieve fluidic pumping. By way of example only, positive pressure pumping may be used with an air source and a pressure regulator. The pressure regulator may be directly connected to one or more ports 3570 and may be electronically controlled.

Although not shown in the figures, in an exemplary embodiment, the interface mechanism 3500 may be an element that is part of the fluidic instrumentation and loading/unloading of the cartridge assembly 3300/3400 may occur as described below. Initially, the cartridge assembly 3300/3400 may be primed with a buffer solution by introducing the buffer solution through port 3344 in the base 3375 so as to fill all of the various chambers and channels in the cartridge assembly with the buffer solution. According to various exemplary embodiments, the buffer may be introduced into the port 3344 via a manual syringe, although other means of introducing the buffer into the port 3344 also may be utilized as would be appreciated by those having skill in the art. After the cartridge assembly 3300/3400 is primed with buffer, a sample containing a plurality of particles of differing types (e.g., a biological sample containing a plurality of cells of differing types) may be introduced into the port 3352 in the base 3375. The port 3352 may serve as a cup to hold the sample until pressure and/or vacuum is used to move the sample through the channels and chambers of the spacer 3340 of the cartridge assembly 3300/3400. By way of example, the sample may be introduced into the port 3352 via a pipette.

After introducing sample into the port 3352, the cartridge assembly 3300/3400 may be clamped to the interface mechanism 3500 and the sample may be pumped into the optoelectronic sorting/identification chamber 3350 via a positive pressure or vacuum applied to the port 3352. Optoelectronic scanning may then be performed by scanning a light across the optical access openings and/or windows 3380, 3360, and 3585 to achieve desired identification, sorting, and/or collecting of the particles in the sample. Once particles of interest (e.g., target cells) have been collected, they may be brought into alignment with the port 3348, in a manner consistent with the teachings herein (e.g., with reference to FIGS. 8-11 and 29) and the cartridge assembly 3300/3400 may be released from the interface mechanism 3500. The collected target cells may be removed from the cartridge assembly 3300/3400 from the port 3348, for example, via pipetting.

The exemplary embodiments of FIGS. 33-35 may provide several features. For example, the cartridge assemblies are relatively simple in design and configuration and allow for relatively simple operations for loading, unloading, and optoelectronic scanning. Further, because loading/unloading ports (e.g., cups) are located in relatively close proximity to the sorting chamber, cell loss due to long microfluidic channels may be minimized, thereby achieving high yield and recovery of target cells. Moreover, contamination of the fluidic instrumentation may be minimized due to the use of pressure/vacuum forces for loading and unloading the cartridge assembly.

The various devices and methods in accordance with exemplary aspects of the invention provide advantages over existing techniques when used for identification, sorting, characterization, collection, and/or other manipulation of small particles, such as, for example, cells, stem cells, DNA, and other biological particles. For example, use of at least some of the optoelectronic techniques described herein permits the manipulation of cells, stem cells, DNA, and other biological particles without the use of dyes, high intensity lasers, and/or other mechanisms that may stress and/or damage the particles being manipulated. Further, devices in accordance with various exemplary aspects of the invention are relatively inexpensive to fabricate and may achieve relatively high sorting throughput. The devices according to various exemplary embodiments may not require formation of patterned electrodes, microchannels, and/or other relatively complex structures, and thereby may promote added flexibility in the capability to modulate electric fields in a variety of dimensions and strengths. The techniques and devices described herein in accordance with aspects of the invention also may be less susceptible to clogging and reduce nonspecific adsorption of biomolecules. It is envisioned that groups (e.g., bunches) of particles also may be collected and routed together.

It is envisioned that the use of DEP, including optoelectronically-induced DEP using the embodiments in accordance with exemplary aspects of the invention may be applied to a variety of applications related to cell biology. For example, surface-active agents, including ligands, antibodies, glycoconjugates, and other agents may be used to differentiate tumor (e.g., cancer) cells from other cells by altering the dielectrophoretic properties of such cells and then using DEP, including optoelectronically-induced DEP, to separate and/or identify the tumor cells from other cells. Relying on dielectrophoretic characteristics as the mechanism to separate and/or distinguish cell types may provide enhanced differentiation, faster sorting throughput, and other advantages when compared to conventional techniques, such as, for example, protocols that involve centrifugation, suspension, and jelled clots.

Moreover, using DEP and dielectrophoretic characteristics as a basis for cell differentiation permits physiology of cells to be utilized as the parameter for distinguishing cells, rather than surface or cell expression that is used in conventional techniques relying on markers, for example. Reliance on cell physiology and DEP for cell differentiation may provide enhanced differentiation and may provide an improved methodology for cell differentiation, isolation, and study. Thus, the use of DEP, including optoelectronically-induced DEP, for example, may provide various advantages over conventional technologies in the areas of stem cell, cancer cell, and tumor cell differentiation, isolation, and research. A further explanation of how DEP may be applied in stem cell and cancer cell biology applications is provided below.

Some conventional methods of stem cell (SC) identification utilize specific monoclonal antibody markers. However, no single marker is adequate to identify subclasses of SCs. This reflects the fact that changes in proliferative/differentiative state is not quantal in nature, but rather a continuum of phenotypes. For example, CD34 is a cell surface receptor widely used as a "specific" marker of hematopoetic stem cells, but a multi-marker phenotype (CD34$^+$, c-Kit$^+$, Thy-1$^{lo}$, Lin$^-$) is generally utilized and even within this set of "stem cells" are sub-populations of cells with different differentiation potential. Further, most organ-restricted stem cells (i.e. adult stem cells) lack unique and specific markers so that even using "good" markers and sorting by FACS, recovered cells are heterogeneous.

Hence, conventional approaches to stem cell research may be limited by the need for these markers and the inherent inadequacies of this approach for identifying and isolating stem cells. DEP and optoelectronic scanning in accordance with the teachings herein may provide an alternative approach to identifying and isolating stem cells.

A "side population" of cells has been described in bone marrow analyzed by FACS analysis of Hoechst-dye stained cells. Subsequent sorting and characterization revealed this subpopulation of cells to be rich in stem cells that were, however, heterogeneous in CD34 expression. Failure to take up Hoechst-dye is characteristic of cells expressing MDR-related proteins and an MDR phenotype. This so-called side population of cells has been confirmed many times as comprising stem cells and this assay is commonly used to isolate stem cells; in some settings, "side population" is taken to mean "stem cells." In addition to showing that hematopoetic stem cells have an MDR phenotype, it has been shown that the MDR phenotype is independent of CD34 expression, meaning that "CD34+" and "stem cell" are not synonymous.

Multidrug resistance (MDR) is a cellular phenomenon in which cells are resistant to the cytotoxic effects of a variety of small molecule antineoplastic agents. Overall the mechanisms of drug resistance are varied but MDR represents a major mechanism that has been implicated in clinical resistance to cytotoxic drug action. The MDR phenotype is conferred by expression of one or more of the 49 members of the ABC transporter protein family that function in part to pump out drugs by an ATP-driven process before they can reach cellular targets and kill the cell. The presumed "normal" function of ABC transporters is in part to rid the cell of toxic xenobiotics, but regulation of intracellular pH is also a likely role. Cells can be inherently drug resistant via MDR proteins or the phenotype may be acquired by exposure to cytotoxic agents. MDR is problematic for small molecule chemotherapeutic agents, and some protein-based drugs (immunotoxins), and is estimated to be responsible for as much as 50% of chemotherapy failures.

The reagent, Hoechst 33242, bisibenzimide, is a fluorescent dye that binds with very high specificity to DNA. It is unique among DNA-binding dyes in penetrating live cells and binding stoichiometrically to cellular DNA (and not RNA). Being the only dye that does so, it has been very widely utilized in many contexts for cell cycle analysis by FACS. Hoechst has also been shown to be a substrate for some ABC transporters and whereas viable non-MDR cells exposed to Hoechst will take up the dye and stain brightly, MDR+ cells stain very dimly reflecting the activity of the ABC transporter(s) in excluding the compound from cells. The "side population" of cells described above is "side" because the cells do not take up Hoechst dye. Exclusion of Hoechst (and other dyes) represents a common functional assay for MDR in mammalian cells and routinely used in conventional techniques for stem cell identification.

It also has been demonstrated that MDR-human leukemia cells differ 2-fold from their normal drug-sensitive parental cells in cytoplasmic conductivity and hence can be discriminated from each other solely on the basis of DEP differences. While these data represent the only report of a relationship between MDR and DEP, it is known that MDR proteins act as proton pumps regulating intra-organellar pH within cells and can impact overall intracellular pH. The DEP differences may reflect differences in intracellular ion content or concentration (i.e. cytoplasmic conductivity), rather than MDR activity at the plasma membrane level because standard MDR-reversing drugs did not have an impact on the DEP of the cells while altering dye uptake.

Dielectrophoresis has been reported to distinguish CD34+ stem cells in peripheral blood and bone marrow stem cell harvests. Significant dielectrophoretic differences between CD34+ cells and all other leukocytes have been measured using dielectrophoretic crossover frequency. These differences have been explained in terms of cell size (stem cells are small) and cell surface topology (stem cells have relatively "smooth" surfaces), both factors known to influence the dielectrophoretic properties of viable cells. To date, however, it does not appear that a relationship between stem cells, the MDR phenotype and dielectrophoresis has been reported.

The inventors thus believe that the MDR phenotype of hematopoetic (and potentially other) stem cells, alone or in combination with cell size and morphology, represents a key element of the stem cell phenotype that is uniquely suited to cell characterization and isolation by dielectrophoresis. Therefore, the inventors believe that stem cells may be studied using dielectrophoretic potential as the primary means of cell identification and isolation and cell surface markers as secondary phenotypes.

"Markerless" selection of stem cells has been demonstrated. For example, size-sieving of bone marrow mononuclear cells has been utilized to isolate mesenchymal stem cells, which lack discrete markers altogether, and the differentiation potential of size-sieved cells differed. Counterflow centrifugal elutriation which separates cells on the basis of size and density has also been used to isolate stem cells from peripheral blood. Thus, in these studies, known stem cell markers were not necessary to separate subsets of stem cells giving rise to different tissue-type cells.

Putative cancer stem cells have recently been reported to occur in breast, brain and hematopoetic tumors. Increasingly, these cells are becoming the focus of both oncology and pharma because they may represent a new and significant class of cellular targets for cancer therapy. The hypothesis is that these cells represent the source of rapidly proliferating tumor cells and persist in the tumor after treatment, becoming responsible for tumor re-growth the unfortunate ultimate outcome for most treatments.

The convergence of stem cell research and oncology is providing something of a "paradigm" change in thinking about cancer and a significant impetus for research into the nature of these cells and means of specifically targeting them for therapy. The emergence of drug resistance following therapy historically has been explained as either the acquisition of a new phenotype by the treated cells (which can be readily accomplished in-vitro) or selection for pre-existing resistant cells. To the extent that clinical drug resistance is explained by an MDR phenotype, tumor stem cells display an MDR phenotype, drug resistance (MDR), cancer stem cells and residual disease may represent semantic distinctions rather than biological ones. By the same argument that DEP may be a unique parameter with which to characterize stem cells in a developmental context, it may also be used to address questions cancer stem cells and drug resistance in tumors.

As has been discussed above, optoelectronic dielectrophoretic physiometry can provide a unique technology for cell identification, characterization, manipulation and sorting based on the electrical consequences of differences in cellular structure and physiology. This technology exploits the fact that cellular structure and physiologic functions and changes therein impact the key electrical features of cells including but not limited to internal and external membrane conductivity, capacitance and permittivity; cytoplasmic conductivity, capacitance and permittivity, cell size and nucleocytoplasmic ratio and surface complexity that collectively determine the polarizability (dielectric potential) of cells in a high frequency AC electric fields and their response to external AC/DC fields generated by optoelectronic means in specified suspending media.

Applications of optoelectronic DEP include but are not limited to identification, characterization, manipulation and sorting of stem cell, cancer cells, cancer stem cells, blood cells and cells of any organ (e.g. pancreas, skeletal muscle, lung, liver) that can be suspended in medium ex-vivo. The contexts of cell analysis include but are not limited to clinical and non-clinical research, diagnostics, theragnostics, drug discovery and development, and environmental monitoring. Various applications and embodiments are discussed in more detail below.

Optoelectronic dielectrophoretic physiometery represents a significant advance over prior dielectrophoretic systems in that the DC component of the cell manipulation system is generated by optically activated electronic materials rather than specifically-arranged solid electrodes. This approach may provide increased flexibility in the manner in which cells are identified, isolated, manipulated and sorted and also may provide many options for realtime feedback regulation of the manipulation processes, as well as generation of optical signals from cells that can provide structural, functional and molecular information pertaining to their state. Additional forces, e.g. fluid flow, can be used simultaneously adding flexibility to the system. Additionally, fabrication and operational costs can be very low relative to conventional technologies.

Exemplary applications of this technology in the fields of stem cells, cancer and immunology are discussed below providing a common basis for the utility of this technology in diverse fields.

The identification, characterization and isolation of immune cells and cancer cells has historically been based on expression of cell surface antigens that are tagged with fluorochrome-labeled monoclonal antibodies specific to these antigens. Many cocktails of antibodies are in common use, but stem cell definition based on surface markers is incomplete. A gene-expression pattern defining "sternness" has not, however, emerged from expression profiling studies and therefore, the ultimate only reliable criteria of "sternness" of stem cells remains the proliferative/differentiative potential of candidate cells. Somewhat analogously, specific gene expression profiles of tumors have yielded a wealth of genic information but in the end more data than information has been generated and cell morphology is typically utilized as the ultimate criterion of malignancy.

Recently, the physiology of cancer cells has re-emerged as a key area of cancer research. In particular, the unique energy metabolism and cell-growth environment of tumor cells are receiving attention not as epiphenomena of altered gene expression but perhaps as causally related to oncogenesis. The capacity of "unlimited" proliferation is a key similarity between cancer and stem cells, and both direct and circumstantial evidence suggests that stem cells share gene expression patterns and may be metabolically similar to cancer cells. There is growing evidence that cancer stem cells and stem cells per se are highly overlapping sets.

Among the features shared by stem cells and cancer cells is the expression of so-called MDR genes that reside in both the plasma and intracellular membranes where they act as transporters of a variety of small organic molecules, particularly organic ions. In the case of tissue stem cells, ABCG2 (BCRP, breast cancer resistance protein) transporter function is defining of very primitive precursor cells and for cancer, transporter function is central to drug resistance and also defining of stem cells at least in some contexts. The function of these transporters is central to current phenotypic definition of stem cells and to the MDR phenotype of cancer cells.

A so-called "side population" of CD34$^+$ hematopoetic stem cells has become an important functional marker of hematopoetic stem cells. The "sideness" of this population of cells reflects the failure of cells to stain with either of two flourescent organic dye molecules, bisbenzimide (Hoechst) or Rhodamine 123, because they express one or more MDR proteins and therefore pump these molecules out of the cell. Relative to non-stem cells, these cells are dim when stained with specific fluorescent dyes. Side populations have subsequently been identified in cell populations derived from breast cancer, lung cancer and neural cancer as well as some normal tissues providing in part, the rationale for the idea of cancer and non-hematopoetic tissue stem cells.

The hematopoetic stem cell phenotype described as side population has been demonstrated to be due to one particular transporter, ABCG2 (also called BCRP, breast cancer resistance protein), that is highly expressed on very primitive stem cells and many cancer cells. In the hematopoetic system, ABCG2 is a marker of the most primitive stem cells which may or may not express CD34 or other surface markers.

MDR proteins represent a large family of membrane-spanning proteins that actively extrude or efflux a wide variety of organic molecules in an ATPase-driven manner. As a class they are referred to as ABC transporters (ATP binding site cassette) and possess highly conserved ATP-binding and transmembrane domains. The family is diverse as are the substrates. While these proteins act to exclude toxic xenobiotics being responsible for cancer cell resistance to cytotoxic agents, they also are involved in transport of a wide variety of bulky lipophilic organic anions and cations. The extent to which ABC proteins show substrate specificity is somewhat unclear as those responsible for some drug resistance phenotypes appear to be promiscuous with respect to substrates.

While there remains some confusion as to the specific ABC transporter involved (BCRP and/or MRP-1), the side population phenotype in hematopoetic stem cells is by definition due to ABC transporter expression. Side populations have been observed in a variety of tumor (breast, neural, ALL, AML) and normal tissues (breast, lung, prostate, eye, skin) and in some cases it has been shown that the phenotype is the result of ABC transporter activity. Thus it appears ABC transporter expression and activity represents a key molecular marker for stem cells in general and cancer cells.

While ABC transporters do not transport inorganic ions, they are known to transport organic ions. ABC transporter function and the drug resistance phenotype have been studied by dielectrophoresis in cancer cell lines. One such study demonstrated that cells with an MDR phenotype can be distinguished from non-MDR cells by DEP. Because this effect was not abolished by blocking ABC activity with an MDR-reversing drug (verapamil), it was suggested that ABC transporter function and DEP differences were related to differences in cytoplasmic conductivity rather than drug pumping activity per se.

While it is clear that the resistance of cancer cells and stem cells to cytotoxic agents reflects at least in part the activity of ABCG2, the "normal" role of the protein is not entirely clear. However, some studies suggest that ABCG2 may be involved in maintaining stem cell viability and proliferative potential under hypoxic conditions which are known to occur in the developing embryo of mammals, embryoid bodies in cultured stem cells. Relative to arterial blood, bone marrow is known to have a lower $pO_2$ and hematopoetic stem cells in normal bone marrow are localized in a relatively hypoxic environment. It is known that hypoxia inhibits stem cell differentiation and sustains stem cell viability and proliferation and that down-modulation of ABCG2 expression is an early and rapid event when stem cells differentiate. Taken together, it appears that ABCG2 is involved in stem cell maintenance under hypoxic conditions that would damage/kill normal non-stem cells but are necessary for stem cell survival and proliferation.

Tissue hypoxia is a prominent feature of solid tumors. It is believed that this is due to the rapid growth of tumor cells which outstrips the rate of angiogenesis. Stimulation of ABC gene expression has not been shown to occur in hypoxic cancer cells. The MDR phenotype and hypoxia may characterize solid tumors and contribute to drug resistance.

As described below, tumor cells utilize glycolysis for energy production under both hypoxic and aerobic conditions and in fact glycolysis is a hallmark of cancer cells. Lactate is the end product of glycolysis. Both normal and tumor stem cells are inhibited from differentiating by hypoxia and it is likely that the glycolytic pathway is also active in them. Tumor cells are characterized, not unlike stem cells, by their capacity for "unlimited" proliferation. Central to the aspect of tumor cell phenotype is the Warburg effect, a shift in energy metabolism from aerobic respiration to anaerobic glycolysis and consequent alkalinization of tumor cell cytoplasm and acidification of the tumor mass itself (for solid tumors). Glycolytic energy metabolism while generally regarded as an adaptation to hypoxia proceeds in the presence of normoxic conditions in cancer cells and the Warburg effect as applied to aerobic glycolysis defines the cancer cell metabolic phenotype.

It should be understood that in various exemplary embodiments, the techniques and devices according to exemplary aspects of the invention may permit control over the generated DEP force and consequent particle manipulation. For example, it is envisioned that the Clausius-Mosotti factor for a particle may be changed, for example, to being positive or negative, by altering the medium in which the particle is suspended and/or by altering the particle itself, such as, for example, by altering the charge, size, and/or otherwise modifying the surface of the particle so as to modify a dielectrophoretic characteristic of the particle. Various ways to alter the Clausius-Mosotti value, the DEP force, and/or other forces acting on particles during optoelectronic manipulation have been described herein, and one having ordinary skill in the art would understand other ways in which to alter the Clausius-Mosotti value and/or forces acting on the particles by altering the various properties, etc. so as to alter the variables in the equations defining those values.

By way of example, and in addition to those already discussed herein, the medium characteristics may be altered so as to adjust the complex permittivity of the medium, $\in_m^*$, and thus the Clausius-Mosotti value. It may be desirable to adjust $\in_m^*$ while maintaining cell compatibility. Arnold, "Positioning and Levitation Media for the Separation of Biological Cells," IEEE Transactions on Industry App., vol. 37(5), pp. 1468-1475 (2001) describes various media used for dielectrophoresis with a focus on those suitable for negative dielectrophoresis in order to avoid cell contact with electrodes to minimize sticking and damage due to high electric field concentration proximate the electrode. Media optimized for negative DEP may have higher polarizability than the particles (e.g., cells) contained in the medium. With respect to polarizability, changes in conductivity tend to dominate at low or medium applied frequencies, while permittivity dominates at higher frequencies.

Water is relatively highly polar and most solutes in water tend to decrease the permittivity, including, for example, sugars added to water to promote osmotic stability. Classes of solutes that may increase permittivity of aqueous media include, for example, the following:

1) Neutral molecules with relatively large dipole moments (e.g., urea, formamides, organic carbonates). This class may not be compatible with cells.

2) Small zwitterions (dipolar ions), such as, for example, amino acids. Zwitterionic buffers may be used at pH about 2 units below pKa to help ensure complete protonation. At higher pH, charged versions of these molecules may contribute to increases in conductivity with a decreased contribution to permittivity. By way of example, $\in$-aminocaproic acid may increase permittivity of a medium.

3) Large zwitterions, such as, for example, polypeptides and proteins. This class may be cost prohibitive.

4) Suspensions of charged particles. This class generally disperses in AC, and contributes to high conductivity.

Quantitatively, the permittivity of the medium may be calculated by the following:

$$\in_m = \in_w + c\partial_1 - c^2\partial_2$$

In the above equation, $\in_m$ is the permittivity of the medium, $\in_w$ is the permittivity of water, c is the concentration of the solute, and $\partial$ equals the molar increments. For a determination of the molar increments for many possible solutes, reference is made to Arnold, "Positioning and Levitation Media for the Separation of Biological Cells," IEEE Transactions on Industry App., vol. 37(5), pp. 1468-1475 (2001) and Arnold et al., "Dielectric measurements on electro-manipulation media," Biochem. Biophys. Acta., vol. 1157, pp. 32-44, 1993, the entire contents of each of which are incorporated by reference herein. $\partial_2$ values for HEPES and related ions are small relative to $\partial_1$, resulting in a linear effect on $\in_m$.

Dielectric dispersion occurs when the polarization cannot follow the electric field at high frequencies. Dispersion tends to decrease the media permittivity and increase its conductivity. For most sugars reported in Arnold et al., "Dielectric measurements on electro-manipulation media," Biochem. Biophys. Acta., vol. 1157, pp. 32-44, 1993, permittivities and conductivities were substantially unchanged at concentrations less than about 1.2M, between 200 kHz and 2 MHz and thus dispersion may be minimized. Dispersion was observed for many high density solutes, such as, Percoll, Nicodenz, and Metrizamide, at higher frequencies.

It should be noted that sizes and configurations of various structural parts and materials used to make the above-mentioned parts are illustrative and exemplary only. One of ordinary skill in the art would recognize that those sizes, configurations, and materials can be changed to produce different effects and/or desired characteristics. Further, although many of the embodiments described above have been discussed in conjunction with using optoelectronic manipulation principles for applications relating to cellular analysis and other cell biology applications, it should be understood that the exemplary techniques and devices disclosed herein may be used for other applications wherein the manipulation of small particles is desirable, such as, for example, clinical diagnostics, drug discovery, environmental monitoring of bioparticles and non-bioparticles (e.g., detection of viral, bacterial, or protozoan entities in water samples and detection of non-biological particulates in water samples), characterization and/or isolation of non-cell microparticles (e.g., microsphere sizing or chemical/electrical characterization), and/or other applications wherein manipulation (including identification, sorting, separating, moving, quantitating, characterizing, etc.) of small particles may be desired. Yet other applications may include, but are not limited to, manipulation, including separation, of dye-labeled DNA, RNA, proteins, lipids, terpenes, glycoconjugates, and polysaccharides, for example.

As used in this application, the term "small particles" may include micro- and/or nano-particles, for example, particles having dimensions on the order of a few microns or a few nanometers. In the context of biological fluid analysis and/or handling, the term small particles may include cells, cell aggregates, cell organelles, stem cells, nucleic acids, bacteria, protozoans, viruses, and other biological particles.

In this application, the use of the singular includes the plural unless specifically stated otherwise. It is noted that, as used in this specification and the appended claims, the singular forms "a," "an," and "the," include plural referents unless expressly and unequivocally limited to one referent. In this application, the use of "or" means "and/or" unless stated otherwise. Furthermore, the use of the term "including", as well as other forms, such as "includes" and "included", is not limiting. As used herein, the term "include" and its grammatical variants are intended to be non-limiting, such that recitation of items in a list is not to the exclusion of other like items that can be substituted or added to the listed items. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only and are not to be construed as limiting the described subject matter in any way. All literature and similar materials cited in this application, including patents, patent applications, articles, books, treatises, and internet web pages are expressly incorporated by reference in their entirety for any purpose. In the event that one or more of the incorporated literature and similar materials defines or uses a term in such a way that it contradicts that term's definition in this application, this application controls. While the present teachings are described in conjunction with various exemplary embodiments, it is not intended that the present teachings be limited to such embodiments. On the contrary, the present teachings encompass various alternatives, modifications, and equivalents, as will be appreciated by those of skill in the art.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It will be apparent to those skilled in the art that various modifications and variations can be made to the structure and methodology of the present invention. Thus, it should be understood that the invention is not limited to the examples discussed in the specification. Rather, the present invention is intended to cover modifications and variations. Other embodiments of the invention will be apparent to those skilled in the art from consideration of the specification and practice of the invention disclosed herein.

What is claimed is:

1. A method for sorting cells in a biological sample comprising a first type of cells and a second type of cells, the method comprising:

introducing the biological sample into a chamber comprising a first surface and a second surface, wherein the first surface is associated with a transparent electrode and the second surface is associated with a photoconductive portion of an electrode, wherein the chamber includes a loop structure;

moving a first incident light of a first intensity and the photoconductive portion relative to one another so as to illuminate regions of the photoconductive portion and modulate an electric field in the chamber in proximity to the illuminated regions, wherein moving the first incident light and the photoconductive portion relative to one another comprises moving the first incident light and the photoconductive portion relative to one another in a continuous loop pattern around the loop structure;

moving a second incident light of a second intensity and the photoconductive portion relative to one another so as to illuminate regions of the photoconductive portion and to further modulate the electric field in the chamber in proximity to the illuminated regions, wherein moving the second incident light and the photoconductive portion relative to one another comprises moving the second incident light and the photoconductive portion relative to one another in the continuous loop pattern around the loop structure; and separating the first type of cells from the second type of cells in the chamber via dielectrophoretic movement of the first type of cells and the second type of cells caused by the modulated electric field, wherein a dielectrophoretic characteristic of at least one of the first type of cells and the second type of cells has been modified.

2. The method of claim 1, further comprising selecting a speed of relative movement between the incident light and the photoconductive portion based on dielectrophoretic movement characteristics of at least one of the first type of cells and the second type of cells.

3. The method of claim 2, wherein selecting the speed comprises selecting the speed based on predetermined dielectrophoretic movement characteristics of at least one of the first type of cells and the second type of cells.

4. The method of claim 2, wherein selecting the speed comprises selecting the speed based on dielectrophoretic movement characteristics of at least one of the first type of cells and the second type of cells observed from the separating step.

5. The method of claim 1, further comprising storing information regarding the dielectrophoretic movement characteristics of at least one of the first type of cells and the second type of cells.

6. The method of claim 1, further comprising identifying at least one of the first type of cells and the second type of cells from other types of cells based on observing the dielectrophoretic movement characteristics of at least one of the first type of cells and the second type of cells.

7. The method of claim 1, further comprising moving the first type of cells and the second type of cells to differing locations outside of the chamber, wherein the moving comprises moving at least one of the first type of cells and the second type of cells via dielectrophoretic movement.

8. The method of claim 1, further comprising applying an electrical potential generated via at least one of a DC power source and an AC power source across the transparent electrode and the electrode having a photoconductive portion so as to generate an electric field.

9. The method of claim 1, further comprising measuring the dielectrophoretic movement of each of the first type of cells and the second type of cells.

10. The method of claim 9, further comprising measuring a dielectrophoretic displacement of each of the first type of cells and the second type of cells after separating the first type of cells and the second type of cells.

11. The method of claim 1, further comprising moving at least one of the first type of cells and the second type of cells via electrophoresis.

12. The method of claim 1, further comprising altering the first intensity of the first incident light so as to modulate the electric field.

13. The method of claim 12, wherein altering the first intensity of the first incident light comprises altering the first intensity based on a position of the first incident light relative to the photoconductive portion.

14. The method of claim 1, further comprising repeating moving the first incident light and moving the second incident light so as to achieve a desired separating of the first type of cells and the second type of cells.

15. The method of claim 1, wherein moving the first incident light and moving the second incident light comprises selectively applying current to an array of electroluminescent material.

16. The method of claim 1, wherein moving the first incident light and moving the second incident light comprises generating an array of interdigitated virtual electrodes at illuminated regions of the photoconductive portion.

17. The method of claim 1, wherein separating the first type of cells from the second type of cells comprises separating tumor cells from nontumor cells.

18. The method of claim 1, wherein the chamber comprising a first surface and a second surface further comprises a second patternless surface associated with a photoconductive portion of an electrode.

19. A method for sorting cells in a biological sample comprising a first type of cells and a second type of cells, the method comprising:
- introducing the biological sample into a chamber comprising a first surface and a second surface, wherein the first surface is associated with a transparent electrode and the second surface is associated with a photoconductive portion of an electrode, wherein the chamber includes a loop structure;
- receiving information that indicates dielectrophoretic movement characteristics of the first type of cells and the second type of cells;
- selectively illuminating the second surface via a first incident light of a first intensity based on the information so as to modulate an electric field within the chamber and separate the first type of cells and the second type of cells from each other, wherein selectively illuminating the second surface via the first incident light comprises moving the first incident light and the photoconductive portion relative to one another in a continuous loop pattern around the loop structure;
- selectively illuminating the second surface via a second incident light of a second intensity based on the information so as to further modulate the electric field within the chamber and separate the first type of cells and the second type of cells from each other, wherein selectively illuminating the second surface via the second incident light comprises moving the second incident light and the photoconductive portion relative to one another in the continuous loop pattern around the loop structure.

20. The method of claim 19, wherein receiving the information comprises receiving information corresponding to dielectrophoretic displacement of each of the first type of cells and the second type of cells in response to the incident light illuminating the surface.

21. The method of claim 19, wherein selectively illuminating the surface comprises altering a speed of relative motion between the incident light and the surface.

22. The method of claim 19, wherein receiving the information comprises at least one of receiving stored information and receiving information obtained from an image of the biological sample in the chamber.

* * * * *